(12) United States Patent
Obidin

(10) Patent No.: US 11,939,312 B2
(45) Date of Patent: Mar. 26, 2024

(54) ENANTIOMERIC ENTACTOGEN COMPOSITIONS AND THEIR USE

(71) Applicant: Arcadia Medicine, Inc., San Francisco, CA (US)

(72) Inventor: Nikita Obidin, Seattle, WA (US)

(73) Assignee: Arcadia Medicine, Inc., San Francisco, CA (US)

( * ) Notice: Subject to any disclaimer, the term of this patent is extended or adjusted under 35 U.S.C. 154(b) by 0 days.

(21) Appl. No.: 18/230,142

(22) Filed: Aug. 3, 2023

(65) Prior Publication Data

US 2023/0382885 A1 Nov. 30, 2023

Related U.S. Application Data

(63) Continuation of application No. PCT/US2022/032275, filed on Jun. 3, 2022.

(60) Provisional application No. 63/196,226, filed on Jun. 3, 2021.

(51) Int. Cl.
*C07D 317/58* (2006.01)
*A61K 9/00* (2006.01)
*A61P 25/22* (2006.01)

(52) U.S. Cl.
CPC .......... *C07D 317/58* (2013.01); *A61K 9/0053* (2013.01); *A61P 25/22* (2018.01)

(58) Field of Classification Search
CPC .................................................. C07D 317/58
USPC ......................................................... 514/466
See application file for complete search history.

(56) References Cited

U.S. PATENT DOCUMENTS

| | | | |
|---|---|---|---|
| 4,327,725 A | 5/1982 | Cortese et al. |
| 4,624,848 A | 11/1986 | Lee |
| 4,871,549 A | 10/1989 | Ueda et al. |
| 4,968,509 A | 11/1990 | Radebaugh et al. |
| 5,011,692 A | 4/1991 | Fujioka et al. |
| 5,017,381 A | 5/1991 | Maruyama et al. |
| 5,229,135 A | 7/1993 | Philippon et al. |
| 5,260,068 A | 11/1993 | Chen |
| 5,260,069 A | 11/1993 | Chen |
| 5,456,923 A | 10/1995 | Nakamichi et al. |
| 5,461,140 A | 10/1995 | Heller et al. |
| 5,508,040 A | 4/1996 | Chen |
| 5,516,527 A | 5/1996 | Curatolo |
| 5,567,441 A | 10/1996 | Chen |
| 5,622,721 A | 4/1997 | Dansereau et al. |
| 5,686,105 A | 11/1997 | Kelm et al. |
| 5,700,410 A | 12/1997 | Nakamichi et al. |
| 5,837,284 A | 11/1998 | Mehta et al. |
| 5,840,329 A | 11/1998 | Bai |
| 5,977,175 A | 11/1999 | Lin |
| 6,465,014 B1 | 10/2002 | Moroni et al. |
| 6,932,983 B1 | 8/2005 | Straub et al. |
| 8,808,734 B2 | 8/2014 | Winnicki |
| 10,245,242 B1 | 4/2019 | Millet |
| 10,328,027 B2 | 6/2019 | Costa et al. |
| 10,588,876 B2 | 3/2020 | Millet |
| 2004/0220277 A1 | 11/2004 | Couch et al. |
| 2008/0045588 A1 | 2/2008 | Gant et al. |
| 2011/0021413 A1 | 1/2011 | Laskowitz et al. |
| 2015/0367091 A1 | 12/2015 | Djupesland et al. |
| 2016/0062931 A1 | 3/2016 | Darbari |
| 2017/0312308 A1 | 11/2017 | Meloni et al. |
| 2022/0354822 A1 | 11/2022 | Barrow et al. |
| 2023/0097530 A1 | 3/2023 | Short et al. |
| 2023/0129723 A1 | 4/2023 | Short et al. |
| 2023/0150963 A1 | 5/2023 | Baggott |
| 2023/0159487 A1 | 5/2023 | Baggott |
| 2023/0183199 A1 | 6/2023 | Baggott |
| 2023/0201159 A1 | 6/2023 | Kadysh et al. |
| 2023/0218568 A1 | 7/2023 | Liechti |
| 2023/0226019 A1 | 7/2023 | Barrow et al. |
| 2023/0226020 A1 | 7/2023 | Barrow et al. |
| 2023/0257347 A1 | 8/2023 | Baggott |
| 2023/0310368 A1 | 10/2023 | Barrow et al. |

FOREIGN PATENT DOCUMENTS

| | | |
|---|---|---|
| WO | 2005000334 A1 | 1/2005 |
| WO | 2008033351 A2 | 3/2008 |
| WO | 2011131947 A2 | 10/2011 |

(Continued)

OTHER PUBLICATIONS

Pitts et al., Psychopharmacology (2018) 235: 377-392. Cited in the spec, pp. 15.*
Taffe et al., "Hyperthermia Induced by 3,4-Methylenedioxymethamphetamine in Unrestrained Rhesus Monkeys," Drug and Alcohol Dependence, Nov. 11, 2005 (Nov. 11, 2005), vol. 82, No. 3, pp. 276-281. entire document.
Binder et al., "Association of FKBP5 Polymorphisms and Childhood Abuse With Risk of Posttraumatic Stress Disorder Symptoms in Adults," Journal of the American Medical Association, Mar. 19, 2008 (Mar. 19, 2008), vol. 299, No. 11, pp. 1291-1305. entire document.
Emke et al., Enantiomer profiling of high loads of amphetamine and MDMA in communal sewage: A Dutch perspeclive,* Nov. 28, 2013 (Nov. 28, 2013), vol. 487, pp. 666-672. endire document.

(Continued)

*Primary Examiner* — Taofiq A Solola
(74) *Attorney, Agent, or Firm* — Calyx Law; Graham Pechenik; Gregory Dwulet

(57) ABSTRACT

Provided are enantiomers of MDMA, such as R-MDMA and S-MDMA, and non-racemic mixtures thereof. In some embodiments, the provided mixtures comprise R-MDMA in enantiomeric excess. In other aspects, provided are methods of making such enantiomers and non-racemic mixtures, compositions thereof, and methods of using the same. In some aspects, features of the provided mixtures, compositions, and methods include improved pharmacokinetics, reduced toxicity, such as neurotoxicity, and a reduced potential for abuse. In some embodiments, improved pharmacokinetics include a reduced duration of action. In some embodiments, reduced toxicity and abuse potential result from distinct binding profiles compared to racemic MDMA, R-MDMA, or S-MDMA.

30 Claims, 12 Drawing Sheets

(56) References Cited

FOREIGN PATENT DOCUMENTS

| WO | 2021030571 A1 | 2/2021 |
|---|---|---|
| WO | 2021038500 A2 | 3/2021 |
| WO | 2022053696 A1 | 3/2022 |
| WO | 2022106947 A1 | 5/2022 |
| WO | 2022150525 A1 | 7/2022 |
| WO | 2022232948 A1 | 11/2022 |
| WO | 2022232949 A1 | 11/2022 |
| WO | 2023019369 A1 | 2/2023 |

OTHER PUBLICATIONS

PCT/US2022/032275, International Search Report (ISA/US), dated Dec. 8, 2022.
PCT/US2022/032275, Written Opinion of the International Searching Authority (ISA/US), dated Dec. 8, 2022.
PCT/US2022/032275, PCT Search Strategy and Results (ISA/US), dated Nov. 4, 2022.
Nair J., et al. Fully Validated, Multi-Kilogram cGMP Synthesis of MDMA. ACS Omega. 2022;7(1):900-907.
Barreiro J.C., et al. A High-Resolution Magic Angle Spinning NMR Study of the Enantiodiscrimination of 3,4-Methylenedioxymethamphetamine (MDMA) by an Immobilized Polysaccharide-Based Chiral Phase. PLoS One. 2016;11(9):e0162892.
Baumann M. H., et al. Potentially Mistaking Enantiomers for Different Compounds Due to the Self-Induced Diastereomeric Anisochronism (SIDA) Phenomenon. Symmetry. 2020;12(7):1106.
Baumann M. H., et al. 3,4-Methylenedioxymethamphetamine (MDMA) neurotoxicity in rats: a reappraisal of past and present findings. Psychopharmacol. 2007;189(4).
Berro L.F., et al. Acute Effects of 3,4-Methylenedioxymethamphetamine (MDMA) and R(−) MDMA on Actigraphy-Based Daytime Activity and Sleep Parameters in Rhesus Monkeys. Exp Clin Psychopharmacol. 2018;26(4):410-420.
Bogenschutz M.P. & Forcehimes A.A. Development of a Psychotherapeutic Model for Psilocybin-Assisted Treatment of Alcoholism. J Humanist Psychol. 2017;57(4):389-414.
Capela J.P., et al. Ecstasy induces apoptosis via 5-HT2A-receptor stimulation in cortical neurons. Neurotoxicology. 2007;28(4):868-875.
Carvalho M., et al. Mechanisms Underlying the Hepatotoxic Effects of Ecstasy. Curr Pharm Biotechnol. 2010;11(5):476-495.
Curry D. W., et al. Separating the agony from ecstasy: R(e)-3,4-methylenedioxymethamphetamine has prosocial and therapeutic-like effects without signs of neurotoxicity in mice. Neuropharmacology. 2018;128:196-206.
Dunlap L. E., et al. Dark Classics in Chemical Neuroscience: 3,4-Methylenedioxymethamphetamine (MDMA). ACS Chem Neurosci. 2018; 9(10):2408-2427.
Fattore L., et al. Analysis of Opioid-Seeking Behavior Through the Intravenous Self-Administration Reinstatement Model in Rats. Methods Mol Biol. 2021;2201:231-245.
Felim A., et al. Synthesis and in vitro cytotoxicity profile of the R-enantiomer of 3,4-dihydroxymethamphetamine (R-(−)-HHMA): comparison with related catecholamines. Chem Res Toxicol. 2010;23(1):211-219.
Fresqui M.A., et al. The influence of R and S configurations of a series of amphetamine derivatives on quantitative structure-activity relationship models. Anal Chim Acta. 2013;759:43-52.
Glennon R.A., et al. 5-HT1 and 5-HT2 binding characteristics of 1-(2,5-dimethoxy-4-bromophenyl)-2-aminopropane analogues. J Med Chem. 1986;29(2):194-199.
Goodwin A.K., et al. A three-choice discrimination procedure dissociates the discriminative stimulus effects of d-amphetamine and (+/−)-MDMA in rats. Exp Clin Psychopharmacol. 2000;8(3):415-423.
Green A.R. et al. Lost in translation: preclinical studies on 3,4-methylenedioxymethamphetamine provide information on mechanisms of action, but do not allow accurate prediction of adverse events in humans. Br J Pharmacol. 2012;166(5):1523-1536.
Harris D.S., et al. Subjective and hormonal effects of 3,4-methylenedioxymethamphetamine (MDMA) in humans. Psychopharmacology (Berl). 2002;162(4):396-405.
Huang R.Y. et al. Isobologram Analysis: A Comprehensive Review of Methodology and Current Research. Front Pharmacol. 2019;10:1222.
Huang Y.S., et al. Chiral separation of 3,4-methylenedioxymethamphetamine and related compounds in clandestine tablets and urine samples by capillary electrophoresis/fluorescence spectroscopy. Electrophoresis. 2003;24(6):1097-1104.
Huang Y.S., et al. Comparison of the use of aqueous and nonaqueous buffers in association with cyclodextrin for the chiral separation of 3,4-methylenedioxymethamphetamine and related compounds. Electrophoresis. 2005;26(20):3904-3909.
Huot P., et al. Characterization of 3,4-methylenedioxymethamphetamine (MDMA) enantiomers in vitro and in the MPTP-lesioned primate: R-MDMA reduces severity of dyskinesia, whereas S-MDMA extends duration of ON-time. J Neurosci. 2011;31(19):7190-8.
Johnson M.P., et al. Neurotoxic effects of the alpha-ethyl homologue of MDMA following subacute administration. Pharmacol Biochem Behav. 1989;33(1):105-108.
Johnson M.P., et al. Effects of the enantiomers of MDA, MDMA and related analogues on [3H]serotonin and [3H]dopamine release from superfused rat brain slices. Eur J Pharmacol. 1986;132(2-3):269-276.
Kadkhodaei K., et al. Separation of enantiomers of new psychoactive substances by high-performance liquid chromatography. J Sep Sci. 2018;41(6):1274-1286.
Kampman K., et al. American Society of Addiction Medicine (ASAM) National Practice Guideline for the Use of Medications in the Treatment of Addiction Involving Opioid Use. J Addict Med. 2015;9(5):358-367.
Kasteel E.E.J., et al. Refining in vitro and in silico neurotoxicity approaches by accounting for interspecies and interindividual differences in toxicodynamics. Expert Opin Drug Metab Toxicol. 2021;17(8):1007-1017.
Knights K.M., et al. In Vitro Drug Metabolism Using Liver Microsomes. Curr Protoc Pharmacol. 2016;74:7.8.1-7.8.24.
Lai F.Y., et al. Liquid chromatography-quadrupole time-of-flight mass spectrometry for screening in vitro drug metabolites in humans: investigation on seven phenethylamine-based designer drugs. J Pharm Biomed Anal. 2015;114:355-375.
Lebsanft H.B., et al. 3,4-Methylenedioxymethamphetamine counteracts akinesia enantioselectively in rat rotational behavior and catalepsy. Synapse. 2005;55(3):148-155.
Llabrés S., et al. Molecular basis of the selective binding of MDMA enantiomers to the alpha4beta2 nicotinic receptor subtype: synthesis, pharmacological evaluation and mechanistic studies. Eur J Med Chem. 2014;81:35-46.
Mas M., et al. Cardiovascular and neuroendocrine effects and pharmacokinetics of 3, 4-methylenedioxymethamphetamine in humans. J Pharmacol Exp Ther. 1999;290(1):136-145.
Meyer M.R., et al. The role of human hepatic cytochrome P450 isozymes in the metabolism of racemic 3,4-methylenedioxymethamphetamine and its enantiomers. Drug Metab Dispos. 2008;36(11):2345-2354.
Murnane K.S., et al. Endocrine and neurochemical effects of 3,4-methylenedioxymethamphetamine and its stereoisomers in rhesus monkeys. J Pharmacol Exp Ther. 2010;334(2):642-650.
Niwa T., et al. Stereoselectivity of human cytochrome p450 in metabolic and inhibitory activities. Curr Drug Metab. 2011;12(6):549-569.
Oberlender, R., et al. Drug discrimination studies with MDMA and amphetamine. Psychopharmacology. 1988;95(1):71-76.
Oeri H.E. Beyond ecstasy: Alternative entactogens to 3,4-methylenedioxymethamphetamine with potential applications in psychotherapy. J Psychopharmacol. 2021;35(5):512-536.
Padivitage N.L., et al. Enantiomeric separations of illicit drugs and controlled substances using cyclofructan-based (LARIHC) and cyclobond I 2000 RSP HPLC chiral stationary phases. Drug Test Anal. 2014;6(6):542-551.

(56) References Cited

OTHER PUBLICATIONS

Partilla J.S., et al. Interaction of amphetamines and related compounds at the vesicular monoamine transporter. J Pharmacol Exp Ther. 2006;319(1):237-246.
Pierce R.C., et al. The mesolimbic dopamine system: the final common pathway for the reinforcing effect of drugs of abuse?. Neurosci Biobehav Rev. 2006;30(2):215-238.
Pitts E.G., et al. (±)-MDMA and its enantiomers: potential therapeutic advantages of R(−)-MDMA. Psychopharmacology (Berl). 2018;235(2):377-392.
Rasmussen L.B., et al. Chiral separation and quantification of R/S-amphetamine, R/S-methamphetamine, R/S-MDA, R/S-MDMA, and R/S-MDEA in whole blood by GC-EI-MS. J Chromatogr B Analyt Technol Biomed Life Sci. 2006;842(2):136-141.
Sadeghipour F., et al. Enantiomeric separation of four methylenedioxylated amphetamines on β-cyclodextrin chiral stationary phases. Chromatographia. 1998;47:285-290.
Squire H., et al. The role of dopamine D1 receptors in MDMA-induced memory impairments. Neurobiol Learn Mem. 2020;176:107322.
Steele T.D., et al. Stereochemical effects of 3,4-methylenedioxymethamphetamine (MDMA) and related amphetamine derivatives on inhibition of uptake of [3H]monoamines into synaptosomes from different regions of rat brain. Biochem Pharmacol. 1987;36(14):2297-2303.
Steenkamp M.M., et al. First-line Psychotherapies for Military-Related PTSD. JAMA. 2020;323(7):656-657.
Steidl S., et al. Opioid-induced rewards, locomotion, and dopamine activation: A proposed model for control by mesopontine and rostromedial tegmental neurons. Neurosci Biobehav Rev. 2017;83:72-82.
Sáez-Briones P., et al. MDMA (3,4-Methylenedioxymethamphetamine) Analogues as Tools to Characterize MDMA-Like Effects: An Approach to Understand Entactogen Pharmacology. Curr Neuropharmacol. 2013;11(5):521-534.
Tagliaro F., et al. Simultaneous chiral separation of 3,4-methylenedioxymethamphet-amine, 3-4-methylenedioxyamphetamine, 3,4-methylenedioxyethylam-phetamine, ephedrine, amphetamine and methamphetamine by capillary electrophoresis in uncoated and coated capillaries with native beta-cyclodextrin as the chiral selector: preliminary application to the analysis of urine and hair. Electrophoresis. 1998;19(1):42-50.
Wan Aasim, W.R., et al. Interspecies In Vitro Evaluation of Stereoselective Protein Binding for 3,4-Methylenedioxymethamphetamine. J Chem. 2017;2017:7.
White R.F., et al. Functional MRI approach to developmental methylmercury and polychlorinated biphenyl neurotoxicity. Neurotoxicology. 2011;32(6):975-980.
Zhou J.F., et al. 3,4-Methylenedioxymethamphetamine (MDMA) abuse may cause oxidative stress and potential free radical damage. Free Radic Res. 2003;37(5):491-497.
Zimmer B.A, et al. Cocaine self-administration in rats: hold-down procedures. Methods Mol Biol. 2012;829:279-290.
Kalant H. The pharmacology and toxicology of "ecstasy" (MDMA) and related drugs. CMAJ. 2001;165(7):917-928.
Fallon J.K., et al. Stereospecific analysis and enantiomeric disposition of 3, 4-methylenedioxymethamphetamine (Ecstasy) in humans. Clin Chem. 1999;45(7):1058-1069.
Cordero-Erasquin M., et al. Nicotinic receptor function: new perspectives from knockout mice. Trends Pharmacol Sci. 2000;21(6):211-217.
Pizarro N., et al. Synthesis and capillary electrophoretic analysis of enantiomerically enriched reference standards of MDMA and its main metabolites. Bioorg Med Chem. 2002;10(4):1085-1092.
Pizarro N., et al. Determination of MDMA and its metabolites in blood and urine by gas chromatography-mass spectrometry and analysis of enantiomers by capillary electrophoresis. J Anal Toxicol. 2002;26(3):157-165.
Tucker G.T., et al. The demethylenation of methylenedioxymethamphetamine ("ecstasy") by debrisoquine hydroxylase (CYP2D6). Biochem Pharmacol. 1994;47(7):1151-1156.
Verrico C.D., et al. MDMA (Ecstasy) and human dopamine, norepinephrine, and serotonin transporters: implications for MDMA-induced neurotoxicity and treatment. Psychopharmacology (Berl). 2007;189(4):489-503.
Mithoefer M.C., et al. MDMA-assisted psychotherapy for treatment of PTSD: study design and rationale for phase 3 trials based on pooled analysis of six phase 2 randomized controlled trials. Psychopharmacology (Berl). 2019;236(9):2735-2745.
Mithoefer M.C., et al. Durability of improvement in post-traumatic stress disorder symptoms and absence of harmful effects or drug dependency after 3,4-methylenedioxymethamphetamine-assisted psychotherapy: a prospective long-term follow-up study. J Psychopharmacol. 2013;27(1):28-39.
Mithoefer M.C., et al. The safety and efficacy of {+/−}3,4-methylenedioxymethamphetamine-assisted psychotherapy in subjects with chronic, treatment-resistant posttraumatic stress disorder: the first randomized controlled pilot study. J Psychopharmacol. 2011;25(4):439-452.
Hysek C.M., et al. MDMA enhances emotional empathy and prosocial behavior. Soc Cogn Affect Neurosci. 2014;9(11):1645-1652.
Sessa B., et al. A Review of 3,4-methylenedioxymethamphetamine (MDMA)-Assisted Psychotherapy. Front Psychiatry. 2019;10:138.
Feduccia A.A., et al. Breakthrough for Trauma Treatment: Safety and Efficacy of MDMA-Assisted Psychotherapy Compared to Paroxetine and Sertraline. Focus (Am Psychiatr Publ). 2023;21(3):306-314.
Lourenço T.C., et al. Chiral separation of 3,4-methylenedioxymethamphetamine (MDMA) enantiomers using batch chromatography with peak shaving recycling and its effects on oxidative stress status in rat liver. J Pharm Biomed Anal. 2013;73:13-17.
Hiramatsu M., et al. Enantiomeric differences in the effects of 3,4-methylenedioxymethamphetamine on extracellular monoamines and metabolites in the striatum of freely-moving rats: an in vivo microdialysis study. Neuropharmacology. 1990;29(3):269-275.
Setola V., et al. 3,4-methylenedioxymethamphetamine (MDMA, "Ecstasy") induces fenfluramine-like proliferative actions on human cardiac valvular interstitial cells in vitro. Mol Pharmacol. 2003;63(6):1223-1229.
Anderson G.M., et al. Absolute configuration and psychotomimetic activity. NIDA Res Monogr. 1978;(22):8-15.
Polavarapu P.L. Optical purity, enantiomeric excess and the Horeau effect. Org Biomol Chem. 2020;18(35):6801-6806.
Nichols D.E., et al. Asymmetric synthesis of psychotomimetic phenylisopropylamines. J Med Chem. 1973;16(5):480-483.
Nichols D.E., et al. Derivatives of 1-(1,3-benzodioxol-5-yl)-2-butanamine: representatives of a novel therapeutic class. J Med Chem. 1986;29(10):2009-2015.
Nichols D.E., et al. 2,3-Dihydrobenzofuran analogues of hallucinogenic phenethylamines. J Med Chem. 1991;34(1):276-281.
Kedrowski SM, et al. 1-Oxo-5-hydroxytryptamine: a surprisingly potent agonist of the 5-HT3 (serotonin) receptor. Org Lett. 2007;9(17):3205-3207.
Indave B.I., et al. Antipsychotic medications for cocaine dependence. Cochrane Database Syst Rev. Mar. 19, 2016;3(3):CD006306.
Keri R.S., et al. An overview of benzo[b]thiophene-based medicinal chemistry. Eur J Med Chem. 2017;138:1002-1033.
Pérez-Silanes S., et al. Synthesis of new 5-substitutedbenzo[b]thiophene derivatives. J Heterocycl Chem. 2001;38:1025-1030.
Han J., et al. The self-disproportionation of enantiomers (SDE): a menace or an opportunity?. Chem Sci. 2018;9(7):1718-1739.
Berge S.M., et al. Pharmaceutical salts. J Pharm Sci. 1977;66(1):1-19.
Baumann M.H., et al. Tolerance to 3,4-methylenedioxymethamphetamine in rats exposed to single high-dose binges. Neuroscience. 2008;152(3):773-784.

(56) References Cited

OTHER PUBLICATIONS

Kalivas P.W., et al. MDMA elicits behavioral and neurochemical sensitization in rats. Neuropsychopharmacology. 1998;18(6):469-479.
Brennan K.A., et al. Initial deficit and recovery of function after MDMA preexposure in rats. Psychopharmacology (Berl). 2006;184(2):239-246.
McClung J., et al. Reinstatement of extinguished amphetamine self-administration by 3,4-methylenedioxymethamphetamine (MDMA) and its enantiomers in rhesus monkeys. Psychopharmacology (Berl). 2010;210(1):75-83.
Oehen P., et al. A randomized, controlled pilot study of MDMA (± 3,4-Methylenedioxymethamphetamine)-assisted psychotherapy for treatment of resistant, chronic Post-Traumatic Stress Disorder (PTSD). J Psychopharmacol. 2013;27(1):40-52.
Chabrol H. MDMA assisted psychotherapy found to have a large effect for chronic post-traumatic stress disorder. J Psychopharmacol. 2013;27(9):865-866.
Costa G., et al. Neurotoxicity of MDMA: Main effects and mechanisms. Exp Neurol. 2022;347:113894.
Rudin D., et al. Molecular and clinical aspects of potential neurotoxicity induced by new psychoactive stimulants and psychedelics. Exp Neurol. 2021;343:113778.
Steinkellner T., et al. The ugly side of amphetamines: short- and long-term toxicity of 3,4-methylenedioxymethamphetamine (MDMA, 'Ecstasy'), methamphetamine and D-amphetamine. Biol Chem. 2011;392(1-2):103-115.
Taghizadeh G., et al. Protective effects of physical exercise on MDMA-induced cognitive and mitochondrial impairment. Free Radic Biol Med. 2016;99:11-19.
Roth B. National institute of mental health psychoactive drug screening program. In Assay Protocol Book; Department of Pharmacology, University of North Carolina at Chapel Hill: Chapel Hill, NC, USA, 2018.
Chefer V.I., et al. Overview of brain microdialysis. Curr Protoc Neurosci. 2009;Chapter 7:Unit7.1.
Darvesh A.S., et al. In vivo brain microdialysis: advances in neuropsychopharmacology and drug discovery. Expert Opin Drug Discov. 2011;6(2):109-127.
Wong D.F., et al. Monoamines: Human brain imaging. In Encyclopedia of Neuroscience. 2009. pp. 939-952. Elsevier Ltd.
Takano H. Cognitive Function and Monoamine Neurotransmission in Schizophrenia: Evidence From Positron Emission Tomography Studies. Front Psychiatry. 2018;9:228.
Pilecki B., et al. Ethical and legal issues in psychedelic harm reduction and integration therapy. Harm Reduct J. 2021;18(1):40.
Davis L.L., et al. The Economic Burden of Posttraumatic Stress Disorder in the United States From a Societal Perspective. J Clin Psychiatry. 2022;83(3):21m14116.
Wolfson P.E., et al. MDMA-assisted psychotherapy for treatment of anxiety and other psychological distress related to life-threatening illnesses: a randomized pilot study. Sci Rep. 2020;10(1):20442.
Ranta K., et al. Social Anxiety Scale for Adolescents (SAS-A): measuring social anxiety among Finnish adolescents. Child Psychiatry Hum Dev. 2012;43(4):574-591.
Danforth A.L., et al. Reduction in social anxiety after MDMA-assisted psychotherapy with autistic adults: a randomized, double-blind, placebo-controlled pilot study. Psychopharmacology (Berl). 2018;235(11):3137-3148.
Jahan A.R., et al. Substance Use Disorder. In: StatPearls. Treasure Island (FL): StatPearls Publishing; Jul. 21, 2023.
MAPS Investigator's Brochure 13th Edition. 2021. San Jose, CA. p. 18.
Nowinski, J. et al. Project MATCH Monograph Series. vol. 1, NIH Publication. 1995 No. 94-3722.
Shulgin & Shulgin. PiHKAL: A Chemical Love Story, 1992 Transform Press.
Shulgin & Shulgin.TIHKAL: The Continuation, 1997 Transform Press.
Obidin N. (Jun. 26, 2020). Enantiomeric MDMA and neurotoxicity. Nikita Obidin. http://nikobidin.com/mdma-and-neurotoxicity.
Mueller F., et al. Neuroimaging in moderate MDMA use: A systematic review. Neurosci Biobehav Rev. 2016;62:21-34.
O'Hearn E., et al. Methylenedioxyamphetamine (MDA) and methylenedioxymethamphetamine (MDMA) cause selective ablation of serotonergic axon terminals in forebrain: immunocytochemical evidence for neurotoxicity. J Neurosci. 1988;8(8):2788-2803.
Parrott A.C. Chronic tolerance to recreational MDMA (3,4-methylenedioxymethamphetamine) or Ecstasy. J Psychopharmacol. 2005;19(1):71-83.
Chaliha D., et al. A Systematic Review of the MDMA Model to Address Social Impairment in Autism. Curr Neuropharmacol. 2021;19(7):1101-1154.
Diana M. The dopamine hypothesis of drug addiction and its potential therapeutic value. Front Psychiatry. 2011;2:64.
Foster S.L., et al. The Role of Norepinephrine in Drug Addiction: Past, Present, and Future. Neural Mechanisms of Addiction. 2019. 221-236.
Edwards G. The alcohol dependence syndrome: a concept as stimulus to enquiry. Br J Addict. 1986;81(2):171-183.
Robinson S.M., et al. Reliability of the Timeline Followback for cocaine, cannabis, and cigarette use. Psychol Addict Behav. 2014;28(1):154-162.
Sobell L.C., et al. The reliability of the Alcohol Timeline Followback when administered by telephone and by computer. Drug Alcohol Depend. 1996;42(1):49-54.
Al-Hasani R., et al. Molecular mechanisms of opioid receptor-dependent signaling and behavior. Anesthesiology. 2011;115(6):1363-1381.
Kosten T.R., et al. The neurobiology of opioid dependence: implications for treatment. Sci Pract Perspect. 2002;1(1):13-20.
Fields H.L., et al. Understanding opioid reward. Trends Neurosci. 2015;38(4):217-225.
Minozzi S., et al. Dopamine agonists for the treatment of cocaine dependence. Cochrane Database Syst Rev. 2011;(12):CD003352.
Galaj E, et al. Dopamine D3 receptor-based medication development for the treatment of opioid use disorder: Rationale, progress, and challenges. Neurosci Biobehav Rev. 2020;114:38-52.
Laviolette S.R., et al. The neurobiology of nicotine addiction: bridging the gap from molecules to behaviour. Nat Rev Neurosci. 2004;5(1):55-65.
Nisell M., et al. Systemic nicotine-induced dopamine release in the rat nucleus accumbens is regulated by nicotinic receptors in the ventral tegmental area. Synapse. 1994;16(1):36-44.
Baker T.B., et al. DSM criteria for tobacco use disorder and tobacco withdrawal: a critique and proposed revisions for DSM-5. Addiction. 2012;107(2):263-275.
O'Dell L.E., et al. Rodent models of nicotine reward: what do they tell us about tobacco abuse in humans?. Pharmacol Biochem Behav. 2009;91(4):481-488.
Sofuoglu M., et al. Norepinephrine and stimulant addiction. Addict Biol. 2009;14(2):119-129.
Wise R.A. Catecholamine theories of reward: a critical review. Brain Res. 1978;152(2):215-247.
Ronsley C., et al. Treatment of stimulant use disorder: A systematic review of reviews. PLoS One. 2020;15(6):e0234809.
Jaiswal M., et al. Nanoemulsion: an advanced mode of drug delivery system. 3 Biotech. 2015;5(2):123-127.
Wilson A.R., et al. Repeated cannabinoid injections into the rat periaqueductal gray enhance subsequent morphine antinociception. Neuropharmacology. 2008;55(7):1219-1225.
Arza R.A., et al. Formulation and evaluation of swellable and floating gastroretentive ciprofloxacin hydrochloride tablets. AAPS PharmSciTech. 2009;10(1):220-226.
Fantegrossi W.E., et al. Pharmacological characterization of the effects of 3,4-methylenedioxymethamphetamine ("ecstasy") and its enantiomers on lethality, core temperature, and locomotor activity in singly housed and crowded mice. Psychopharmacology (Berl). 2003;166(3):202-211.
Adams CE, et al. Contingency management for patients with cooccurring disorders: evaluation of a case study and recommendations for practitioners. Case Rep Psychiatry. 2012;2012:731638.

(56) References Cited

OTHER PUBLICATIONS

Karimi M., et al. DeepAffinity: interpretable deep learning of compound-protein affinity through unified recurrent and convolutional neural networks. Bioinformatics. 2019;35(18):3329-3338.
De La Torre R., et al. Non-linear pharmacokinetics of MDMA ('ecstasy') in humans. Br J Clin Pharmacol. 2000;49(2):104-109.
Fitzgerald R.L., et al. Stereoselective pharmacokinetics of 3,4-methylenedioxymethamphetamine in the rat. Chirality. 1990;2(4):241-248.
Carhart-Harris R.L., et al. Experienced drug users assess the relative harms and benefits of drugs: a web-based survey. J Psychoactive Drugs. 2013;45(4):322-328.
Rohsenow D.J., et al. Brief coping skills treatment for cocaine abuse: 12-month substance use outcomes. J Consult Clin Psychol. 2000;68(3):515-520.
De La Torre R., et al. MDMA, methamphetamine, and CYP2D6 pharmacogenetics: what is clinically relevant?. Front Genet. 2012;3:235.
Carvalho M., et al. Metabolism is required for the expression of ecstasy-induced cardiotoxicity in vitro. Chem Res Toxicol. 2004;17(5):623-632.
Helmin H.J., et al. Analysis of 3,4-methylenedioxymethamphetamine (MDMA) and its metabolites in plasma and urine by HPLC-DAD and GC-MS. J Anal Toxicol. 1996;20(6):432-440.
Liechti M.E. Effects of MDMA on body temperature in humans. Temperature (Austin). 2014;1(3):192-200.
Von Huben S.N., et al. Impact of ambient temperature on hyperthermia induced by (+/−)3,4-methylenedioxymethamphetamine in rhesus macaques. Neuropsychopharmacology. 2007;32(3):673-681.
Crean R.D., et al. Oral administration of (+/−)3,4-methylenedioxymethamphetamine and (+)methamphetamine alters temperature and activity in rhesus macaques. Pharmacol Biochem Behav. 2007;87(1):11-19.
Mitchell J., et al. Reply to: Caution at psychiatry's psychedelic frontier and Challenges with benchmarking of MDMA-assisted psychotherapy. Nat Med. 2021;27(10):1691-1692.
Battaglia G., et al. 3,4-Methylenedioxymethamphetamine and 3,4-methylenedioxyamphetamine destroy serotonin terminals in rat brain: quantification of neurodegeneration by measurement of [3H]paroxetine-labeled serotonin uptake sites. J Pharmacol Exp Ther. 1987;242(3):911-916.

McKee S.A., et al. Enhancing brief cognitive-behavioral therapy with motivational enhancement techniques in cocaine users. Drug Alcohol Depend. 2007;91(1):97-101.
Frau L., et al. Microglial and astroglial activation by 3,4-methylenedioxymethamphetamine (MDMA) in mice depends on S(+) enantiomer and is associated with an increase in body temperature and motility. J Neurochem. 2013;124(1):69-78.
Granado N., et al. D1 but not D4 dopamine receptors are critical for MDMA-induced neurotoxicity in mice. Neurotox Res. 2014;25(1):100-109.
Commins D.L., et al. Biochemical and histological evidence that methylenedioxymethylamphetamine (MDMA) is toxic to neurons in the rat brain. J Pharmacol Exp Ther. 1987;241(1):338-345.
Heifets B.D., et al. Distinct neural mechanisms for the prosocial and rewarding properties of MDMA. Sci Transl Med. 2019;11(522):eaaw6435.
Wang Z., et al. Estimating the relative reinforcing strength of (+/−)-3,4-methylenedioxymethamphetamine (MDMA) and its isomers in rhesus monkeys: comparison to (+)-methamphetamine. Psychopharmacology (Berl). 2007;189(4):483-488.
Yehuda R., et al. The Meaning of Evidence-Based Treatments for Veterans With Posttraumatic Stress Disorder. JAMA Psychiatry. 2016;73(5):433-434.
Bierer L.M., et al. Intergenerational Effects of Maternal Holocaust Exposure on FKBP5 Methylation. Am J Psychiatry. 2020;177(8):744-753.
Crits-Cristoph P., et al. Psychosocial treatments for cocaine dependence: National Institute on Drug Abuse Collaborative Cocaine Treatment Study. Arch Gen Psychiatry. 1999;56(6):493-502.
Petry N.M., et al. Prize reinforcement contingency management for cocaine dependence: integration with group therapy in a methadone clinic. J Consult Clin Psychol. 2005;73(2):354-359.
Barry D., et al. Comparable efficacy of contingency management for cocaine dependence among African American, Hispanic, and White methadone maintenance clients. Psychol Addict Behav. 2009;23(1):168-174.
Roozen H.G., et al. A systematic review of the effectiveness of the community reinforcement approach in alcohol, cocaine and opioid addiction. Drug Alcohol Depend. 2004;74(1):1-13.
Stotts A.L., et al. Motivational interviewing with cocaine-dependent patients: a pilot study. J Consult Clin Psychol. 2001;69(5):858-862.

* cited by examiner

R-MDMA

S-MDMA

ENANTIOMERIC ENTACTOGEN COMPOSITIONS AND THEIR USE

CROSS-REFERENCE

This application is a continuation of International Application No. PCT/US2022/032275, filed in the U.S. Receiving Office on Jun. 3, 2022, which claims the benefit of priority under PCT Article 8(1) and Rule 4.10 to U.S. Provisional Application No. 63/196,226, filed Jun. 3, 2021, both of which are incorporated by reference for all purposes as if fully set forth herein.

FIELD OF THE INVENTION

Enantiomeric entactogen compounds, and compositions and formulations thereof, as well as methods of their use to treat mental health disorders, such as mood disorders and PTSD.

BACKGROUND OF THE INVENTION

Various strategies are used to treat mental health disorders. The entactogen MDMA has emerged as a therapeutic option, for example to treat post-traumatic stress disorder (PTSD). However, improved therapies are needed to provide effective compounds with improved properties, such as a reduced potential for neurotoxicity and tolerance. Provided herein are certain non-racemic mixtures of MDMA, methods of making them, pharmaceutical compositions thereof, and methods of their use in medicine to meet these and other needs.

INCORPORATION BY REFERENCE

Each cited patent, publication, and non-patent literature is incorporated by reference in its entirety as if incorporated by reference individually. Unless specifically stated otherwise, reference is not to be construed as an admission that a document or any underlying information therein is prior art in any jurisdiction, or forms part of the common general knowledge in the art.

BRIEF SUMMARY OF THE INVENTION

The following presents a simplified summary of some embodiments of the invention in order to provide a basic understanding thereof. This summary is not an extensive overview, nor is it intended to identify every key or critical element of the invention or to delineate the complete scope of the invention. Its sole purpose is to present some exemplary embodiments of the invention in a simplified form, as a prelude to the more detailed description below.

In some aspects, provided herein are non-racemic mixtures comprising R(−)-3,4-methylenedioxymethamphetamine (R-MDMA) and S(+)-3,4-methylenedioxymethamphetamine (S-MDMA), including salts thereof. In some embodiments, the non-racemic mixture comprises R-MDMA in enantiomeric excess. In some embodiments, the non-racemic mixture comprises 90% or less of R-MDMA and 10% or more of S-MDMA. In some embodiments, the non-racemic mixture comprises R-MDMA in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the non-racemic mixture comprises R-MDMA in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the non-racemic mixture comprises R-MDMA in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the non-racemic mixture comprises R-MDMA in enantiomeric excess of about 75%, 76%, 77%, 78%, 79%, 80%, 81%, 82%, 83%, 84%, or 85%. In some embodiments, the non-racemic mixture comprises R-MDMA in enantiomeric excess of about 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1%. In some embodiments, the non-racemic mixture comprises R-MDMA in enantiomeric excess of about 79.5%, 79.6%, 79.7%, 79.8%, 79.9%, 80%, 80.1%, 80.2%, 80.3%, 80.4%, or 80.5%.

In some embodiments, the non-racemic mixture comprises R-MDMA to S-MDMA in a ratio of about 6:1 to 12:1, 7:1 to 11:1, or 8:1 to 10:1. In some embodiments, the non-racemic mixture comprises R-MDMA to S-MDMA in a ratio of about 6:1, 7:1, 8:1, 9:1, 10:1, 11:1, or 12:1. In some embodiments, the non-racemic mixture comprises R-MDMA to S-MDMA in a ratio of 9:1. The non-racemic mixture of claim 12, comprising R-MDMA in enantiomeric excess of within 0.05% of 90%, or within 0.1% of 90%.

In some embodiments, the salt is a hydrochloride, sulfate, tartrate, sodium, acetate, phosphate, chloride, or potassium salt. In some embodiments, the salt of R-MDMA and the salt of S-MDMA are the same. In some embodiments, the salt of R-MDMA and the salt of S-MDMA are different. In some embodiments, R-MDMA HCl and S-MDMA HCl are present in a ratio of about 6:1, 7:1, 8:1, 9:1, 10:1, 11:1, or 12:1. In some embodiments, R-MDMA HCl and S-MDMA HCl are present at a ratio of 9:1. In embodiments, R-MDMA HCl is present in enantiomeric excess of within 0.05% of 90%, or within 0.1% of 90%.

In some aspects, provided herein are pharmaceutical compositions comprising any of the described non-racemic mixtures, including pharmaceutically acceptable salts thereof. In some embodiments, the pharmaceutical compositions comprise R-MDMA in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the pharmaceutical compositions comprise R-MDMA in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the pharmaceutical compositions comprise R-MDMA in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the pharmaceutical compositions comprise R-MDMA in enantiomeric excess of about 75%, 76%, 77%, 78%, 79%, 80%, 81%, 82%, 83%, 84%, or 85%. In some embodiments, the pharmaceutical compositions comprise R-MDMA in enantiomeric excess of about 79% to 81%, 79.1% to 80.9%, 79.2% to 80.8%, 79.3% to 80.7%, 79.4% to 80.6%, 79.5% to 80.5%, 79.6% to 80.4%, 79.7%, 80.3% 79.8% to 80.2%, or 79.9% to 80.1%. In embodiments, the pharmaceutical compositions comprise R-MDMA in enantiomeric excess of about 79.5%, 79.6%, 79.7%, 79.8%, 79.9%, 80%, 80.1%, 80.2%, 80.3%, 80.4%, or 80.5%.

In some embodiments, the pharmaceutical compositions comprise R-MDMA and S-MDMA in a ratio of about 6:1 to 12:1, 7:1 to 11:1, or 8:1 to 10:1. In some embodiments, the pharmaceutical compositions comprise R-MDMA and S-MDMA in a ratio of about 6:1, 7:1, 8:1, 9:1, 10:1, 11:1, or 12:1. In some embodiments, the pharmaceutical compositions comprise R-MDMA and S-MDMA in a ratio of a ratio of 9:1. In some embodiments, the pharmaceutical compositions comprise R-MDMA in enantiomeric excess of within 0.05% or within 0.1% of 90%.

In some embodiments, the pharmaceutically acceptable salt is a hydrochloride, sulfate, tartrate, sodium, acetate, phosphate, chloride, or potassium salt. In some embodiments, the pharmaceutically acceptable salt of R-MDMA and the pharmaceutically acceptable salt of S-MDMA are the same. In embodiments, the pharmaceutically acceptable salt of R-MDMA and the pharmaceutically acceptable salt of S-MDMA are different.

In some embodiments, the pharmaceutical compositions comprise R-MDMA HCl and S-MDMA HCl in a ratio of about 6:1, 7:1, 8:1, 9:1, 10:1, 11:1, or 12:1. In some embodiments, the pharmaceutical compositions comprise R-MDMA HCl and S-MDMA HCl in a ratio of 9:1. In some embodiments, the pharmaceutical compositions comprise R-MDMA HCl in enantiomeric excess of within 0.05% of 90%, or within 0.1% of 90%.

In some embodiments, the pharmaceutical composition is suitable for oral, mucosal, rectal, subcutaneous, intravenous, intramuscular, intranasal, inhaled, or transdermal administration. In some embodiments, the pharmaceutical composition is suitable for oral administration and is formulated as a tablet or a capsule.

In some embodiments, the pharmaceutical compositions further comprise a therapeutically effective amount of an additional active compound. In some embodiments, the additional active compound is an oxytocin-releasing agent. In some embodiments, the oxytocin-releasing agent is any of a melanocortin (MC) receptor agonist, a melanocyte stimulating hormone, a-melanocortin, a-melanotropin, melanotan II (MT-11), bremelanotide, a $5\text{-HT}_{1A}$ agonist, a $5\text{-HT}_{2A}$ agonist, or a $5\text{-HT}_2C$ agonist, 6-(2-Aminopropyl)-2,3-dihydrobenzofuran (6-APDB), 6-(2-aminopropyl)benzofuran (6-APB), (4-fluoro-N-(2-{4-[(2S)-2-(hydroxymethyl)-2,3-dihydro-1,4-benzodioxin-5-yl]piperazin-1-yl}ethyl)benzamide (flesinoxan), 5-(3-[((2S)-1,4-benzodioxan-2-ylmethyl)amino]propoxy)-1,3-benzodioxole, (osemozotan), buspirone, gepirone, befiradol, eptapirone, 8-OH-DPAT, tandospirone, serotonin, ergine, ergotamine, lysergic acid, lysergic acid diethylamide (LSD), psilocybin, 4-hydroxydimethyltryptamine, N,N-dimethyltryptamine (DMT), 5-methoxy-dimethyltryptamine (5-MeO-DMT), mescaline, an entactogen, 4-bromo-2,5-dimethoxyphenethylamine, 3,4-methylenedioxyamphetamine (MDA), methylenedioxyethylamphetamine (MDEA), 3-methoxy-4,5-methylenedioxyamphetamine (MMDA), racemic 3,4-methylenedioxymethamphetamine, tenamfetamine, lorcaserin, or an analog, derivative, prodrug, or salt thereof.

In some embodiments, the additional active compound is a supplement. In some embodiments, the supplement is any of alpha lipoic acid (ALA), magnesium, vitamin C, ascorbate, grape seed extract, grapefruit juice, acetyl-L-carnitine (ALCAR), green tea extract, 5-HTP, melatonin, and CoQ10.

In some embodiments, the additional active compound is selected from the group consisting of: oxytocin, amino acids, antioxidants, anti-inflammatory agents, analgesics, antineuropathic and antinociceptive agents, antimigraine agents, anxiolytics, antidepressants, antipsychotics, anti-PTSD agents, immunostimulants, anti-cancer agents, antiemetics, orexigenics, antiulcer agents, antihistamines, antihypertensives, anticonvulsants, antiepileptics, bronchodilators, neuroprotectants, entactogens and empathogens, entheogens, psychedelics, phenethylamines, tryptamines, serotonergic agents, monoamine oxidase inhibitors, sedatives, stimulants, and vitamins.

In some embodiments, the psychedelic is any of psilocybin, psilocin, DMT, 5-MeO-DMT, mescaline, salvinorin A, THC, 4-Aco-DMT, 5-Br-DMT, 5-Cl-DMT, 5-F-DMT, PRO-LAD, ETH-LAD, AL-LAD, 1P-LSD, DiPT, 2C-B, and 2C-C. In some embodiments, the entactogen is any of 4-MTA, MDAI, 5-methyl-MDA, 5-APB, or 6-APB, DiFMDA, MBDB, BDB, MDA, and MDEA.

In some embodiments, the additional active compound increases therapeutic efficacy, provides additional therapeutic effects, decreases unwanted effects, improves a physiological or psychological effect, reduces or prevents neurotoxicity, increases stability or shelf-life, improves bioavailability, induces a synergistic effect, or alters pharmacokinetics or pharmacodynamics. In some embodiments, the synergistic effect is a greater than additive increase in potency, bioactivity, bioaccessibility, bioavailability, or therapeutic effect.

In some embodiments, the metabolism of the non-racemic mixture by at least one polymorphically-expressed cytochrome P450 isoform is reduced relative to metabolism of racemic MDMA, as determined by an in vitro assay. In some embodiments, the cytochrome P450 isoform is CYP2C19 and/or CYP2D6.

In some embodiments, the pharmaceutical compositions further comprises a pharmaceutically acceptable carrier, diluent, or excipient.

In some aspects provided herein are unit dosage forms comprising any of the described pharmaceutical compositions. In some embodiments, the unit dosage form is an immediate release, controlled release, sustained release, extended release, delayed release, or modified release formulation.

In some aspects provided herein are methods of modulating neurotransmission in a subject. In some embodiments, the method comprises administering to the subject a therapeutically effective amount of any of the described non-racemic mixtures, any of the described pharmaceutical compositions, or any of the described unit dosage forms. In some embodiments, the method treats a mental health disorder. In some embodiments, any of the described non-racemic mixtures, pharmaceutical compositions, or unit dosage forms is administered in combination with one or more psychotherapy sessions.

In some aspects, provided herein are methods of modulating neurotransmission in a subject, comprising administering to the subject a non-racemic mixture of R-MDMA and S-MDMA, including pharmaceutically acceptable salts thereof, wherein the non-racemic mixture comprises R-MDMA in enantiomeric excess.

In some embodiments, the neurotransmission is one or more of serotonergic neurotransmission, dopaminergic neurotransmission, and noradrenergic neurotransmission. In some embodiments, the serotonergic neurotransmission comprises agonizing $5\text{-HT}_{2A}$ and/or binding to SERT, thereby increasing levels of serotonin in the CNS, and wherein serotonergic neurotransmission is increased relative to that of R-MDMA. In some embodiments, the non-racemic mixture has reduced affinity for DAT and/or NET, as compared to racemic MDMA. In some embodiments, reduced affinity for DAT and/or NET reduces abuse potential relative to racemic MDMA.

In some embodiments, modulating neurotransmission comprises agonizing an alpha-4 beta-2 nicotinic receptor (α4β2 nAChR). In some embodiments, the mixture has greater potency at α4β2 nAChR relative to R-MDMA and/or comparable potency to racemic MDMA. In some embodiments, the mixture has a reduced half-life relative to R-MDMA and/or racemic MDMA. In some embodiments, the milligram amount of the mixture is equal to or greater than that of R-MDMA and/or racemic MDMA. In some embodiments, racemic MDMA is administered in two doses comprising an initial dose and a subsequent dose.

In some embodiments, the administering does not cause hyperthermia in the subject. In some embodiments, administering does not increase the subject's body temperature or does not increase the subject's body temperature by more than 0.1° C., 0.2° C., or 0.3° C.

In some embodiments, the method treats a mental disorder in the subject. In some embodiments, the mental health disorder is selected from the group consisting of: depression, major depressive disorder (MDD), treatment-resistant depression (TRD), atypical depression, postpartum depression, catatonic depression, a depressive disorder due to a medical condition, premenstrual dysphoric disorder, seasonal affective disorder, dysthymia, anxiety and phobia disorders, generalized anxiety disorder, agoraphobia, panic disorder, separation anxiety disorder, social anxiety disorder, post-traumatic stress disorder, adjustment disorders, feeding and eating disorders, including binge eating, bulimia, and anorexia nervosa, other binge behaviors, body dysmorphic syndromes, drug abuse or dependence disorders, disruptive behavior disorders, impulse control disorders, gaming disorders, gambling disorders, memory loss, dementia of aging, attention deficit hyperactivity disorder, personality disorders, including antisocial, avoidant, borderline, histrionic, narcissistic, obsessive compulsive, paranoid, schizoid and schizotypal personality disorders, attachment disorders, autism, social anxiety in autistic subject, and dissociative disorders.

In some embodiments, the method treats a stress disorder, acute stress disorder, brief psychotic disorder with marked stressor(s), delirium, mild cognitive impairment (MCI), dementia, psychosis, psychotic major depression, autism, and psychological distress related to life-threatening illness or death in the subject.

In some embodiments, the method treats a substance abuse disorder in the subject. In some embodiments, the substance abuse disorder is selected from the group consisting of alcohol use disorder, opioid use disorder, nicotine dependence and tobacco use disorder, sedative, hypnotic, and anxiolytic use disorder, and stimulant use disorder.

In some embodiments, the subject is in long-term or institutional care. In some embodiments, the non-racemic mixture is administered in combination with one or more psychotherapy sessions.

In some embodiments, the non-racemic mixture for administering comprises R-MDMA in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the non-racemic mixture for administering comprises R-MDMA in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the non-racemic mixture for administering comprises R-MDMA in enantiomeric excess of about 10%, 15%, 20%, 25%, 30%, 35%, 40%, 45%, 50%, 55%, 60%, 65%, 70%, 75%, 80%, 85%, 90%, or 95%.

In some embodiments, the non-racemic mixture for administering comprises R-MDMA and S-MDMA in a ratio of about 6:1 to 12:1, 7:1 to 11:1, or 8:1 to 10:1. In some embodiments, the non-racemic mixture for administering comprises R-MDMA and S-MDMA in a ratio of about 6:1, 7:1, 8:1, 9:1, 10:1, 11:1, or 12:1. In some embodiments, the non-racemic mixture for administering comprises R-MDMA and S-MDMA in a ratio of 9:1. In some embodiments, the non-racemic mixture for administering comprises R-MDMA in enantiomeric excess of within 0.05% of 90%, or within 0.1% of 90%.

In some aspects provided herein are methods of treating a disorder in a subject. A method of treating a disorder in a subject, comprising administering to the subject a therapeutically effective amount of a non-racemic mixture of R-MDMA and S-MDMA, wherein the non-racemic mixture comprises R-MDMA in enantiomeric excess.

In some embodiments, the non-racemic mixture for treating a disorder comprises R-MDMA in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the non-racemic mixture for treating a disorder comprises R-MDMA in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the non-racemic mixture for treating a disorder comprises R-MDMA in enantiomeric excess of about 10%, 15%, 20%, 25%, 30%, 35%, 40%, 45%, 50%, 55%, 60%, 65%, 70%, 75%, 80%, 85%, 90%, or 95%.

In some embodiments, the non-racemic mixture for treating a disorder comprises R-MDMA and S-MDMA in a ratio of about 6:1 to 12:1, 7:1 to 11:1, or 8:1 to 10:1. In some embodiments, the non-racemic mixture for treating a disorder comprises R-MDMA and S-MDMA in a ratio of about 6:1, 7:1, 8:1, 9:1, 10:1, 11:1, or 12:1. In some embodiments, the non-racemic mixture for treating a disorder comprises R-MDMA and S-MDMA in a ratio of 9:1. In some embodiments, the non-racemic mixture for treating a disorder comprises R-MDMA in enantiomeric excess of within 0.05% of 90%, or within 0.1% of 90%.

In some embodiments, the disorder is a mental health disorder. In some embodiments, the mental health disorder is selected from the group consisting of: depression, major depressive disorder (MDD), treatment-resistant depression (TRD), atypical depression, postpartum depression, catatonic depression, a depressive disorder due to a medical condition, premenstrual dysphoric disorder, seasonal affective disorder, dysthymia, anxiety and phobia disorders, generalized anxiety disorder, agoraphobia, panic disorder, separation anxiety disorder, social anxiety disorder, post-traumatic stress disorder, adjustment disorders, feeding and eating disorders, including binge eating, bulimia, and anorexia nervosa, other binge behaviors, body dysmorphic syndromes, drug abuse or dependence disorders, disruptive behavior disorders, impulse control disorders, gaming disorders, gambling disorders, memory loss, dementia of aging, attention deficit hyperactivity disorder, personality disorders, including antisocial, avoidant, borderline, histrionic, narcissistic, obsessive compulsive, paranoid, schizoid and schizotypal personality disorders, attachment disorders, autism, social anxiety in autistic subject, and dissociative disorders.

In some embodiments, the disorder is a substance abuse disorder. In some embodiments, the substance abuse disorder is selected from the group consisting of alcohol use disorder, opioid use disorder, nicotine dependence and tobacco use disorder, a sedative, hypnotic, and anxiolytic use disorder, and a stimulant use disorder.

In some embodiments, the non-racemic mixture is administered in combination with one or more psychotherapy sessions. In some embodiments, the subject has a genetic variation associated with a mental health disorder, trauma or stressor related disorder, depression, or anxiety, and including a genetic variation in mGluR5 or FKBP5.

In some embodiments, the method does not cause neurotoxicity, or results in reduced neurotoxic effects. In some embodiments, an absence or reduction of neurotoxic effect is determined by tests and procedures that are in silico, in vitro, or in vivo. In some embodiments, the absence or reduction of neurotoxic effect is determined by computer analysis or simulation; by biochemical assays or tissue culture; by behavioral assessment, functional observational batteries, tests of motor activity, tests of schedule-controlled operant behavior, tests of neurological function, tests of neurophysiological function, tests of nerve-conduction, tests of evoked-potential, neurochemical measures, neuroendocrine measures, neuropathological measures, EEG, or imaging. In some embodiments, the neurotoxic effect is determined by measuring one or more of: a) at least one toxic metabolite of MDMA; b) oxidative stress and dopamine-based quinones; c) mitochondrial dysfunction; and d) activation of glial cells.

In some embodiments, the reduction of a neurotoxic effect is at least a 5% reduction, at least a 10% reduction, at least a 15% reduction, at least a 25% reduction, at least a 50% reduction, at least a 75% reduction, at least a 90% reduction, or at least a 95% reduction, or at least a 99% reduction, relative to racemic MDMA.

In some embodiments, the mental health disorder is PTSD. In some embodiments, one or more symptoms of PTSD are reduced and/or a PTSD diagnosis is reversed, as determined by the Clinician-Administered PTSD Scale for DSM-5 (CAPS-5). In some embodiments, the one or more symptoms of PTSD include any of flashbacks, nightmares, distressing and intense memories, distress or physical reactions after being exposed to triggers, blaming self or others for the trauma, decreased interest in things that were once enjoyable, negative feelings about self and the world, inability to remember the trauma clearly, difficulty feeling positive, feelings of isolation, negative affect, difficulty feeling positive, avoidance, aggression or irritability, hypervigilance and hyper-awareness, difficulty concentrating, difficulty sleeping, heightened startle response, engaging in self-destructive, or risky behavior, difficulty sleeping or staying asleep, or suicidal ideation.

In some embodiments, the method comprises administering the non-racemic mixture to the subject once a week, once every two weeks, once every three weeks, or once a month. In some embodiments, the method comprises administering the non-racemic mixture to the subject once every three weeks. In some embodiments, the method comprises administering a single dose of the non-racemic mixture. In some embodiments, the method comprises administering a single dose of the non-racemic mixture in an amount of 50 mg to 300 mg, 100 mg to 300 mg, 150 mg to 300 mg, 200 mg to 300 mg, or 200 mg to 250 mg. In some embodiments, the method comprises administering a single dose of the non-racemic mixture in an amount of about 62 mg, 141 mg, 235 mg, or 285 mg. In some embodiments, the method comprises orally administering the non-racemic mixture. In some embodiments, the method comprises administering the non-racemic mixture in combination with psychotherapy.

In some aspects, provided herein are methods for preparing any of the described non-racemic mixtures. In some embodiments, a method for preparing a non-racemic mixture comprising R-MDMA and S-MDMA, includes the steps of preparing chiral sulfinamides from 3,4-di-benzyloxybenzaldehyde, enantioselectively synthesizing R-MDMA and S-MDMA from the chiral sulfinamides; and recrystallizing R-MDMA and S-MDMA in a ratio, wherein R-MDMA predominates in the ratio. In some embodiments, a non-racemic mixture prepared according to the provided methods comprises R-MDMA and S-MDMA in a ratio of about 6:1 to 12:1, 7:1 to 11:1, or 8:1 to 10:1. In some embodiments, a non-racemic mixture prepared according to the provided methods comprises R-MDMA and S-MDMA in a ratio of about 6:1, 7:1, 8:1, 9:1, 10:1, 11:1, or 12:1. In some embodiments, a non-racemic mixture prepared according to the provided methods comprises R-MDMA and S-MDMA in a ratio of 9:1. In some embodiments, a non-racemic mixture prepared according to the provided methods comprises R-MDMA in enantiomeric excess of within 0.05% of 90%, or within 0.1% of 90%.

The foregoing has outlined broadly some pertinent features of certain exemplary embodiments of the present disclosure so that the detailed description of the invention that follows may be better understood and so that the present contribution to the art can be more fully appreciated. Additional features of the invention will be described hereinafter which form the subject of the claims of the invention. It should be appreciated by those skilled in the art that the conception and the disclosed specific formulations and methods may be readily utilized as a basis for modifying or designing other formulations and methods for carrying out the same purposes of the disclosure. It should be also realized that such equivalent formulations and methods do not depart from the spirit and scope of the invention as set forth in the claims. Hence, this summary is made with the understanding that it will be considered as a brief and general synopsis of only some of the objects and embodiments herein, is provided solely for the benefit and convenience of the reader, and is not intended to limit in any manner the scope, or range of equivalents, to which the claims are lawfully entitled.

BRIEF SUMMARY OF THE FIGURES

To further clarify various aspects of the invention, a more particular description is rendered by reference to certain exemplary embodiments illustrated in the figures. It will be appreciated that these figures depict only illustrated embodiments of the invention and should not be considered limiting of its scope. They are merely provided as exemplary illustrations of certain concepts of some embodiments of the invention. Certain aspects of the invention are therefore further described and explained with additional specificity and detail, but still by way of example only, with reference to the accompanying figures in which.

DETAILED DESCRIPTION OF THE INVENTION

Figure 1:
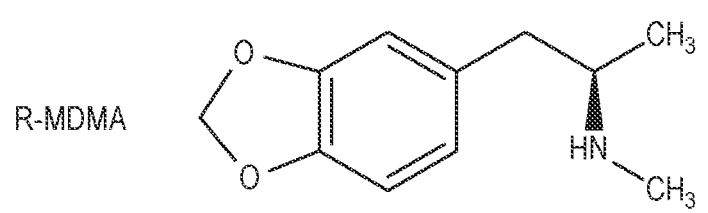
FIG. 1 shows the structures of the R-(−) enantiomer of 3,4-methylenedioxymethamphetamine (R-MDMA) and the S-(+) enantiomer of 3,4-methylenedioxymethamphetamine (S-MDMA).
Figure 1:
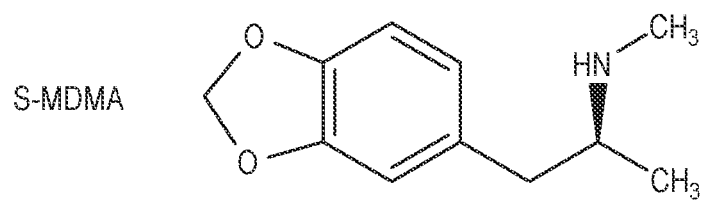
Figure 2:
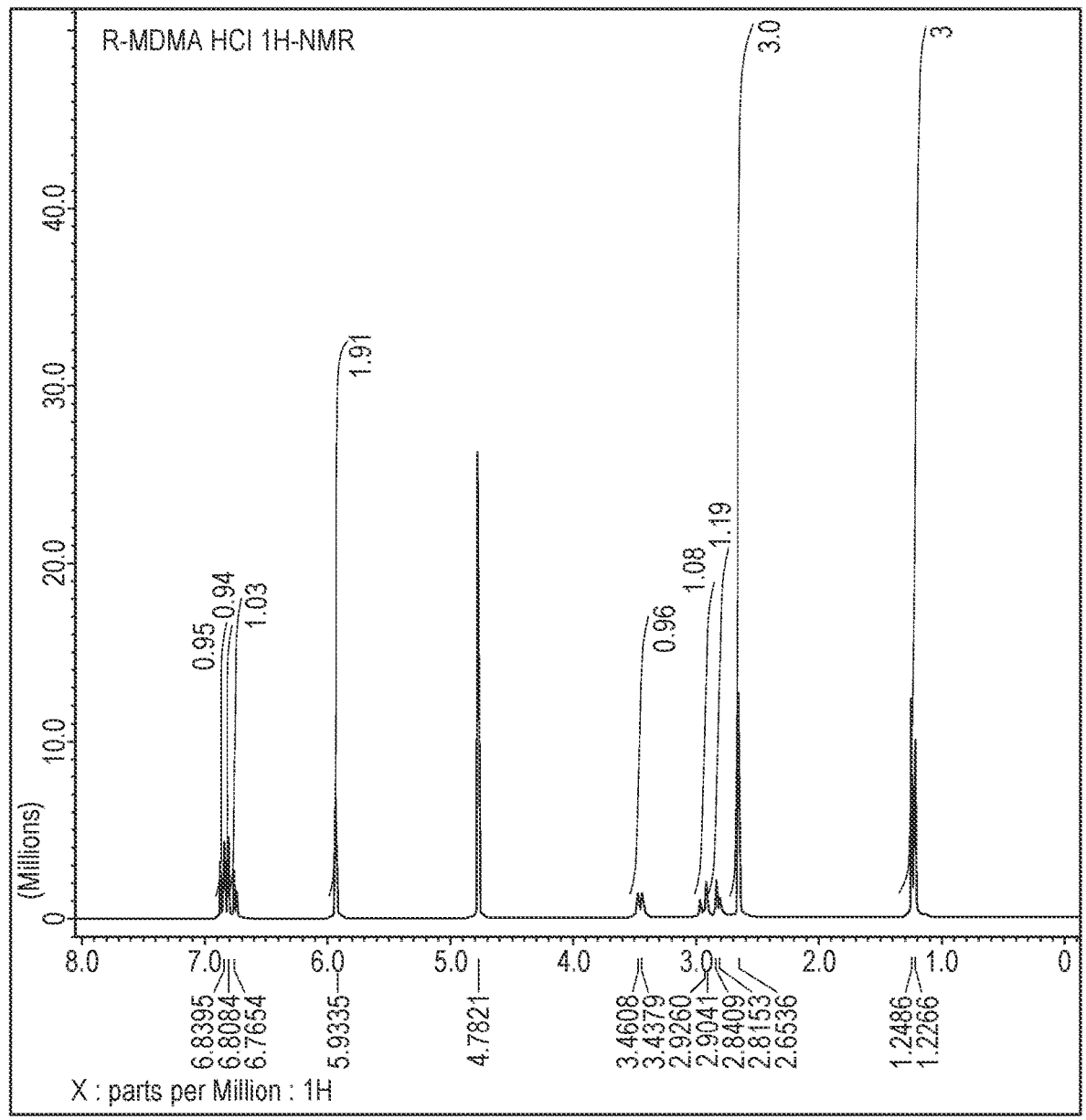
FIG. 2 shows 1H-NMR characterization of R-MDMA HCl.
Figure 3:
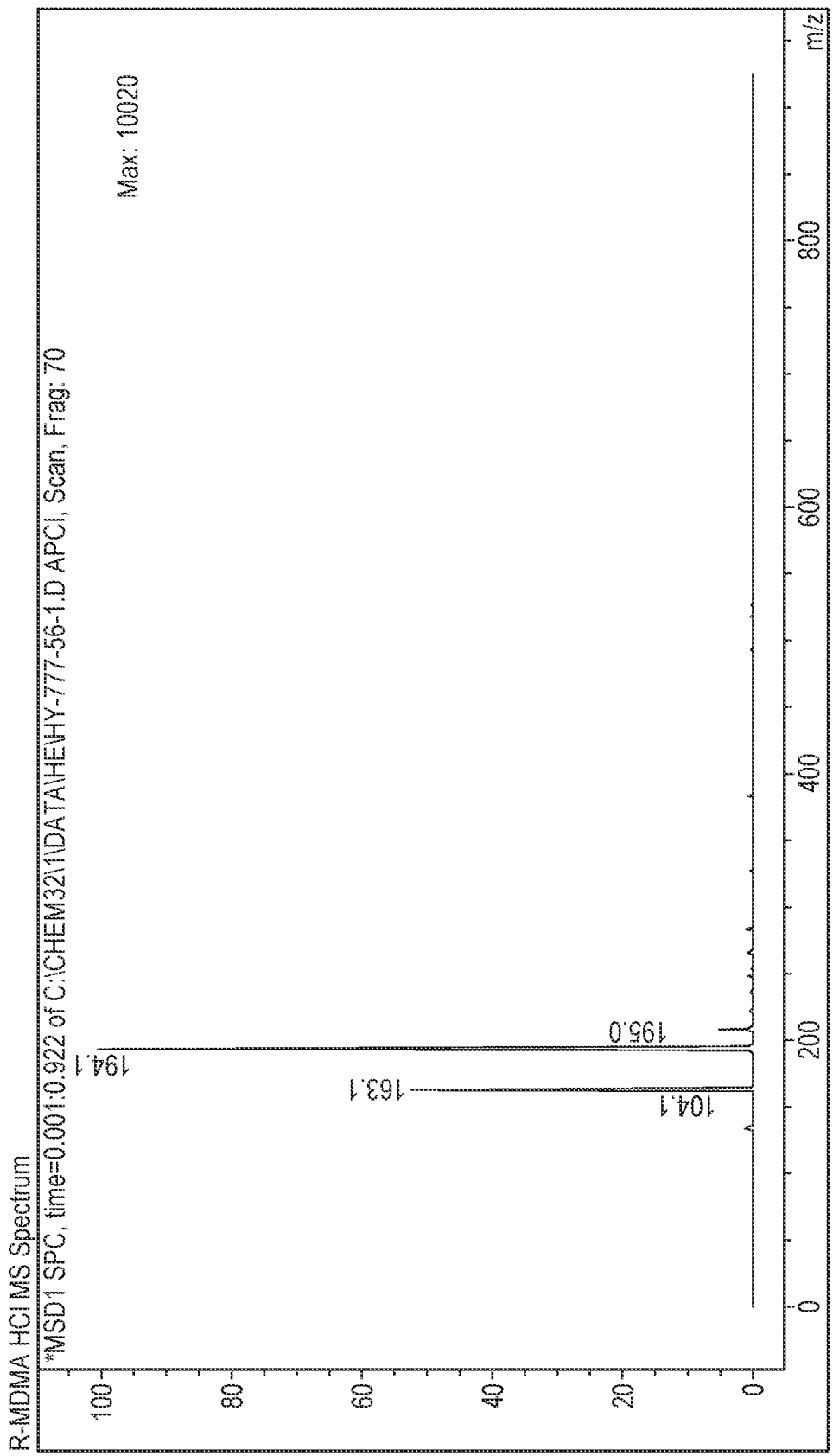
FIG. 3 shows atmospheric pressure chemical ionization mass spectrometry (MS) characterization of R-MDMA HCl.
Figure 4:
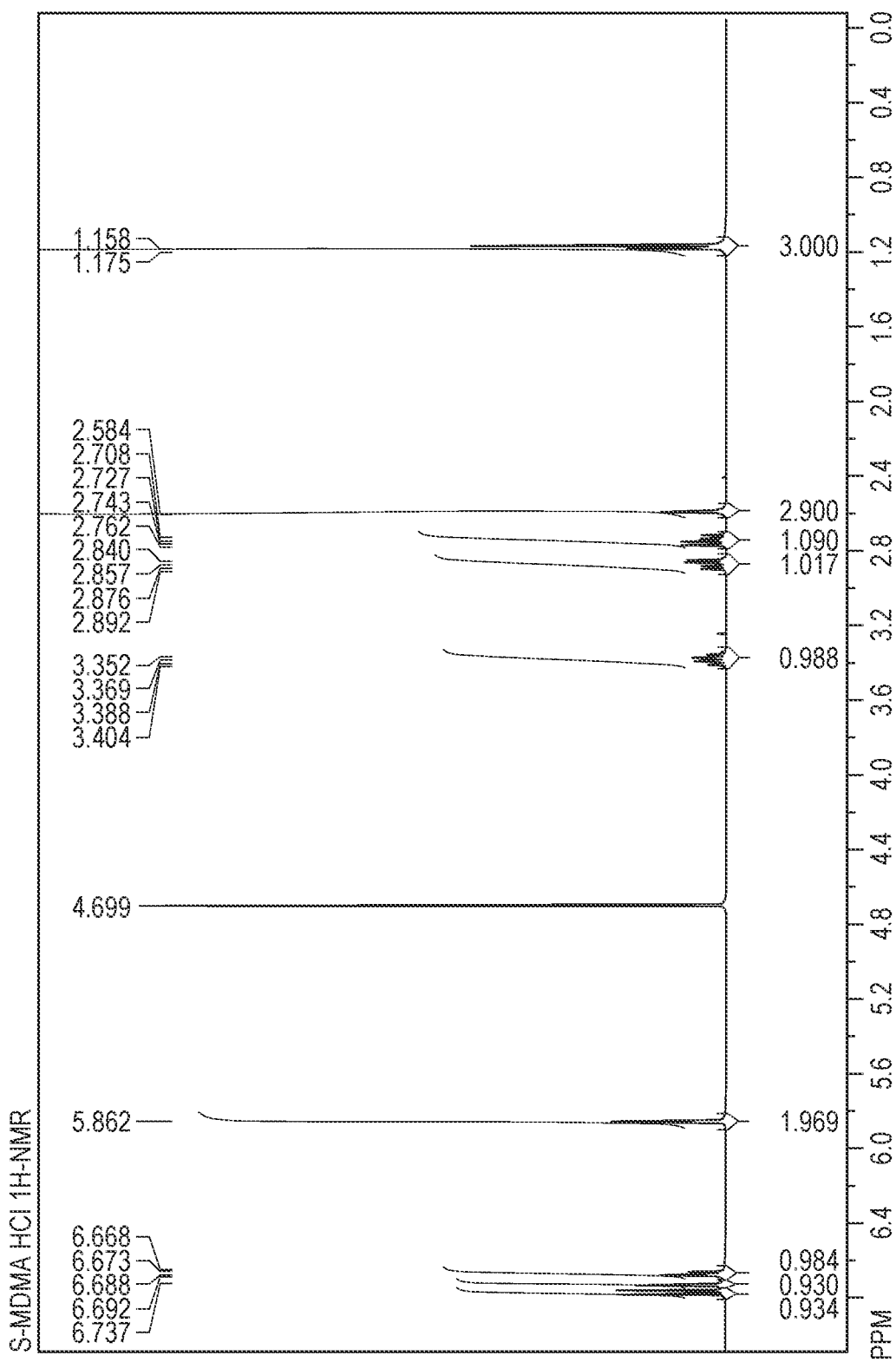
FIG. 4 shows 1H-NMR characterization of S-MDMA HCl.
Figure 5:
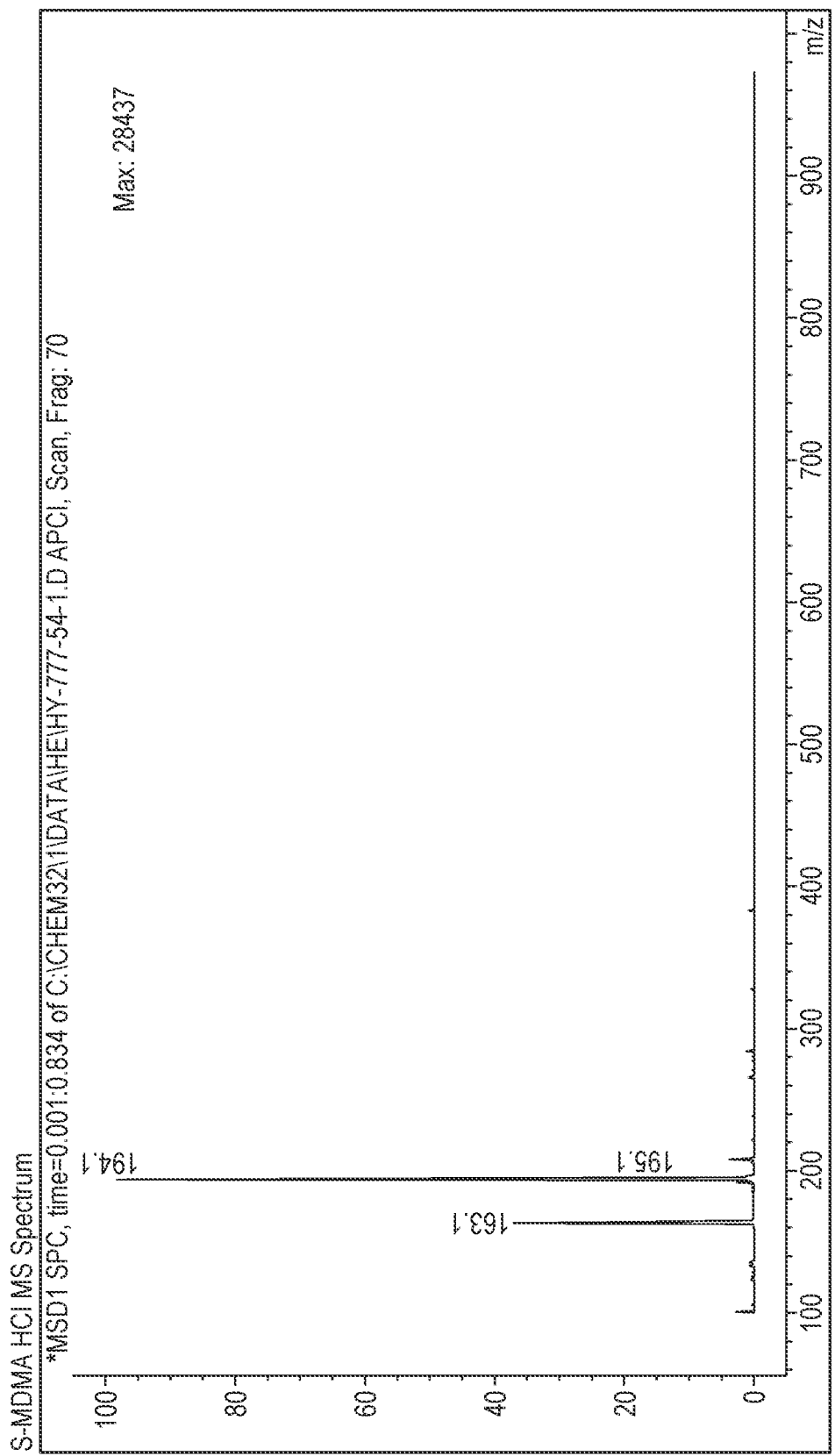
FIG. 5 shows atmospheric pressure chemical ionization MS of S-MDMA HCl.

While various aspects and features of certain embodiments are summarized above, the following detailed description illustrates several exemplary embodiments in further detail to enable one having ordinary skill in the art to which the invention belongs ("one of skill") to practice such embodiments, and to make and use the full scope of the invention claimed.

It will be understood that many modifications, substitutions, changes, and variations in the described examples, embodiments, applications, and details of the invention illustrated herein can be made by those skilled in the art without departing from the spirit of the invention, or the scope of the invention as described in the appended claims, and the general principles defined herein may be applied to a wide range of aspects. Thus, the invention is not intended to be limited to the aspects presented, but is to be accorded the widest scope consistent with the principles and novel features disclosed. The description below is designed to make such embodiments apparent to a person of ordinary skill, in that the embodiments shall be both readily cognizable and readily creatable without undue experimentation, solely using the teachings herein together with general knowledge of the art.

While the methods described and illustrated herein may include particular steps, it should be apparent that other methods including fewer, more, or different steps than those described and shown are also within the spirit and scope of the invention. The described methods and uses of discussed and associated steps shown herein therefore should be understood as being provided for purposes of illustration, not limitation. It should be further understood that the specific order or hierarchy of steps in the methods and uses disclosed are only exemplary approaches.

A. Compounds and Uses

In some aspects, provided herein are enantiomers and non-racemic mixtures of MDMA, such as enantiomerically enriched mixtures of R-MDMA and S-MDMA. In some embodiments, the provided enantiomerically enriched mixtures comprise R-MDMA in enantiomeric excess. In some embodiments, the enantiomeric mixtures display improved properties, such as a reduced duration of action, an improved safety profile, and reduced drug tolerance, thereby facilitating treatment accessibility and adoption.

The racemic form of the entactogen MDMA has been studied for its potential to accelerate progress in psychotherapy (Feduccia et al., Frontiers in Psychiatry, 2019; 10:650; Sessa, Higbed, and Nutt, Frontiers in Psychiatry 2019; 10:138). MDMA produces empathy and bonding, allowing patients to access and process memories of emotional trauma (Hysek et. al., Soc Cogn Affect Neurosci., 2014; 9(11):1645-52). The drug has proven clinical efficacy in reducing the severity of post-traumatic stress disorder (PTSD) and even reversing a diagnosis, as determined by CAPS-IV PTSD diagnostic criteria (Mithoefer et al., Psychopharmacology (Berl), 2019; 236(9):2735-2745; Mitchell et al., Nat Med., 2021; 27(6):1025-1033). However, while racemic MDMA has therapeutic potential, it causes a number of side effects that make it contraindicated for some patients. See, e.g., Kalant, CMAJ, 2001; 165(7), 917-928; Carvalho et al., Curr Pharm Biotechnol. 2010; 11(5):476-95.

The relative effects of MDMA enantiomers have been investigated since the 1980s, and studies generally indicate greater potency of S-MDMA relative to R-MDMA. See, e.g., Johnson et al., European J Pharmacol, 1986; 132 (2-3):269-276; Steele et al., Biochemical Pharmacol, 1987; 36(14), 2297-2303; Oberlander & Nichols, Psychopharmacol, 1988; 95 (1)). In vitro studies of HEK-293 cells stably expressing human serotonin, dopamine and norepinephrine transporters (SERT, DAT, and NET) showed greater potency of S-MDMA than R-MDMA at the three transporters, consistent with the higher potency of the S(+)-isomer in human (Verrico et al., Psychopharmacol (Berl), 2007; 189(4):489-503). In comparison to racemic and S-MDMA, R-MDMA has been shown to drive entactogenic effects without contributing to markers of neurotoxicity (Curry et al., Neuropharmacol, 2018; 128, 196-206; Pitts et al., Psychopharmacol, 2018; 235(2), 377-392).

Each of the individual isomers of MDMA possess favorable pharmacological properties for the intended treatment of PTSD, however observed tolerability issues at high doses show some evidence of toxicity, primarily associated with S(+)-MDMA. There is therefore a need for additional pharmacologic agents that have similar entactogen-like effects while having improved pharmacological and safety profiles compared to MDMA, and in particular reduced neurotoxicity. Provided herein are non-racemic enantiomeric mixtures that balance the contributions of R-MDMA and S-MDMA to meet such needs. Such agents, as well as compositions and formulations comprising them and methods of their use, are disclosed herein. Among the various aspects of the present invention are enantiomeric entactogen compounds, and compositions and formulations thereof, as well as methods of using them to treat mental health disorders, for example mood disorders and PTSD. In some embodiments, the therapeutic potential of MDMA is enhanced by lowering the ratio of the S-enantiomer from a 5:5 racemic ratio to a ratio wherein the R enantiomer predominates, such as a 9:1 non-racemic R:S ratio.

a. Compounds

"Compounds" refers to the compounds encompassed by any structural formulae disclosed herein, and includes any specific compounds within these formulae whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers, or diastereomers. Accordingly, the chemical structures depicted herein encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. See, e.g., Lourenço et al., J Pharm Biomed Anal., 2013; 73:13-7 and Rasmussen et al., J Chromatogr B Analyt Technol Biomed Life Sci., 2006; 842(2):136-41.

An enantiomer that is isolated is one that is substantially free of the corresponding enantiomer. Thus, an isolated enantiomer refers to a compound that is separated via separation techniques or prepared free of the corresponding enantiomer. The term "substantially free," as used herein, means that the compound is made up of a significantly greater proportion of one enantiomer. In preferred embodiments, the compound includes at least about 90% by weight of a preferred enantiomer. In other embodiments, the compound includes at least about 99% by weight of a preferred enantiomer. Preferred enantiomers can be isolated from racemic mixtures by any method known to those skilled in the art, including high performance liquid chromatography (HPLC) and the formation and crystallization of chiral salts, or preferred enantiomers can be prepared by methods described herein.

"MDMA" refers to 3,4-methylenedioxymethamphetamine, i.e., 3,4-MDMA, 1-(1,3-benzodioxol-5-yl)N-methylpropan-2-amine (IUPAC), formula $C_{11}H_{15}NO_2$, m.w. 193.25 g/mol, whether in ion, freebase, or salt form, including polymorphs, as well as its isomers. Therefore "MDMA" as used herein will be understood to encompass the salt forms of MDMA, such as MDMA hydrochloride salt. 3,4-MDMA HCl is commercially available from, e.g., Cayman Chemical Co., Ann Arbor, MI, with purity 98%, Item No. 13971, NSC 168383, CAS No. 64057-70-1; and Lipomed AG, Arlesheim, Switzerland, as Prod. Ref No. MDM-94-HC, DEA No. 7405 CI, and available as MDM-94-HC-ILM [1.0 mg base/1 ml solution in methanol], and MDM-94-HC-10, -50, and -100 [10, 50, and 100 mg powder racemic MDMA HCl].

MDMA will be appreciated as including the drug substance MDMA as a racemic mixture, i.e., S,R(+/−)-3,4-methylenedioxymethamphetamine (S,R-MDMA), as an enantiomerically enriched mixture (of whatever proportions), or as individual enantiomers (i.e., pure or substantially pure R-MDMA or S-MDMA). Both enantiomers function as monoamine releasers (Hiramatsu and Cho, Neuropharmacology, 1990; 29:269-75; Johnson et al., Eur. J Pharmacol, 1986; 132:269-276; Setola et al., Mol. Pharmacol., 2003; 63:1223-1229), with S-MDMA being the more potent of the two and generally considered the "active isomer" (Anderson et al., NIDA Res. Monogr., 1978; 8-15) (both cited in Curry et al., Neuropharmacology, 2018; 128: 196-206). Herein, when referring generically to "MDMA" it will be understood to mean racemic MDMA, unless context demands otherwise.

The present disclosure also includes stereoisomers of the compounds described herein, where applicable, either individually or admixed in any proportions. Stereoisomers may include enantiomers, diastereomers, racemic mixtures, and combinations thereof. Such stereoisomers can be prepared and separated using conventional techniques, either by reacting enantiomeric starting materials, or by separating isomers of compounds disclosed herein. Isomers may include geometric isomers. Examples of geometric isomers include cis isomers or trans isomers across a double bond. Other isomers are contemplated among the compounds of the present disclosure. The isomers may be used either in pure form or in admixture with other isomers of the compounds described herein.

Various methods are known in the art to obtain optical isomers of compounds. Examples of such methods include the following: I. Physical separation of crystals whereby macroscopic crystals of the individual enantiomers are manually separated. This technique may particularly be used if crystals of the separate enantiomers exist (i.e., the material is a conglomerate), and the crystals are visually distinct; II. Simultaneous crystallization whereby the individual enantiomers are separately crystallized from a solution of the racemate, possible only if the latter is a conglomerate in the solid state; III. Enzymatic resolutions whereby partial or complete separation of a racemate by virtue of differing rates of reaction for the enantiomers with an enzyme; IV. Enzymatic asymmetric synthesis, a synthetic technique whereby at least one step of the synthesis uses an enzymatic reaction to obtain an enantiomerically pure or enriched synthetic precursor of the desired enantiomer; V. Chemical asymmetric synthesis whereby the desired enantiomer is synthesized from an achiral precursor under conditions that produce asymmetry (i.e., chirality) in the product, which may be achieved using chiral catalysts or chiral auxiliaries; VI. Diastereomer separations whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer; VII. First- and second-order asymmetric transformations whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomers; VIII. Kinetic resolutions comprising partial or complete resolution of a racemate (or of a further resolution of a partially resolved compound) by virtue of unequal reaction rates of the enantiomers with a chiral, non-racemic reagent or catalyst under kinetic conditions; IX. Enantiospecific synthesis from non-racemic precursors whereby the desired enantiomer is obtained from non-chiral starting materials and where the stereochemical integrity is not or is only minimally compromised over the course of the synthesis; X. Chiral liquid chromatography whereby the enantiomers of a racemate are separated in a liquid mobile phase by virtue of their differing interactions with a stationary phase. The stationary phase can be made of chiral material or the mobile phase can contain an additional chiral material to provoke the differing interactions; XI. Chiral gas chromatography whereby the racemate is volatilized and enantiomers are separated by virtue of their differing interactions in the gaseous mobile phase with a column containing a fixed non-racemic chiral adsorbent phase; XII. Extraction with chiral solvents whereby the enantiomers are separated by virtue of preferential dissolution of one enantiomer into a particular chiral solvent; and XIII. Transport across chiral membranes whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane, which allows only one enantiomer of the racemate to pass through.

b. MDMA Enantiomers

In some aspects, provided herein are enantiomers of MDMA, such as R-MDMA and S-MDMA. FIG. 1 shows the structures of R-MDMA ((R)-1-(1,3-Benzodioxol-5-yl)-N-methyl-propan-2-amine; IUPAC: ($\alpha$R)-N,$\alpha$-dimethyl-1,3-benzodioxole-5-ethanamine, monohydrochloride; CAS No: 69558-31-2) and S-MDMA ((S)-1-(1,3-Benzodioxol-5-yl)-N-methylpropan-2-amine; IUPAC: ($\alpha$S)-N,$\alpha$-dimethyl-1,3-benzodioxole-5-ethanamine, monohydrochloride; CAS No: 66142-89-0). In other aspects, provided herein are non-racemic mixtures of MDMA enantiomers. In some embodiments, non-racemic mixtures of MDMA comprise enantiomerically enriched mixtures of MDMA enantiomers. A "non-racemic mixture" refers to a non-racemic enantiomeric mixture wherein the amount of each chiral molecule is not equal. Such mixtures may be referred to herein simply as an "enantiomeric mixture." In some embodiments, the non-racemic mixtures of MDMA comprise R-MDMA in enantiomeric excess. In some embodiments, the non-racemic mixtures of MDMA comprise S-MDMA in enantiomeric excess.

Different naming conventions can be used to describe enantiomers. According to the R/S system, R and S refer to the absolute configuration possessed by the chiral center. Enantiomers can also be described according to the direction that a solution of the molecule rotates plane-polarized light, anticlockwise or clockwise. Levorotary, or "L," "l," or "(−)," refers to an enantiomer that rotates plane polarized light in a left-handed, anticlockwise direction, also described contraclockwise or counterclockwise. Dextrorotatory, or "D," "d," or "(+)," refers to an enantiomer that rotates plane polarized light in a right-handed, clockwise direction. "R-MDMA" refers to the levorotatory R(−) enantiomer of 3,4-MDMA, bearing the IUPAC name (R)-1-(1,3-Benzodioxol-5-yl)-N-methylpropan-2-amine. R-MDMA may be referred to herein as "(−)-MDMA" or "(R)-(−)-3,4-MDMA." An "R-MDMA salt" refers to any pharmaceutically acceptable salt form of R-MDMA, and will be understood to include its hydrochloride, sulfate, tartrate, sodium, acetate, phosphate, chloride, and potassium salts. "S-MDMA" refers to the dextrorotary S(+) enantiomer of 3,4-MDMA, bearing the IUPAC name (S)-1-(1,3-Benzodioxol-5-yl)-N-methylpropan-2-amine. S-MDMA may be referred to herein as "(+)-MDMA" or "(S)-(+)-3,4-MDMA." An "S-MDMA salt" refers to any pharmaceutically acceptable salt form of R-MDMA, and will be understood to include its hydrochloride, sulfate, tartrate, sodium, acetate, phosphate, chloride, and potassium salts.

In some embodiments, a compound of the invention may be provided in an enantiomerically enriched composition, such as a mixture of enantiomers. In some embodiments, the enantiomerically enriched composition comprises an enantiomer present in enantiomeric excess of at least 75%, at least 80%, at least 85%, at least 90%, at least 95%, at least 98%, at least 99%, at least 99.5%, or at least 99.9%, up to and including 100%. In some embodiments, the compound is MDMA. In some embodiments, the enantiomer is R-MDMA. In some embodiments, the enantiomer is S-MDMA.

In some aspects, provided herein are non-racemic enantiomeric mixtures comprising the (R)-enantiomer and (S)-enantiomer of MDMA, such as R-MDMA and S-MDMA. In some embodiments, the provided compositions comprise R-MDMA in enantiomeric excess (ee). In some embodiments, a provided non-racemic mixture comprises 90% or less of R-MDMA and 10% or more of S-MDMA. In some embodiments, the mixture comprises R-MDMA and S-MDMA in a ratio of 6:1 to 12:1, 7:1 to 11:1, or 8:1 to 10:1. In some embodiments, the mixture comprises R-MDMA and S-MDMA in a ratio of about 4:1, 5:1, 6:1, 7:1, 8:1, 9:1, 10:1, 11:1, or 12:1. In some embodiments, the mixture comprises R-MDMA and S-MDMA in a ratio of greater than 10:1, 11:1, 12:1, 13:1, 14:1, or 15:1 and including ranges in between. In some embodiments, the mixture comprises R-MDMA and S-MDMA in a ratio of about 7:1, 8:1, 9:1, or 10:1. In some embodiments, the mixture comprises R-MDMA and S-MDMA in a ratio of 9:1. It will be understood that the content of the provided ratios may also be represented as percentages, e.g., a 7:1 R:S ratio represents a mixture comprising 88% R-MDMA and 12% S-MDMA, a 8:1 R:S ratio represents a mixture comprising 89% R-MDMA and 11% S-MDMA, a 9:1 R:S ratio represents a mixture comprising 90% R-MDMA and 10% S-MDMA, a 10:1 R:S ratio represents a mixture comprising 91% R-MDMA and 9% S-MDMA.

In certain embodiments, a mixture of R-MDMA to S-MDMA of 9:1 (R:S) and 10:1 (R:S) are preferred. In some embodiments, a provided mixture or composition thereof comprises R-MDMA to S-MDMA in a ratio of 9:1. In some embodiments, a provided mixture or composition thereof comprises R-MDMA to S-MDMA in a ratio of 10:1. The provided ratios will be understood to refer either to weight by weight ratios or molar ratios, except in the case where a provided mixture comprises MDMA salts with different molecular weights. In all such embodiments, R-MDMA and S-MDMA will be understood to include the salts, polymorphs, prodrugs, and derivatives thereof.

In some embodiments, a provided non-racemic enantiomeric mixture of R-MDMA and S-MDMA comprises R-MDMA in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, a provided non-racemic enantiomeric mixture of R-MDMA and S-MDMA comprises R-MDMA in enantiomeric excess of 10%-95%, 20%-95%, 30%-95%, 40%-95%, 50%-95%, 55%-95%, 60%-90%, 65%-90%, 70%-85%, or 75%-85%, wherein each range is inclusive. In some embodiments, a non-racemic mixture of R-MDMA and S-MDMA comprises R-MDMA in enantiomeric excess of 10%, 15%, 20%, 25%, 30%, 35%, 40%, 45%, 50%, 55%, 60%, 65%, 70%, 75%, 80%, 85%, 90%, or 95%. In some embodiments, a non-racemic mixture of R-MDMA and S-MDMA comprises R-MDMA in enantiomeric excess of 75%, 76%, 77%, 78%, 79%, 80%, 81%, 82%, 83%, 84%, or 85%. In some embodiments, a non-racemic mixture of R-MDMA and S-MDMA comprises R-MDMA in enantiomeric excess of about 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1%. In some embodiments, a non-racemic mixture of R-MDMA and S-MDMA comprises R-MDMA in an enantiomeric excess of 79.5%, 79.6%, 79.7%, 79.8%, 79.9%, 80%, 80.1%, 80.2%, 80.3%, 80.4%, or 80.5%. In some embodiments, a non-racemic mixture of R-MDMA and S-MDMA comprises R-MDMA in an enantiomeric excess of 80%.

Enantiomeric excess (ee) refers to the excess of one enantiomer over another in a given mixture. EE can be determined from enantiomer concentration, such as in mol/Litre (M), and can range from 0%-100%. As an example, a racemic mixture has an ee of 0%, while a single completely pure enantiomer has an ee of 100%. A mixture comprising 70% of one enantiomer and 30% of the other has an ee of 40% (70%–30%). The following formulas may be used to calculate ee. See, e.g., Polavarapu, Org Biomol Chem., 2020; 18(35):6801-6806.

Enantiomeric Excess (% ee)=[(moles of enantiomer–moles of other enantiomer)/total moles of both enantiomers]×100    Formula I:

Enantiomeric Excess (% ee)=([$R$]–[$S$])/([$R$]+[$S$])=% $R$–% $S$    Formula II:

c. Synthesis of MDMA Enantiomers

Although numerous methods in the art can be used to obtain optical isomers of the compounds of the invention (e.g., by resolution of the racemate), enantiomeric R-MDMA also may be produced directly by chemical synthesis. Methods of synthesizing MDMA enantiomers are available to one of skill in the art. For example, enantiomerically enriched MDMA can be synthesized based on the reductive amination of 3,4-(methyl-enedioxy)phenylacetone and enantiomerically enriched alphaphenethylamine (Nichols et al., J Med. Chem., 1973; 16 (5), 480-83). Pizarro et al., Bioorg. Med. Chem. Lett., 2002; 10, 1085-92 discloses a method of synthesis of enantiomerically enriched MDMA based on the resolution of a chiral intermediate. See also, Nichols et al., J Med. Chem., 1986; 29, 2009-15.

In one exemplary reaction scheme, the R-MDMA of the invention is synthesized by reacting Methylenedioxyphenyl-propan-2-one with (R)-alpha-methylbenzamine, followed by hydrogenation for the production of R-MDA ((R–)-3,4-methylenedioxyamphetamine), which is then converted into R-MDMA through the reduction of the formamide. This synthetic scheme is shown in Scheme 1.

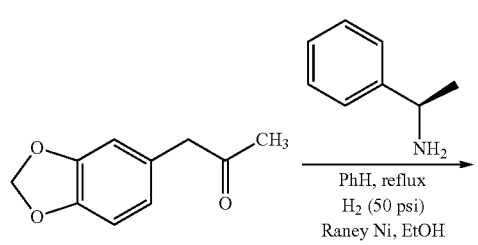

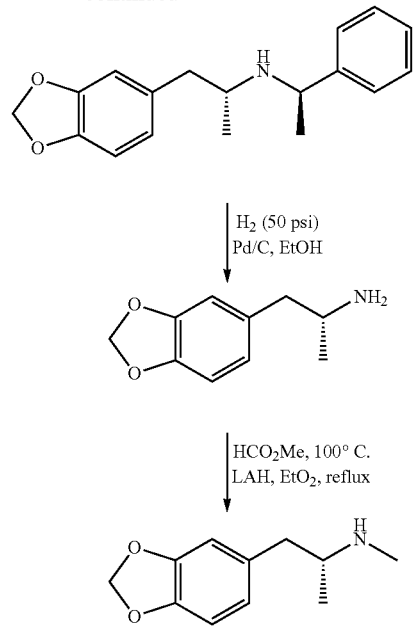

Scheme 1 shows an exemplary synthesis scheme for producing R-MDMA, using 3,4-methylenedioxyphenylpro-pan-2-one as a precursor.

Additionally, R-MDMA and S-MDMA may be synthesized using 3,4-dihydroxybenzoic acid as a precursor, as shown in Scheme 2 and Scheme 3:

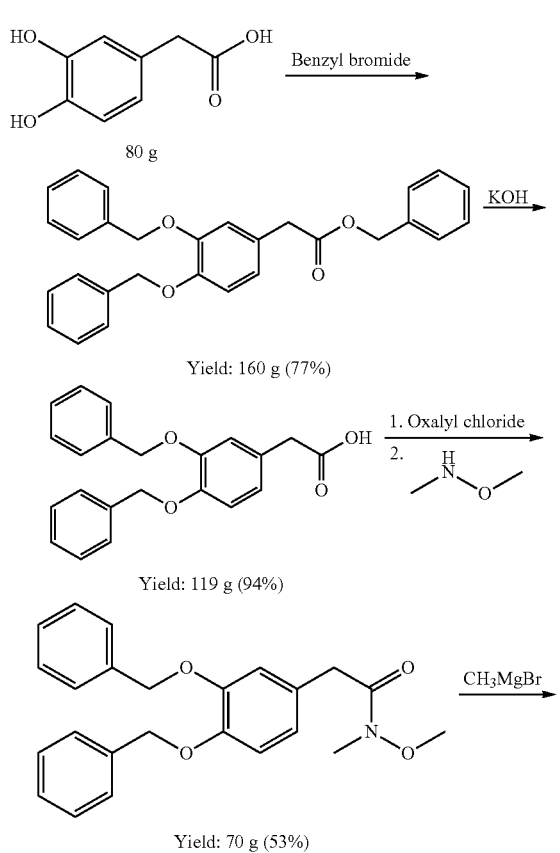

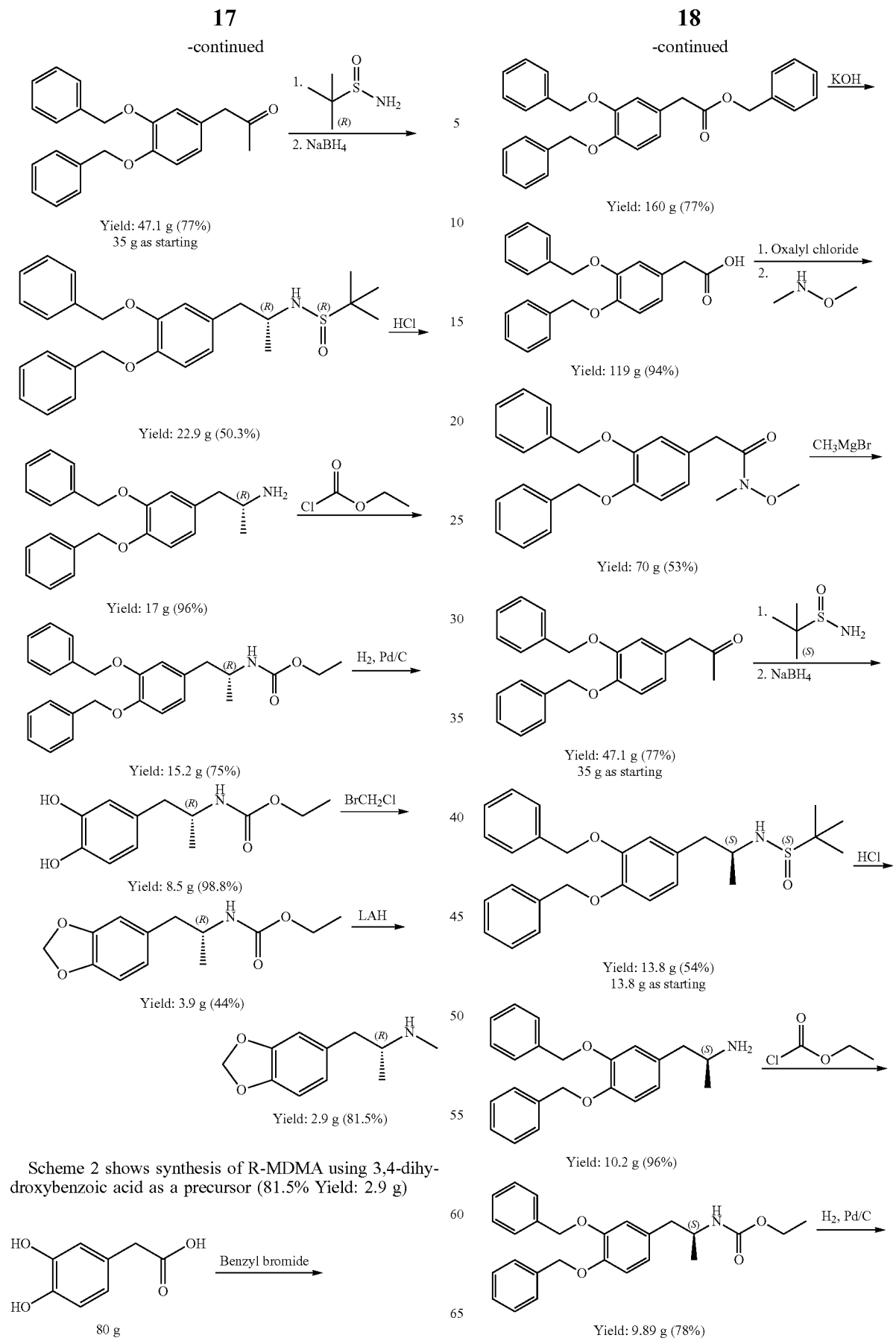
Scheme 2 shows synthesis of R-MDMA using 3,4-dihydroxybenzoic acid as a precursor (81.5% Yield: 2.9 g)

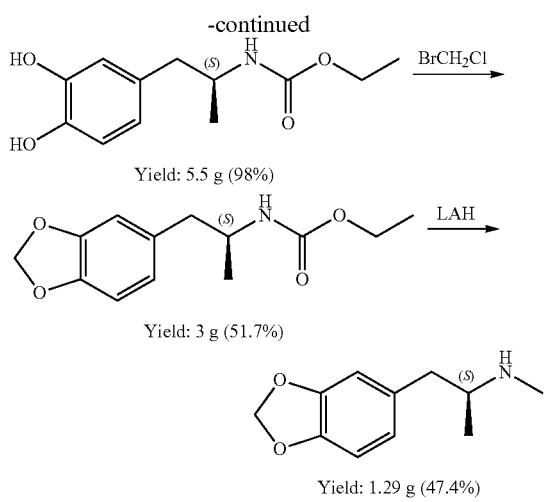

Yield: 1.29 g (47.4%)

Scheme 3 shows synthesis of S-MDMA using 3,4-dihydroxybenzoic acid as a precursor (47.4% Yield: 1.29 g).

Additionally, MDMA enantiomers may be synthesized in accordance with the methods described in Example 10 with modifications. FIG. 2-5 show NMR spectroscopy and mass spectrometry on R-MDMA and S-MDMA produced in accordance with such methods. Other methods for synthesizing the compounds disclosed herein and/or their starting materials are described in the art or will be readily apparent to the skilled artisan in view of the general knowledge in the art (see, e.g., Green et al., "Protective Groups in Organic Chemistry," (Wiley, 2nd ed. 1991); Harrison et al., "Compendium of Synthetic Organic Methods," Vols. 1-8 (John Wiley and Sons, 1971-1996); "Beilstein Handbook of Organic Chemistry," Beilstein Institute of Organic Chemistry, Frankfurt, Germany; Feiser et al, "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes I-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). In general, approaches used for similar compounds may be applied or adapted, such adaptation being that known and understood to those of skill (see, e.g., Shulgin & Shulgin, PiHKAL: A Chemical Love Story, Transform Press, 1992; Glennon et al., J Med Chem, 1986; 29(2), 194-199; Nichols et al., J Med Chem, 1991; 34(1), 276-281; Kedrowski et al., Organic Letters, 2007; 9(17), 3205-3207; Heravi & Zadsirjan, Current Organic Synthesis, 2016; 13(6), 780-833; Keri et al., European J Med Chem, 2017; 138, 1002-1033; PerezSilanes et al., J Heterocyclic Chem, 2001; 38(5), 1025-1030; and references therein).

Methods of analyzing enantiomers, e.g., the enantiomeric content in a non-racemic enantiomeric mixture, are available to one of skill. For example, enantiomeric content of a provided non-racemic mixture may be determined using chiral HPLC or vibrational circular dichroism (VCD) spectroscopy. Alternatively, a derivatizing agent may be used to prepare a diastereomer, which can then be quantified according to analytical methods, e.g., NMR, HPLC, and others. See, e.g., Nichols et al., J Med Chem, 1973; 16(5), 480-83; Fallon et al., Clinical Chem, 1999; 45(7):1058-1069. Regarding the range of experimental error associated with determining the enantiomeric content, a person of ordinary skill in the art would understand that each analytical technique has its own degree of precision.

For the provided enantiomeric mixtures, it will be understood that the deviation from the nominal amount of a mixture, e.g., R:S in a ratio of 9:1 (90% R-MDMA and 10% S-MDMA), to the actual amount, such as determined by an analytical method, is 0.05% or less, within 0.05% to 0.99%, within 0.05% to 0.9%, within 0.05% to 0.8%, within 0.05% to 0.7%, within 0.05% to 0.6%, within 0.05% to 0.5%, within 0.05% to 0.4%, within 0.05% to 0.3%, within 0.05% to 0.2%, or within 0.05% to 0.1%, wherein the range is inclusive, or does not exceed 1%. In one example, the enantiomeric content of a non-racemic mixture in a nominal amount of 9:1 R:S MDMA may be determined to have 90%±0.05% R-MDMA, such as 89.95% or 90.05%, and 10%±0.05% S-MDMA, such as 9.95% or 10.05% S-MDMA. In another example, the enantiomeric content of a non-racemic mixture in a nominal amount of 9:1 R:S MDMA may be determined to have 90%±0.1% R-MDMA, such as 89.9% or 90.1%, and 10%±0.1% S-MDMA, such as 9.9% or 10.1% S-MDMA. As such, a nominal amount of 9:1 R:S MDMA may be determined to have from 89.9% to 90.1% R-MDMA, where the range is inclusive and including values in between, where the remainder is S-MDMA.

Challenges to characterizing enantiomers include self-disproportionation of enantiomers (SDE) and self-induced diastereomeric anisochronism (SIDA). SDE refers to the spontaneous fractionation of scalemic material into enantioenriched and -depleted fractions in response to a physicochemical process. Such process may include precipitation, (b) centrifugation, (c) evaporation, (d) distillation, (e) crystallization, (f) sublimation, and (g) achiral chromatography (e.g. column, flash, MPLC, HPLC, SEC, GC, etc) (Han et al., Chem. Sci., 2018; 9, 1718-1739). SIDA has been described in the context of NMR (Baumann et al., Symmetry, 2020; 12(7), 1106).

The compounds of the invention also include the prodrugs thereof. Prodrugs are compounds that are metabolized or otherwise transformed inside the body to the active pharmacologic agent(s) of interest. Thus, prodrug will contain an "active" component, e.g., a compound of the invention, and a prodrug moiety. Examples include addition of amino acids to the amine, which can be removed within the body by esterases or similar enzymes, and reactions at the keto-group to form enol ethers, enol esters, and imines, but other prodrugs and precursors should be understood to be within the scope of the invention. Prodrugs are frequently (though not necessarily) pharmacologically less active or inactive until converted to the parent drug. This is done in the body by a chemical or biological reaction. In some cases, the moiety or chemicals formed from it may also have beneficial effects, including increasing therapeutic effects, decreasing undesirable side effects, or otherwise altering the pharmacokinetics or pharmacodynamics of the active drug. When the chemical formed from the prodrug moiety has beneficial effects that contribute to the overall beneficial effects of administering the prodrug, then the formed chemical is considered a "codrug." In embodiments, compounds of the invention also include codrugs.

Types of prodrugs contemplated to be within the scope and spirit of the invention include compounds that are transformed in various organs or locations in the body (e.g., liver, kidney, G.I., lung, tissue) to release the active compound. For example, liver prodrugs will include active compounds conjugated with a polymer or chemical moiety that is not released until acted upon by liver cytochrome enzymes; CYP metabolism includes dealkylation, dehydrogenation, reduction, hydrolysis, oxidation, and the breakdown of aromatic rings. Kidney prodrugs will include active compounds conjugated to L-gamma-glutamyl or N-acetyl-L-gamma glutamic moieties so that they are metabolized by gamma-glutamyl transpeptidase before they are bioactive; alternatively, they may be conjugated to alkylglucoside moieties to create glycosylation-based prodrugs. Digestive or G.I. prodrugs will include those where an active compound is, e.g., formulated into microspheres or nanospheres that do not degrade until the spheres are subjected to an acidic pH; formulated with an amide that will resist biochemical degradation until colonic pH is achieved; or conjugated with a linear polysaccharide such as pectin that will delay activation until the combination reaches the bacteria in the colon. Besides these exemplary prodrug forms, many others will be known to those of skill, and MDMA prodrugs have been disclosed, e.g., in PCT Pub. Nos. WO2005/000334, WO2022/05396, and WO2022/106947.

d. MDMA Salts

In some aspects, provided herein are salts of MDMA, including salts of enantiomeric MDMA, such as salts of R-MDMA and salts of S-MDMA, and including salts of non-racemic mixtures of MDMA, such as 9:1 R:S-MDMA. In some embodiments, the salt is a pharmaceutically acceptable salt. In some embodiments, the salt of a provided MDMA enantiomer or non-racemic mixture thereof is a hydrochloride salt. In some embodiments, the salt is a phosphate salt. In some embodiments, the salt is a sulfate salt. In some embodiments, the salt of R-MDMA in a provided enantiomeric mixture is the same as the salt of S-MDMA in said mixture, for example, R-MDMA HCL and S-MDMA HCL. In some embodiments, the salt of R-MDMA in a provided enantiomeric mixture is different from the salt of S-MDMA in said mixture. In some embodiments, R-MDMA or S-MDMA in the mixture is a hydrochloride salt and the other is a sulfate salt, such as R-MDMA HCL and S-MDMA sulfate or R-MDMA sulfate and S-MDMA HCL. In some embodiments, reference to "a salt" such as "R-MDMA, S-MDMA, or a salt thereof" therefore may mean more than a single salt.

In some embodiments, a provided non-racemic mixture comprises a salt of R-MDMA and a salt of S-MDMA, wherein R-MDMA is present in an enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, a provided non-racemic mixture comprises a salt of R-MDMA and a salt of S-MDMA, wherein R-MDMA is present in an enantiomeric excess of 10%-95%, 20%-95%, 30%-95%, 40%-95%, 50%-95%, 55%-95%, 60%-90%, 65%-90%, or 75%-85%. In some embodiments, a non-racemic mixture comprises a salt of R-MDMA and a salt of S-MDMA, wherein R-MDMA is present in an enantiomeric excess of 10%, 15%, 20%, 25%, 30%, 35%, 40%, 45%, 50%, 55% 60%, 65%, 70%, 75%, 80%, 85%, 90%, or 95%. In some embodiments, a non-racemic mixture comprises a salt of R-MDMA and a salt of S-MDMA, wherein R-MDMA is present in enantiomeric excess of in enantiomeric excess of about 75%, 76%, 77%, 78%, 79%, 80%, 81%, 82%, 83%, 84%, or 85%. In some embodiments, a non-racemic mixture comprises a salt of R-MDMA and a salt of S-MDMA, wherein R-MDMA is present in enantiomeric excess of about 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1%. In some embodiments, a non-racemic mixture comprises a salt of R-MDMA and a salt of S-MDMA, wherein R-MDMA is present in an enantiomeric excess of about 79.5%, 79.6%, 79.7%, 79.8%, 79.9%, 80%, 80.1%, 80.2%, 80.3%, 80.4%, or 80.5%. In some embodiments, a provided non-racemic mixture for administration to a subject comprises 90% or less of R-MDMA and 10% or more of S-MDMA. In some embodiments, the non-racemic mixture comprises a salt of R-MDMA and a salt of S-MDMA in a ratio of about 6:1 to 12:1, 7:1 to 11:1, or 8:1 to 10:1. In some embodiments, the non-racemic mixture comprises a salt of R-MDMA and a salt of S-MDMA in a ratio of 6:1, 7:1, 8:1, 9:1, 10:1, 11:1, or 12:1. In some embodiments, the non-racemic mixture comprises a salt of R-MDMA and a salt of S-MDMA in a ratio of 6:1, 7:1, 8:1, 9:1, or 10:1. In some embodiments, the salt of an enantiomerically enriched mixture comprises a mixture of R-MDMA HCl and S-MDMA HCl in a ratio of about 8:1, 9:1, or 10:1. In some embodiments, the salt of an enantiomerically enriched mixture comprises a mixture of R-MDMA HCl and S-MDMA HCl in a ratio of 9:1. In some embodiments, a provided ratio describes a molar ratio of R-MDMA to S-MDMA. In embodiments where the salts of R-MDMA and S-MDMA are the same, a provided ratio may refer to a weight by weight ratio.

Since the compounds of the invention are amines, they are basic in nature and accordingly react with any of a number of inorganic and organic acids to form pharmaceutically acceptable acid addition salts. Since the free amines of this invention are oily and have decreased stability at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like.

Exemplary salts of a provided MDMA enantiomer, for example, in a non-racemic mixture of MDMA enantiomers, or of a non-racemic mixture of MDMA, such as a 9:1 mixture of R:S-MDMA, include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d lactate, decanoate, dichloroacetate, digluconate, dodecylsulfate, edentate, edetate, edisylate, estolate, esylate, ethanesulfonate, ethyl sulfate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, hippurate, hybenzate, hydrabamine, hydrobromide, hydrobromide/bromide, hydrochloride, hydroiodide, hydroxide, hydroxybenzoate, hydroxynaphthoate, iodide, isethionate, isothionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like. See, e.g., Berge et al., "Pharmaceutical Salts," J. Pharm. Sci., 1977; 66:1-19. In some embodiments, pharmaceutically acceptable salts are those employing a hydrochloride anion, e.g., R-MDMA HCl, S-MDMA HCl, and 9:1 R:S-MDMA HCl.

e. Methods of Making an Enantiomeric Mixture

In some aspects, provided herein are methods of making enantiomeric mixtures comprising R-MDMA and S-MDMA, such as non-racemic mixtures thereof. In some embodiments, a method of making a provided non-racemic mixture comprises synthesizing R-MDMA, S-MDMA, or a salt thereof, such as by enantiospecific synthesis. In some embodiments, the method comprises recrystallizing R-MDMA, S-MDMA, or a salt thereof in a weight ratio. In some embodiments, the weight ratio is 6:1, 7:1, 8:1, 9:1, 10:1, 11:1, or 12:1.

In some embodiments, the non-racemic enantiomeric mixture comprises the hydrochloride salt of R-MDMA and/or S-MDMA. In some embodiments, the non-racemic enantiomeric mixture comprises the phosphate salt of R-MDMA and/or S-MDMA. In some embodiments, the non-racemic enantiomeric mixture comprises the sulfate salt of R-MDMA and/or S-MDMA.

B. Pharmaceutical Compositions

While it is possible to administer a compound employed in the methods of this invention directly without any formulation, the compounds are usually administered in the form of pharmaceutical compositions. In some aspects, provided herein are pharmaceutical compositions comprising MDMA enantiomers and non-racemic mixtures thereof. In some embodiments, the pharmaceutical composition comprises 90% or less of R-MDMA and 10% or more of S-MDMA, or a pharmaceutically acceptable salt thereof. In some embodiments, the pharmaceutical composition comprises R-MDMA or a pharmaceutically acceptable salt thereof in enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, the pharmaceutical composition comprises R-MDMA or a pharmaceutically acceptable salt thereof in enantiomeric excess of about 10%-95%, 20%-95%, 30%-95%, 40%-95%, 50%-95%, 55%-95%, 60%-90%, 65%-90%, 70%-85%, or 75%-85%, wherein each range is inclusive. In some embodiments, the pharmaceutical composition comprises R-MDMA or a pharmaceutically acceptable salt thereof in enantiomeric excess of about 10%, 15%, 20%, 25%, 30%, 35%, 40%, 45%, 50%, 55%, 60%, 65%, 70%, 75%, 80%, 85%, 90%, or 95%. In some embodiments, the pharmaceutical composition comprises R-MDMA and S-MDMA, or a pharmaceutically acceptable salt thereof, in an ratio of about 6:1 to 12:1, 7:1 to 11:1, or 8:1 to 10:1. In some embodiments, the pharmaceutical composition comprises R-MDMA and S-MDMA, or a pharmaceutically acceptable salt thereof, in a ratio of about 6:1, 7:1, 8:1, 9:1, 10:1, 11:1, or 12:1. In some embodiments, the pharmaceutical composition comprises R-MDMA and S-MDMA, or a pharmaceutically acceptable salt thereof, in a ratio of 9:1.

"Pharmaceutical compositions" are compositions that include the disclosed compound(s) together in an amount (for example, in a unit dosage form) with a pharmaceutically acceptable carrier, diluent, or excipient. It will be understood that some embodiments do not have a single carrier, diluent, or excipient alone, but have multiple carriers, diluents, and/or excipients. Compositions can be prepared by standard pharmaceutical formulation techniques such as disclosed in Remington: The Science and Practice of Pharmacy (2005) 21th ed., Mack Publ. Co., Easton, Pa.; The Merck Index (1996) 12th ed., Merck Publ. Group, Whitehouse, N.J.; Pharm. Principles of Solid Dosage Forms (1993), Technomic Publ. Co., Inc., Lancaster, Pa.; and Ansel and Stoklasa, Pharm. Calculations (2001) I Ith ed., Lippincott Williams & Wilkins, Baltimore, Md.; and Poznansky et al. Drug Delivery Systems (1980), R. L. Juliano, ed., Oxford, N.Y, pp. 253-315).

"Pharmaceutically acceptable" as used in connection with an excipient, carrier, diluent, or other ingredient means that the ingredient is generally safe and, within the scope of sound medical judgment, suitable for use in contact with the cells of humans and other animals without undue toxicity, irritation, allergic response, or complication, and commensurate with a reasonable risk/benefit ratio.

Pharmaceutical compositions can be administered by a variety of routes including oral, mucosal (e.g., buccal, sublingual), rectal, transdermal, subcutaneous, intravenous, intramuscular, inhaled, and intranasal. The compounds employed in the methods of this invention are effective as oral, mucosal (e.g., buccal, sublingual), rectal, transdermal, subcutaneous, intravenous, intramuscular, inhaled, and intranasal compositions. Such compositions are prepared in a manner well known in the pharmaceutical art and comprise at least one active compound. (See, e.g., Remington, 2005, Remington: The science and practice of pharmacy, 21st ed., Lippincott Williams & Wilkins.)

In making the compositions employed in the present invention the active ingredient is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier, or medium for the active ingredient. Thus, the compositions can be in the form of tablets (including orally disintegrating, swallowable, sublingual, buccal, and chewable tablets), pills, powders, lozenges, troches, oral films, thin strips, sachets, cachets, elixirs, suspensions, emulsions, microemulsions, liposomal dispersions, aqueous and non-aqueous solutions, slurries, syrups, aerosols (as a solid or in a liquid medium), ointments containing for example up to 10% by weight of the active compound, soft and hard gelatin capsules, suppositories, dry powders for inhalation, liquid preparations for vaporization and inhalation, topical preparations, transdermal patches, sterile injectable solutions, and sterile packaged powders. Compositions may be formulated as immediate release, controlled release, sustained (extended) release or modified release formulations.

Different embodiments of the invention include the following examples: Pharmaceutically acceptable complex derivatives of each drug in each group, including solvates, salts, esters, enantiomers, isomers (stereoisomers and/or constitutional, including ones based on substituting deuterium for hydrogen), derivatives or prodrugs of R-MDMA. Among derivatives of a compound are included its "physiologically functional derivatives," which refers to physiologically tolerated chemical derivatives of the compound having the same physiological function thereof, for example, by being convertible in the body thereto, and which on administration to a mammal such as a human is able to form (directly or indirectly) the compound or an active metabolite thereof (acting therefore, like a prodrug), or by otherwise having the same physiological function, despite one or more structural differences. According to the present invention, examples of physiologically functional derivatives include esters, amides, carbamates, ureas, and heterocycles.

Another embodiment of the invention includes multiple variations in the pharmaceutical dosages of each drug in the combination as further outlined below. Another embodiment of the invention includes various forms of preparations including using solids, liquids, immediate or delayed or extended-release forms. Many types of variations are possible as known to those skilled in the art.

Another embodiment of the invention includes multiple routes of administration, which may differ in different patients according to their preference, comorbidities, side effect profile, pharmacokinetic and pharmacodynamic considerations, and other factors (IV, PO, transdermal, etc.). Another embodiment of the invention includes the presence of other substances with the active drugs, known to those skilled in the art, such as fillers, carriers, gels, skin patches, lozenges, or other modifications in the preparation to facilitate absorption through various routes (such as gastrointestinal, transdermal, etc.) and/or to extend the effect of the drugs, and/or to attain higher or more stable serum levels or to enhance the therapeutic effect of the active drugs in the combination.

In preparing a formulation, it may be necessary to mill the active compound to provide an appropriate particle size prior to combining with other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 350 mg, more preferably about 5.0 to about 180 mg, of the active ingredients. The term "unit dosage form" refers to a physically discrete unit suited as unitary dosages for the subject to be treated, each unit containing a predetermined quantity of active material calculated to produce the desired therapeutic effect(s), in association with a suitable pharmaceutical carrier, diluent, or excipient. Unit dosage forms are often used for ease of administration and uniformity of dosage. Unit dosage forms can contain a single or individual dose or unit, a sub-dose, or an appropriate fraction thereof (e.g., one half a "full" dose), of the pharmaceutical composition administered.

Unit dosage forms include capsules, troches, cachets, lozenges, tablets, ampules and vials, which may include a composition in a freeze-dried or lyophilized state; a sterile liquid carrier, for example, can be added prior to administration or delivery in vivo. Unit dosage forms also include ampules and vials with liquid compositions disposed therein. Unit dosage forms further include compounds for transdermal administration, such as "patches" that contact the epidermis of a subject for an extended or brief period of time.

It will be apparent that the compositions of the invention are not limited to combinations of a single compound (i.e., R-MDMA), and a single carrier, diluent, or excipient alone, but also include combinations of multiple compounds (including additional active compounds), and/or multiple carriers, diluents, and excipients. Pharmaceutical compositions of this invention thus may comprise R-MDMA together with one or more other active agents (or their derivatives and analogs) in combination, together with one or more pharmaceutically-acceptable carriers, diluents, and/or excipients, and additionally with one or more other active compounds.

In some embodiments, a formulation of the invention will be prepared so as to increase an existing therapeutic effect, provide an additional therapeutic effect, improve a physiological or psychological effect, increase a desired property such as stability or shelf-life, decrease an unwanted effect or property, alter a property in a desirable way (such as pharmacokinetics or pharmacodynamics), modulate a desired system or pathway (e.g., a neurotransmitter system), or provide synergistic effects.

In some embodiments, "therapeutic effects" that may be increased or added in embodiments of the invention include, but are not limited to, antioxidant, anti-inflammatory, analgesic, antineuropathic, antinociceptive, antimigraine, anxiolytic, antidepressant, antipsychotic, anti PTSD, immunostimulant, anti-cancer, antiemetic, orexigenic, antiulcer, antihistamine, antihypertensive, anticonvulsant, antiepileptic, bronchodilator, neuroprotective, entactogenic, empathogenic, entheogenic, psychedelic, sedative, and stimulant effects.

In some embodiments, improvements in "physiological or psychological effects" include any one or more of a reduction in nausea and vomiting, an improved pharmacokinetic profile, a reduction in subjective body load during the therapeutic window, an improvement in the subjective valence of the experience, an improvement in feelings of positive affect, an increase in the therapeutic window, an improvement in behavioral integration, a reduction of anxiety, a reduction in addictive liability or abuse potential, a reduction in neurotoxicity, a reduction in hyperthermia or hypothermia, and a reduction in stimulation.

"Synergistic effects" will include increases in potency, bioactivity, bioaccessibility, bioavailability, or therapeutic effect, that are greater than the additive contributions of the components acting alone. Numerous methods known to those of skill in the art exist to determine whether there is synergy as to a particular effect, i.e., whether, when two or more components are mixed together, the effect is greater than the sum of the effects of the individual components when applied alone, thereby producing "1+1>2." One such method is the isobologram analysis (or contour method) (see, e.g., Huang et al., Front. Pharmacol. 2019; 10:1222).

The goal of increasing an existing therapeutic effect, providing an additional therapeutic effect, improving a physiological or psychological effect, increasing a desired property such as stability or shelf-life, decreasing an unwanted effect or property, altering a property in a desirable way (such as pharmacokinetics or pharmacodynamics), modulating a desired system or pathway (e.g., a neurotransmitter system), or otherwise inducing synergy, in some embodiments is achieved by the inclusion of an additional active compound.

It is contemplated that such additional active compounds may be selected from the group including oxytocin, amino acids, antioxidants, anti-inflammatory agents, analgesics, antineuropathic and antinociceptive agents, antimigraine agents, anxiolytics, antidepressants, antipsychotics, anti-PTSD agents, immunostimulants, anti-cancer agents, antiemetics, orexigenics, antiulcer agents, antihistamines, antihypertensives, anticonvulsants, antiepileptics, bronchodilators, neuroprotectants, entactogens and empathogens, entheogens, psychedelics, monoamine oxidase inhibitors, sedatives, stimulants, and vitamins. These ingredients may be in ion, freebase, or salt form, and may be isomers, prodrugs, derivatives (including physiologically functional derivatives), or analogs.

In some embodiments, the psychedelic is any of psilocybin, psilocin, DMT, 5-MeO-DMT, mescaline, salvinorin A, THC, 4-Aco-DMT, 5-Br-DMT, 5-Cl-DMT, 5-F-DMT, PRO-LAD, ETH-LAD, AL-LAD, 1P-LSD, DiPT, 2C-B, and 2C-C.

In some embodiments, the entactogen is any of 4-MTA, MDAI, 5-methyl-MDA, 5-APB, or 6-APB, DiFMDA, MBDB, BDB, MDA, and MDEA.

In embodiments, the additional active compound is a serotonergic agent. A "serotonergic agent" may refer to a compound that binds to, blocks, activates, inhibits, or otherwise influences (e.g., via an allosteric reaction) activity at one or more serotonin receptors, including any one or more serotonin receptor subtypes. In embodiments, a serotonergic agent binds to a serotonin receptor. In embodiments, a serotonergic agent indirectly affects a serotonin receptor, e.g., via interactions affecting the reactivity of other molecules at the serotonin receptor. In embodiments, a serotonergic agent is an agonist, e.g., a compound activating a serotonin receptor. In embodiments, a serotonergic agent is an antagonist, e.g., a compound binding to but not activating a serotonin receptor, e.g., blocking a receptor. In embodiments, a serotonergic agent is an effector molecule, e.g., a compound binding to an enzyme for allosteric regulation. In embodiments, a serotonergic agent acts (either directly or indirectly) at more than one type of receptor, including receptors other than serotonergic or other monoaminergic receptors. In embodiments, a serotonergic agent blocks the serotonin transporter (SERT) and results in an elevation of the synaptic concentration of serotonin, and an increase of neurotransmission. In embodiments, a serotonergic agent acts as a reuptake modulator and inhibits the plasmalemmal transporter-mediated reuptake of serotonin from the synapse into the presynaptic neuron, leading to an increase in extracellular concentrations of serotonin and an increase in neurotransmission. In embodiments, a serotonergic agent inhibits the activity of one or both monoamine oxidase enzymes, resulting in an increase in concentrations of serotonin and an increase in neurotransmission. In embodiments, a serotonergic agent is an antidepressant or anxiolytic, such as an SSRI, serotonin-norepinephrine reuptake inhibitor (SNRI), tricyclic antidepressant (TCA), monoamine oxidase inhibitor (MAOI), or atypical antidepressant. In other embodiments, a serotonergic agent is selected from the group consisting of: (1) serotonin transport inhibitors; (2) serotonin receptor modulators; (3) serotonin reuptake inhibitors; (4) serotonin and norepinephrine reuptake inhibitors; (5) serotonin dopamine antagonists; (6) monoamine reuptake inhibitors; (7) pyridazinone aldose reductase inhibitors; (8) stimulants of serotonin receptors; (9) stimulants of serotonin synthesis; (10) serotonin receptor agonists; (11) serotonin receptor antagonists; and (12) serotonin metabolites.

In embodiments, the additional active compound is a phenethylamine disclosed in Shulgin and Shulgin, PIHKAL: A Chemical Love Story, Transform Press (1994), or a tryptamine disclosed in Shulgin and Shulgin, TH-KAL: The Continuation, Transform Press (1997), both of which are incorporated by reference herein as if fully set forth herein.

In some embodiments, the compositions of the invention are formulated in a pharmaceutically acceptable oral dosage form. Oral dosage forms include oral liquid dosage forms (such as tinctures, drops, emulsions, syrups, elixirs, suspensions, and solutions, and the like) and oral solid dosage forms. The pharmaceutical compositions of the present invention also may be prepared as formulations suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

a. Oral Liquid Dosage Forms

Oral liquid dosage forms include solutions, emulsions, suspensions, and syrups. These oral liquid dosage forms may be formulated with any pharmaceutically acceptable excipient known to those of skill in the art for the preparation of liquid dosage forms. For example, water, glycerin, simple syrup, alcohol, medium chain triglycerides (MCT), and combinations thereof. Liquid dosage forms for oral administration may be in the form of pharmaceutically acceptable emulsions, syrups, elixirs, suspensions, and solutions, which may contain an inactive diluent, such as water. Pharmaceutical formulations may be prepared as liquid suspensions or solutions using a sterile liquid, such as but not limited to, an oil, water, an alcohol, and combinations of these pharmaceutically suitable surfactants, suspending agents, emulsifying agents, may be added for oral or parenteral administration. Liquid formulations also may be prepared as single dose or multi-dose beverages. Suspensions may include oils. Such oils include peanut oil, sesame oil, cottonseed oil, corn oil, and olive oil. Suitable oils also include carrier oils such as MCT and long chain triglyceride (LCT) oils. Suspension preparation may also contain esters of fatty acids such as ethyl oleate, isopropyl myristate, fatty acid glycerides, and acetylated fatty acid glycerides. Suspension formulations may include alcohols, (such as ethanol, isopropyl alcohol, hexadecyl alcohol), glycerol, and propylene glycol. Ethers, such as poly(ethylene glycol), petroleum hydrocarbons such as mineral oil and petrolatum, and water may also be used in suspension formulations. Suspension can thus include an aqueous liquid or a non-aqueous liquid, an oil-in-water liquid emulsion, or a water-in-oil emulsion.

In some embodiments, formulations are provided comprising the compositions of the invention and at least one dispersing agent or suspending agent for oral administration to a subject. The formulation may be a powder and/or granules for suspension, and upon admixture with water, a substantially uniform suspension is obtained. The aqueous dispersion can comprise amorphous and non-amorphous particles consisting of multiple effective particle sizes such that a drug is absorbed in a controlled manner over time.

Dosage forms for oral administration can be aqueous suspensions selected from the group including pharmaceutically acceptable aqueous oral dispersions, emulsions, solutions, and syrups. See, e.g., Singh et al., Encyclopedia of Pharm. Tech., 2nd Ed., 754-757 (2002). In addition to the active agents of the present invention, the liquid dosage forms may comprise additives, such as one or more (a) disintegrating agents, (b) dispersing agents, (c) wetting agents, (d) preservatives, (e) viscosity enhancing agents, (f) sweetening agents, or (g) flavoring agents.

Examples of disintegrating agents for use in the aqueous suspensions and dispersions include a starch, e.g., a natural starch such as corn starch or potato starch, a pregelatinized starch, or sodium starch glycolate; a cellulose such as a wood product, microcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay; a gum such as agar, guar, locust bean, Karaya, pectin, or tragacanth; sodium starch glycolate; bentonite; a natural sponge; a surfactant; a resin such as a cation-exchange resin; citrus pulp; and sodium lauryl sulfate.

Examples of dispersing agents suitable for the aqueous suspensions and dispersions include hydrophilic polymers, electrolytes, Tween® 60 or 80, polyethylene glycol (PEG), polyvinylpyrrolidone (PVP), carbohydrate-based dispersing agents, noncrystalline cellulose, magnesium aluminum silicate, triethanolamine, polyvinyl alcohol (PVA), polyvinylpyrrolidone/vinyl acetate copolymer, poloxamers, and poloxamines.

Examples of wetting agents (including surfactants) suitable for the aqueous suspensions and dispersions include acetyl alcohol, glycerol monostearate, polyoxyethylene sorbitan fatty acid esters, PEG, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, and phosphatidylcholine.

Examples of preservatives suitable for aqueous suspensions or dispersions include potassium sorbate, parabens (e.g., methylparaben and propylparaben) and their salts, benzoic acid and its salts, other esters of para hydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Examples of viscosity enhancing agents suitable for aqueous suspensions or dispersions include methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans, and combinations thereof. The concentration of the viscosity-enhancing agent will depend upon the agent selected and the viscosity desired.

In addition to additives listed above, the liquid formulations of the invention can also comprise inert diluents commonly used in the art, such as water or other solvents, solubilizing agents, emulsifiers, flavoring agents and/or sweeteners. Co-solvents and adjuvants also may be added to a formulation. Non-limiting examples of co-solvents contain hydroxyl groups or other polar groups, for example, alcohols, glycols, glycerol, polyoxyethylene alcohols, and polyoxyethylene fatty acid esters. Adjuvants include surfactants such as soy lecithin and oleic acid, sorbitan esters such as sorbitan trioleate, and PVP.

b. Oral Solid Dosage Forms

Oral solid dosage forms may include but are not limited to, tablets, capsules, caplets, powders, pellets, multiparticulates, beads, spheres, and/or any combinations thereof. Oral solid dosage forms may be formulated as immediate release, controlled release, sustained release, extended release, or modified release formulations. Accordingly, in some embodiments, the oral solid dosage forms of the present invention may be in the form of a tablet (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including a fast-melt tablet. Additionally, pharmaceutical formulations of the invention may be administered as a single capsule or in multiple capsule dosage form. In some embodiments, the pharmaceutical formulation is administered in two, three, four, or more capsules or tablets.

Oral solid dosage forms may contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof. Oral solid dosage forms also can comprise one or more pharmaceutically acceptable additives such as a compatible carrier, complexing agent, ionic dispersion modulator, disintegrating agent, surfactant, lubricant, colorant, moistening agent, plasticizer, stabilizer, penetration enhancer, wetting agent, anti foaming agent, alone or in combination, as well as supplementary active compound(s).

Supplementary active compounds include preservatives, antioxidants, antimicrobial agents including biocides and biostats such as antibacterial, antiviral and antifungal agents. Preservatives can be used to inhibit microbial growth or increase stability of the active ingredient thereby prolonging the shelf life of the pharmaceutical formulation. Suitable preservatives are known in the art and include EDTA, EGTA, benzalkonium chloride or benzoic acid or benzoates, such as sodium benzoate. Antioxidants include vitamin A, vitamin C (ascorbic acid), vitamin E, tocopherols, other vitamins or provitamins, and compounds such as alpha lipoic acid.

Using standard coating procedures, a film coating may be provided around the active agents of the present invention (see Remington, supra). In one embodiment, some or all of the active agents of the present invention are coated. In another embodiment, some or all of the active agents of the present invention are microencapsulated. In yet another embodiment, some or all of the active agents of the present invention is amorphous material coated and/or microencapsulated with inert excipients. In still another embodiment, the active agent of the present invention are not microencapsulated and are uncoated.

Suitable carriers for use in oral solid dosage forms include acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose (IPMC), hydroxypropylmethylcellulose acetate stearate (HPMCAS), sucrose, microcrystalline cellulose, lactose, and mannitol.

Suitable filling agents for use in oral solid dosage forms include lactose, calcium carbonate, calcium phosphate, dibasic calcium phosphate, calcium sulfate, microcrystalline cellulose, cellulose powder, dextrose, dextrates, dextrose, dextran, starches, pregelatinized starch, HPMC, HPMCAS, hydroxypropylmethylcellulose phthalate, sucrose, xylitol, lactitol, mannitol, sorbitol, sodium chloride, and PEG.

Suitable disintegrants for use in oral solid dosage forms include a starch, e.g., a natural starch such as corn starch or potato starch, a pregelatinized starch, or sodium starch glycolate; a cellulose such as a wood product, microcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay; a gum such as agar, guar, locust bean, Karaya, pectin, or tragacanth; sodium starch glycolate; bentonite; a natural sponge; a surfactant; a resin such as a cation-exchange resin; citrus pulp; and sodium lauryl sulfate.

Suitable binders impart cohesiveness to solid oral dosage form formulations. For powder filled capsules, they aid in plug formation that can be filled into soft or hard shell capsules. For tablets, they ensure that the tablet remains intact after compression and help assure blend uniformity prior to a compression or fill step. Materials suitable for use as binders in the solid dosage forms described herein include celluloses, microcrystalline dextrose, amylase, magnesium aluminum silicate, polysaccharide acids, bentonites, gelatin, polyvinylpyrrolidone/vinyl acetate copolymer, cross-povidone, povidone, starch, pregelatinized starch, tragacanth, dextrin, a sugar (e.g., sucrose, glucose, dextrose, molasses, mannitol, sorbitol, xylitol, lactose), a natural or synthetic gum (e.g., acacia, tragacanth, ghatti gum, mucilage of isapol husks), starch, PVP, larch arabogalactan, Veegum®, PEG, waxes, and sodium alginate. Binder levels of 20-70% can be used in powder-filled gelatin capsule formulations. Binder usage level in tablet formulations is a function of whether direct compression, wet granulation, roller compaction, or usage of other excipients such as fillers which itself can act as moderate binders are used. Formulators in the art can determine binder level for formulations, but binder usage of up to 70% in tablet formulations is common.

Suitable lubricants or glidants for use in oral solid dosage forms include stearic acid, calcium hydroxide, talc, corn starch, sodium stearyl fumarate, alkali-metal and alkaline earth metal salts, stearic acid, sodium stearates, magnesium stearate, zinc stearate, waxes, Stearowet®, boric acid, sodium benzoate, sodium acetate, sodium chloride, leucine, PEG, methoxy-polyethylene glycol, propylene glycol, sodium oleate, glyceryl behenate, glyceryl palmitostearate, glyceryl benzoate, and magnesium or sodium lauryl sulfate.

Suitable diluents for use in oral solid dosage forms include sugars (e.g., lactose, sucrose, and dextrose), polysaccharides (e.g., dextrates and maltodextrin), polyols (e.g., mannitol, xylitol, and sorbitol), and cyclodextrins. Non-water-soluble diluents are compounds typically used in the formulation of pharmaceuticals, such as calcium phosphate, calcium sulfate, starches, modified starches and microcrystalline cellulose, and micro cellulose (e.g., having a density of about 0.45 g/cm3, e.g., Avicel, powdered cellulose), and talc.

Suitable wetting agents for oral solid dosage forms include oleic acid, triethanolamine oleate, glyceryl monostearate, sorbitan monooleate, sorbitan monolaurate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, and vitamin E TPGS. Wetting agents include surfactants.

Suitable surfactants for solid dosage forms include docusate and its pharmaceutically acceptable salts, sodium lauryl sulfate, sorbitan monooleate, poly oxyethylene sorbitan monooleate, polysorbates, poloxamers, bile salts, glyceryl monostearate, copolymers of ethylene oxide and propylene oxide, e.g., Pluronic® (BASF), and the like.

Suitable suspending agents for use in oral solid dosage forms include polyvinylpyrrolidone, PEG (having a molecular weight of about 300 to about 6000, or about 3350 to about 4000, or about 7000 to about 18000), vinylpyrrolidone/vinyl acetate copolymer (S630), sodium alginate, gums (e.g., gum tragacanth and gum acacia, guar gum, xanthans, including xanthan gum), sugars, celluloses, polysorbate-80, polyethoxylated sorbitan monolaurate, polyethoxylated sorbitan monolaurate, and povidone.

Suitable antioxidants for use in oral solid dosage forms include butylated hydroxytoluene (BHT), butyl hydroxyanisole (BHA), sodium ascorbate, Vitamin E TPGS, ascorbic acid, sorbic acid, and tocopherol.

Immediate-release formulations may be prepared by combining a superdisintegrant such as croscarmellose sodium and different grades of microcrystalline cellulose in different ratios. To aid disintegration, sodium starch glycolate may be added.

Where different agents included in fixed-dose combinations are incompatible, cross-contamination can be avoided by incorporation of the agents in different layers in the oral dosage form with the inclusion of barrier layer(s) between the different layers, wherein the barrier layer(s) comprise inert and non-functional material(s).

The above-listed additives should be taken as merely exemplary types of additives that can be included in solid dosage forms of the present invention. The amounts of such additives can be readily determined by one skilled in the art, according to the particular properties desired.

Tablets can be prepared by methods well known in the art. Various methods for the preparation of the immediate release, modified release, controlled release, and extended-release dosage forms (e.g., as matrix tablets having one or more modified, controlled, or extended-release layers) and the vehicles therein are well known in the art. For example, a tablet may be made by compression or molding. Compressed tablets may be prepared by compressing, in a suitable machine, an active ingredient in a free-flowing form such as a powder or granules, optionally mixed with a binder, lubricant, inert diluent, preservative, surface-active or dispersing agent. Molded tablets may be produced by molding, in a suitable apparatus, a mixture of powdered compound moistened with an inert liquid diluent. The tablets may optionally be coated or scored and may be formulated so as to provide a slow or controlled release of the active ingredient therein. Generally recognized compendia of methods include: Remington: The Science and Practice of Pharmacy (2005) 21th ed., Mack Publishing Co., Easton, Pa; Sheth et al. (1980), Compressed tablets, in Pharm. dosage forms, Vol. 1, Lieberman & Lachtman, eds., Dekker, NY.

In embodiments, solid dosage forms are prepared by mixing the active agents with one or more pharmaceutical excipients to form a "bulk blend" composition. The bulk blend composition is homogeneous, i.e., the active agents are dispersed evenly throughout so that the bulk blend may be readily subdivided into equally effective unit dosage forms, such as tablets, pills, and capsules. The individual unit dosages may also comprise film coatings, which disintegrate upon oral ingestion or upon contact with diluents. These formulations can be manufactured by conventional pharmaceutical techniques.

Conventional pharmaceutical techniques for preparation of solid dosage forms include the following, used alone or in combination: (1) dry mixing, (2) direct compression, (3) milling, (4) dry or non-aqueous granulation, (5) wet granulation, or (6) fusion. See, e.g., Lachman et al., Theory and Practice of Industrial Pharmacy (1986). Other methods include spray drying, pan coating, melt granulation, granulation, fluidized bed spray drying or coating (e.g., Wurster coating), tangential coating, top spraying, tableting, and extruding.

Compressed tablets are solid dosage forms prepared by compacting the bulk blend. In various embodiments, compressed tablets which are designed to dissolve in the mouth will comprise one or more flavoring agents. In other embodiments, the compressed tablets will comprise a film surrounding the final compressed tablet. In some embodiments, the film coating can provide a delayed release of the active agents of the present invention formulation. In other embodiments, the film coating aids in patient compliance (e.g., flavor or sweetener coatings).

A capsule may be prepared by placing the bulk blend inside of a capsule, such as a soft gelatin capsule, a standard gelatin capsule, or a non-gelatin capsule such as a capsule comprising HPMC. The bulk blend also may be placed in a sprinkle capsule, and the capsule may be swallowed whole or may be opened and the contents sprinkled on food prior to eating. In some embodiments, the therapeutic dose is split into multiple capsules. For instance, in some embodiments as in the Examples below, where a first dose is twice the amount of a second dose, only one dosage form is prepared, in the amount of the second dose (i.e., administration of the first dosage amount is achieved by using two such dosage forms). In some embodiments, the entire dose of the active agents of the present invention formulation is delivered in a capsule form. In some embodiments the capsule is a soft gelatin capsule, such as of size 00-5. In other embodiments, the capsule is a hard gelatin capsule of equivalent size.

In certain embodiments, the formulations of the present invention are fixed-dose pharmaceutical compositions of the invention and at least one other pharmacological agent. Fixed-dose combination formulations may contain therapeutically efficacious fixed-dose combinations of formulations of the active agents of the invention and other pharmacological agents in the form of a single-layer monolithic tablet or multi-layered monolithic tablet or in the form of a core tablet-in-tablet or multi-layered multi-disk tablet or beads inside a capsule or tablets inside a capsule.

Depending on the desired release profile, oral solid dosage forms may be prepared as immediate release formulations, or as modified release formulations, such as controlled release, extended release, sustained release, or delayed release.

In some embodiments, modified release formulations, such as controlled release, extended release, sustained release, or delayed release formulations are prepared as low dose or micro dose formulations. In some embodiments of modified release formulations, the half-life compared to the half-life of an immediate release formulation is greater by at least 5%, at least 10%, at least 15%, at least 20%, at least 25%, at least 30%, at least 35%, at least 50%, at least 75%, or at least 100%. In some embodiments of modified release formulations, the formulations are designed to result in a comparable $AUC_{0-24}$, and a similar safety and efficacy profile, but having a delayed time to maximum concentration ($t_{max}$) of at least 5%, at least 10%, at least 15%, at least 20%, at least 25%, at least 30%, at least 35%, at least 50%, at least 75%, or at least 100%. In some preferred embodiments, a formulation is designed to be a 12-15 hour product.

In some embodiments, oral solid dosage forms are formulated as a delayed release dosage form by utilizing an enteric coating to affect release in the small intestine of the gastrointestinal tract. An enteric-coated oral dosage form may be a compressed or molded or extruded tablet/mold (coated or uncoated) containing granules, powder, pellets, beads or particles of the active ingredient and/or other composition components, which are themselves coated or uncoated. The enteric-coated oral dosage form may also be a capsule (coated or uncoated) containing pellets, beads or granules of the solid carrier or the composition, which are themselves coated or uncoated. Enteric coatings may also be used to prepare other controlled release dosage forms including extended release and pulsatile release dosage forms. Pulsatile release dosage forms may be formulated using techniques known in the art, such as those described in U.S. Pat. Nos. 5,011,692, 5,017,381, 5,229,135, and 5,840,329. Other suitable dosage forms are described in U.S. Pat. Nos. 4,871,549, 5,260,068, 5,260,069, 5,508,040, 5,567,441 and 5,837,284.

In one embodiment, the controlled release dosage form is a pulsatile release solid oral dosage form comprising at least two groups of particles, each containing active agents of the invention described herein. The first group of particles provides a substantially immediate dose of the active agents of the invention upon ingestion by a subject. The first group of particles can be either uncoated or comprise a coating and/or sealant. The second group of particles comprises coated particles, which may comprise from about 2% to about 75%, preferably from about 2.5% to about 70%, or from about 40% to about 70%, by weight of the total dose of the active agents of the invention, in admixture with one or more binders. Using such means, a single unit dosage form can provide both a first and a second dosage amount in the single form (i.e., the first dosage amount in an immediate release form, and the second dosage amount in a delayed release form).

In another embodiment, gastroretentive sustained release tablets are formulated by using a combination of hydrophilic polymer (e.g., hydroxypropyl methylcellulose), together with swelling agents (e.g., crospovidone, sodium starch glycolate, and croscarmellose sodium), and an effervescent substance (e.g., sodium bicarbonate). Using known methods, gastroretentive tablets can be formulated so as to prolong the gastric emptying time and extend the mean residence time (MRT) in the stomach for optimal drug release and absorption (see, e.g., Arza et al., AAPS PharmSciTech., 2009; 10(1):220-226).

Coatings for providing a controlled, delayed, or extended release may be applied to the pharmaceutical compositions of the invention or to a core containing the compositions. The coating may comprise a pharmaceutically acceptable ingredient in an amount sufficient, e.g., to provide an extended release from e.g., about 1 hours to about 7 hours following ingestion before release of the compositions. In an embodiment, where a delayed release form is used to delay the onset of the second booster MDMA dose, the time of release will preferably be the same time as release of the equivalent immediate dosage form when given as the second dose, allowing both the first and second doses to be taken together. Suitable coatings include one or more differentially degradable coatings including pH-sensitive coatings (enteric coatings), or non enteric coatings having variable thickness to provide differential release of the active agents.

Many other types of modified release systems are known to those of ordinary skill in the art and are suitable for the formulations described herein. Examples of such delivery systems include both polymer- and nonpolymer-based systems, silastic systems, peptide-based systems, wax coatings, bioerodible dosage forms, and compressed tablets using conventional binders. (See, e.g., Liberman et al. Pharmaceutical Dosage Forms, 2 Ed., Vol. 1, pp. 209-214 (1990); Singh et al. Encyclopedia of Pharmaceutical Technology, 2nd Ed., pp. 751-753 (2002); U.S. Pat. Nos. 4,327,725; 4,624,848; 4,968,509; 5,461,140; 5,456,923; 5,516,527; 5,622,721; 5,686,105; 5,700,410; 5,977,175; 6,465,014; and 6,932,983.

c. Additional Dosage Forms

The pharmaceutical compositions of the invention also may be prepared as formulations suitable for intramuscular, subcutaneous, intraperitoneal, or intravenous injection, comprising physiologically acceptable sterile aqueous or non-aqueous solutions, dispersions, suspensions or emulsions, liposomes, and sterile powders for reconstitution into sterile injectable solutions or dispersions.

Examples of suitable aqueous and non-aqueous carriers, diluents, solvents, or vehicles include water, ethanol, polyols, suitable mixtures thereof, vegetable oils, and injectable organic esters such as ethyl oleate. Additionally, the compositions of the present invention can be dissolved at concentrations of >1 mg/ml using water-soluble beta cyclodextrins (e.g., beta sulfobutyl-cyclodextrin and 2-hydroxypropyl-betacyclodextrin. Proper fluidity can be maintained, for example, by the use of a coating such as a lecithin, by the maintenance of the required particle size in the case of dispersions, and by the use of surfactants.

Formulations suitable for subcutaneous injection also may contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, and sorbic acid. Isotonic agents, such as sugars and sodium chloride may be used. Prolonged drug absorption of an injectable form can be brought about by use of agents delaying absorption, e.g., aluminum monostearate or gelatin.

The compositions of the present invention may also be prepared as suspension formulations designed for extended-release via subcutaneous or intramuscular injection. Such formulations avoid first-pass metabolism, and lower dosages of the active agents will be necessary to maintain equivalent plasma levels when compared to oral formulations. In such formulations, the mean particle size of the active agents and the range of total particle sizes can be used to control the release of those agents by controlling the rate of dissolution in fat or muscle. The compositions also may be prepared for microinjection or injection cannula, as in e.g., Wilson et al., Neuropharmacol. 2008; 55(7):1219-25.

In still other embodiments, effervescent powders containing the compositions of the invention may be prepared. Effervescent salts are used to disperse medicines in water for oral administration. Effervescent salts also may be packaged as single dose or multi-dose drink mixes, alone or in combination with other ingredients, such as vitamins or electrolytes. Effervescent salts are granules or coarse powders containing a medicinal agent in a dry mixture, usually composed of sodium bicarbonate and sodium carbonate, citric acid, and/or tartaric acid. When salts of the present invention are added to water, the acids and the base react to liberate carbon dioxide gas, thereby causing "effervescence." Any acid-base combination that results in the liberation of carbon dioxide can be used, as long as the ingredients are suitable for pharmaceutical use and result in a pH of about 6.0 or higher.

In yet other embodiments, the pharmaceutical compositions disclosed herein are prepared for administration as a nanostructured formulation such as a nanoemulsion, a nanocapsule, a nanoparticle conjugate, or a nano-encapsulated oral or nasal spray. Preparations of the compositions of the present invention as certain nanostructured formulations may be done by reference to the general knowledge of the art. (See, e.g., Jaiswal et al., Biotech., 2015; 3(5):123-27.

The prefix "nano" as used in the terms describing various embodiments of a nanostructured formulation denotes a size range in the nanometer ("nm") scale. Accordingly, sizes of such nanoparticle delivery vehicles include those in the about 1 to about 100 nm, about 100 to about 200 nm, about 200 to about 400 nm, about 400 to about 600 nm, about 600 to about 800 nm, and about 800 to about 1000 nm, as well as "microparticles" in the about 1000 to about 2000 nm (1-2 micrometer ("µm") scale). Particles of certain sizes may be particularly advantageous depending on the method of administration (e.g., for oral liquid emulsion versus for transdermal or topical application). Regardless of method of administration, one will appreciate that smaller particles provide for increased surface area over larger particles such that a higher concentration of cannabinoid receptor binding agent may be applied per volume of particles. A nanoparticle may be metal, lipid, polymer or other materials, or a combination of materials, and nanoparticles may be functionalized such that another moiety also may be attached thereto. Surface functionalization may involve the use of a moiety comprising an anchor group, a spacer and/or a functional group.

Lipid-based nanoparticles (LBNPs) such as liposomes, solid lipid nanoparticles (SLN), and nanostructured lipid carriers (NLC) can be used to transport both hydrophobic and hydrophilic molecules, and can be formulated to display very low or no toxicity, and increase the time of drug action by means of prolonged half-life and controlled release of active agents. Lipid nanosystems also can include chemical modifications to avoid immune system detection (e.g., gangliosides or PEG) or to improve solubility of active agents. In addition, such nanosystems can be prepared in formulations sensitive to pH in order to promote drug release in an acid environment.

In one embodiment, nanosuspensions are synthesized by an antisolvent precipitation method, in which a 100 mg amount of R-MDMA is dissolved per 10 mL of solvent containing ethanol, acetone, methanol, 2-propanol, DMSO and ethylene glycol. The solutions are ultrasonicated for 2 min and stirred with a magnetic stirrer for another 5 min to achieve complete dissolution. A total of 150 mL of deionized water is added while stirring, wherein nanoparticles precipitate and emulsions are formed. A surfactant can be added as a stabilizer, wherein the surfactants (Span 80 and Tween 80 in a proportion of 1:4 wt %) are dissolved in 15 mL of water and then added to the R-MDMA-ethanol solution.

The primary components of nanoparticles are phospholipids, which are organized in a bilayer structure due to their amphipathic properties. In presence of water, they form vesicles, improving the solubility and stability of the active agents once they are loaded into their structure. In addition to phospholipids, other compounds can be added to the formulations, such as cholesterol, which decreases the fluidity of the nanoparticle and increases the permeability of hydrophobic drugs through the bilayer membrane, improving the stability of these nanoparticles in blood. Cholesterol-modified liposomes may present a multiple bilayer with sizes from 0.5-10 nm, as multilaminar vesicles (MHLVs); a single bilayer with sizes above 100 nm, as large unilamellar vesicles (LUVs); and intermediate sizes (10-100 nm), as small unilamellar vesicles (SUVs). Additional liposomal and micelle formulations suitable for pharmaceutical applications can be found, e.g., in U.S. Pat. No. 8,808,734.

In other embodiments, pharmaceutical compositions of the invention may be formulated into a topical dosage form. Topical dosage forms include transmucosal and transdermal formulations, such as aerosols, emulsions, sprays, ointments, salves, gels, pastes, lotions, liniments, oils, and creams. For such formulations, penetrants and carriers can be included in the pharmaceutical composition. Penetrants are known in the art, and include, for transmucosal administration, detergents, bile salts, and fusidic acid derivatives. For transdermal administration, carriers which may be used include Vaseline®, lanolin, PEG, alcohols, transdermal enhancers, and combinations thereof.

An exemplary topical delivery system is a transdermal delivery device ("patch") containing the active agents. Such transdermal patches may be used to provide continuous or discontinuous infusion of the compounds of the present invention in controlled amounts. Such patches may be constructed for continuous, gradual, pulsatile, or on demand delivery of pharmaceutical agents. A "patch" within the meaning of the invention may be simply a medicated adhesive patch, i.e., a patch impregnated with a composition of the invention for application onto the skin. Thus, a patch may be a single-layer or multi-layer drug-in-adhesive patch, wherein the one or more adhesive layers also contain the active agents.

A patch may also be a "matrix" (or "monolithic") patch, wherein the adhesive layer surrounds and overlays the drug layer (wherein a solution or suspension of the active agents is in a semisolid matrix). A "reservoir" patch may also be used, comprising a drug layer, typically as a solution or suspension of the active agents in a liquid compartment (i.e., the reservoir), separate from an adhesive layer. For example, the reservoir may be totally encapsulated in a shallow compartment molded from a drug-impermeable metallic plastic laminate, with a rate-controlling membrane made of vinyl acetate or a like polymer on one surface. A patch also may be part of a delivery system, for instance used with an electronic device communicatively coupled to the mobile device of a user, and coupled with a mobile application (e.g., to control the delivery rate from the reservoir, and optionally to provide information about delivery back to the application or user). Various transdermal patch technologies may be accordingly utilized.

One such transdermal patch technology as herein contemplated comprises a self contained module including a built-in battery that produces a low-level electric current to heat the skin and deliver a prescribed dose of a composition of the invention, wherein a therapeutically effective amount of the composition crosses the skin and enters the underlying tissue, so as to produce a therapeutic effect. Such a transdermal delivery device may, for example, comprise an adhesive layer, a protective film, a drug-containing reservoir (for the pharmaceutical compositions of the invention), a heating coil, a battery, a hardware board, optionally all within a device holder, and optionally, functionally coupled to a device which is able to control drug delivery (e.g., a smartphone) using a downloadable mobile application. Such devices may, for instance, additionally shut off drug delivery automatically when a prescribed dose has been administered, or may shut off automatically upon reaching a certain temperature or defined time. Such transdermal devices may be reusable or disposable.

d. Formulation Examples

By way of non-limiting and merely suggestive example, the following formulations may be used in the methods of the present invention.

Example 1: Formulation of Capsules with 235 mg or 62.5 mg 9:1 R:S MDMA

Gelatin capsules containing the below milligram amounts of an enantiomerically enriched mixture of R-MDMA and S:MDMA in a 9:1 ratio of R:S are made as follows:

| Exemplary 235 mg Capsule | |
|---|---|
| Ingredient | Quantity (mg/capsule) |
| 9:1 R-MDMA:S-MDMA | 235.0 |
| Starch | 73.0 |
| Magnesium stearate | 2.0 |

| Exemplary 62.5 mg Capsule | |
|---|---|
| Ingredient | Quantity (mg/capsule) |
| 9:1 R-MDMA:S-MDMA | 62.5 |
| Starch | 36.5 |
| Magnesium stearate | 1.0 |

MDMA is produced by chemical synthesis through known methods or commercially sourced. The MDMA, starch, and magnesium stearate are blended, passed through a No. 20 mesh U.S. sieve, and filled into size 4 hard or soft gelatin capsules in 200 mg or 100 mg quantities as above.

Example 2: Formulation of Tablets with 125 mg or 62.5 mg R-MDMA

Tablets, each containing the below milligram amounts of an enantiomerically enriched mixture of R-MDMA and S:MDMA in a 10:1 ratio of R:S are made as follows:

| Exemplary 125 mg Tablet | |
| --- | --- |
| Ingredient | Quantity (mg/tablet) |
| 10:1 R-MDMA:S-MDMA | 125.0 |
| Cellulose, microcrystalline | 100.0 |
| Colloidal silicon dioxide | 65.0 |
| Stearic acid | 10.0 |

| Exemplary 62.5 mg Tablet | |
| --- | --- |
| Ingredient | Quantity (mg/tablet) |
| 10:1 R-MDMA:S-MDMA | 62.5 |
| Cellulose, microcrystalline | 50.0 |
| Colloidal silicon dioxide | 32.5 |
| Stearic acid | 5.0 |

The components are blended and compressed to form tablets, weighing 300 mg or 150 mg total.

Example 3: Formulation of Liquid Suspension

Liquid suspensions, each containing the below amounts per 1.0 ml dose are made as follows:

| Ingredient | Amount |
| --- | --- |
| 10:1 R:S MDMA | 125.0 mg |
| Excipient | to 1.0 ml |

R-MDMA can be prepared as described herein, and is measured out, blended, passed through a No. 10 mesh U.S. sieve, and then mixed into a liquid excipient. Liquid suspensions of this Example can be administered directly or used to prepare softgel capsules, ampoules, or other single unit dosage forms, through methods herein disclosed or known to those of skill in the art.

Example 4: Formulation of a Tincture

Tinctures, each containing the below amounts per 1.0 ml dose are made as follows:

| Ingredient | Amount |
| --- | --- |
| 9:1 R:S MDMA | 125.0 mg |
| Sodium carboxymethyl cellulose (11%) | 12.5 mg |
| Microcrystalline cellulose (89%) | 10 mg |
| Sweetener (optional) | 0.35 g |
| Sodium benzoate | 2.5 mg |
| Flavor and Color | q.v. |
| Excipient | to 1.0 ml |

The R-MDMA, optional sweetener (e.g., sucrose or sucralose), and xanthan gum are measured out, blended, passed through a No. 10 mesh U.S. sieve, and then mixed with a previously made solution of microcrystalline cellulose and sodium carboxymethyl cellulose in excipient (e.g., ethanol or purified water). The sodium benzoate, flavor, and color are diluted with excipient and added with stirring.

Example 5: Formulation of Injectable Form

A formulation for injection (e.g., for subcutaneous, intramuscular, intraperitoneal, or intravenous delivery) may be prepared as follows:

| Ingredient | Amount |
| --- | --- |
| 9:1 R:S MDMA | 8 g |
| DMSO | 5 mL |
| Tetraethylene Glycol (TEG) | 500 mL |
| Saline (1% cremophor) | To 1 L |

Active ingredients are dissolved in dimethyl sulphoxide (DMSO) in proportions of 1 g to 0.5 mL. Solution is brought to 37° C. and vortexed for 3-5 minutes. Tetraethyleneglycol (TEG) in an amount of 5 mL is added, and the solution is returned to 37° C. and vortexed again for 3-5 mins. Solution is mixed 1:1 with saline containing 1% cremophor to prevent precipitation. Final solution will be at 10 mg/mL active ingredients in 49.5% TEG, 49.5% saline, 0.5% DMSO, and 0.5% cremophor.

Injection may be by any suitable means, e.g., bolus injection, IV infusion, or subcutaneous infusion, for example using a drug delivery device comprising a reservoir and a pump mechanism, configured for subcutaneous administration, and which may optionally contain a user interface or be coupled to a device with a user interface such as a smartphone.

Example 6: Formulation of Intranasal Delivery Form

A nasal spray formulation for intranasal delivery may be prepared as follows:

| Ingredient | Amount |
| --- | --- |
| 8:1 R:S MDMA | 125 mg |
| DMSO | 62.5 L |
| MCT | 6.25 mL |
| Saline (1% cremophor) | To 12.5 mL |

Solution at 10 mg/mL active ingredients in 49.5% MCT, 49.5% saline, 0.5% DMSO, and 0.5% cremophor is prepared, as above (but with MCT in place of TEG), for use in nasal spray devices. In other embodiments, a nasal formulation can be prepared as a dry powder for inhalation, e.g., by combining the active agents with lactose and mixing for use with a dry powder inhaling appliance, or as in U.S. Pub. No. 2015/0367091A1 and references cited therein.

Example 7: Formulation of Topical Form

A topical formulation may be prepared as follows:

| Ingredient | Amount (g) |
| --- | --- |
| 9:1 R:S MDMA | 20 |
| Emulsifying Wax | 30 |
| Liquid Paraffin | 20 |
| White Soft Paraffin | To 100 |

The white soft paraffin is heated until molten. The active ingredients are added and stirring is continued until dispersed. The liquid paraffin and emulsifying wax are incorporated and stirred until dissolved. The mixture is then cooled until solid.

Example 8: Formulation of Transdermal Delivery Form

A formulation for a transdermal delivery device may be prepared as follows:

| Ingredient | Amount (g) |
| --- | --- |
| 10:1 R:S MDMA | 2 |
| Permeation enhancing agent | 30 |
| Solubilizer | 20 |
| Stabilizer | To 100 |

The stabilizer, solubilizer, and permeation enhancing agent are heated and stirred until combined. The active ingredients are added after partially cooled but before setting and stirring is continued until dispersed. The mixture is then cooled until in its desired final form (e.g., for use in a reservoir delivery system) or admixed with an adhesive and then cooled (e.g., for use in a drug-in-adhesive patch).

It should be readily appreciated that the above formulation examples are illustrative only. Accordingly, any of the compounds may be substituted with the same compound in a different dosage amount. For example, in certain aspects of Example 4, wherein a subtherapeutic or "active" control of 20 or 10 mg is used, capsules may be prepared as in Example 1 (or tablets as in Example 2), but with amounts of the active and inactive ingredients adjusted accordingly.

It will be understood that reference to particular compounds is merely illustrative, and both active and inactive compounds in any Example may be substituted by other compounds of the invention. For example, any MDMA enantiomer or non-racemic mixture thereof, e.g., comprising R-MDMA in enantiomeric excess, described herein and claimed may be substituted in any of the above examples. Moreover, for any of the compounds of the invention (including for either or both of R-MDMA and S-MDMA in an enriched mixture), substitution of the compound by its ion, free base, or salt form, a polymorph or other solid form such as a co-crystal, an amorphous form, or an isomer (e.g., for a racemic compound), shall be understood to provide merely an alternative embodiment still within the scope of the invention (with modifications to the formulation and dosage amounts made according to the teachings herein and ordinary skill). Further, compositions within the scope of the invention should be understood to be open-ended and may include additional active or inactive compounds and ingredients.

In some embodiments, the particle size of the MDMA, other active ingredient(s), or inactive ingredient(s) is reduced. A process to reduce the particle size of an active agent (API) such as MDMA (and including R-MDMA, S-MDMA, and enantiomeric mixtures thereof), while maintaining its polymorphic form, comprising a step of processing the API by cavitation at elevated pressure is described, e.g., in patent application WO2011/131947. For instance, as described there, the API is processed in three steps: (1) it is suspended in an anti-solvent where it is insoluble; (2) it is size-reduced; and (3) it is preferably dried by spray drying to obtain the product as a dry powder, a technique known as wet polishing. Such particle engineering of active agents provides a particle size reduction capable of attaining a target particle size range suitable for performance of drug products.

Another scalable process to control particle size and the particle size distribution of an API to increase its performance in drug products is described in U.S. Pat. No. 10,328,027. There, the process comprises five steps: (1) suspension preparation in a mixture of solvents in which the product of interest is partially soluble in one first solvent and as substantially insoluble in a second solvent; (2) particle size reduction of the product in suspension leading to a size reduction generally below the desired size; (3) a step of aging in which crystallization of the partially dissolved product through temperature control occurs, leading to particle growth to the desired size; (4) stopping the crystallization by solvent removal; and (5) optionally, a step of isolating the processed ingredients in the form of powder.

By such processes, and others as will be known to those of ordinary skill in the art, the particle size of one or more active agents can be reduced, while controlling the particle size distribution. It is known that such processes can be applied to attain precise control of particle size including, but not restricted to amorphous, crystalline, hydrated, or solvated forms of active agents and pharmaceutical acceptable salts thereof prone to polymorphic transformation when using traditional particle size reduction technologies, thereby retaining the polymorphic form.

The type of formulation employed for the administration of the compounds employed in the methods of the present invention generally may be dictated by the compound(s) employed, the type of pharmacokinetic profile desired from the route of administration and the compound(s), and the state of the patient. It will be readily appreciated that any of the above embodiments and classes of embodiments can be combined to form additional embodiments.

C. Route of Administration and Dosage

In some aspects, provided herein are routes of administration for disclosed MDMA enantiomers, non-racemic mixtures thereof, and compositions comprising the same. Also provided are dosing ranges for administration of disclosed MDMA enantiomers and non-racemic mixtures thereof, including compositions comprising the same, to a subject. In some embodiments, the provided non-racemic mixtures or compositions thereof comprise R-MDMA in enantiomeric excess. In some embodiments, the provided non-racemic mixtures or compositions thereof comprise 90% or less of R-MDMA and 10% or more of S-MDMA, or a pharmaceutically acceptable salt thereof. In some embodiments, the provided non-racemic mixtures or compositions thereof comprise R-MDMA in an enantiomeric excess of 10%-95%, 20%-95%, 30%-95%, 40%-95%, 50%-95%, 55%-95%, 60%-90%, 65%-90%, or 75%-85% of R-MDMA. In some embodiments, the provided non-racemic mixtures or compositions thereof comprise R-MDMA in an enantiomeric excess of 10%, 15%, 20%, 25%, 30%, 35%, 40%, 45%, 50%, 55%, 60%, 65%, 70%, 75%, 80%, 85%, 90%, or 95%. In some embodiments, the provided non-racemic mixtures or compositions thereof comprise R-MDMA in an enantiomeric excess of about 75%, 76%, 77%, 78%, 79%, 80%, 81%, 82%, 83%, 84%, or 85%. In some embodiments, the provided non-racemic mixtures or compositions thereof comprise R-MDMA in an enantiomeric excess of about 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1%. In some embodiments, the provided non-racemic mixtures or compositions thereof comprise R-MDMA in an enantiomeric excess of about 79.5%, 79.6%, 79.7%, 79.8%, 79.9%, 80%, 80.1%, 80.2%, 80.3%, 80.4%, or 80.5%. In some embodiments, the provided non-racemic mixtures or compositions thereof comprise 6:1 to 12:1, 7:1 to 11:1, or 8:1 to 10:1 R:S MDMA. In some embodiments, the provided non-racemic mixtures or compositions thereof comprise 6:1, 7:1, 8:1, 9:1, or 10:1 R:S MDMA.

a. Route of Administration

The compounds and compositions described herein can be formulated for administration to a subject via any conventional means including, but not limited to, oral, parenteral, e.g., intravenous, subcutaneous, or intramuscular, buccal, intranasal, rectal or transdermal administration routes. As used herein, the term "subject" is used to mean an animal, preferably a mammal, including a human or non-human. The terms patient and subject may be used interchangeably.

The present invention provides methods for using therapeutically effective amounts of the pharmaceutical compositions and formulations of the present invention in a mammal, and preferably a human. Such methods include those for modulating neurotransmission and for treating a disorder, such as a mental health disorder, including mood disorders and PTSD, and substance abuse disorders. The dosage may vary within the provided ranges depending upon the dosage form employed and the route of administration utilized.

b. Dosing

The active compounds described herein, such as MDMA enantiomers and non-racemic mixtures thereof, e.g., comprising R-MDMA in enantiomeric excess, are effective over a wide dosage range, and will differ depending on the condition of the patient, the disorder to be treated, and such other factors as discussed herein and known to those of ordinary skill. Generally, dosages will fall within the range of about 0.01 mg/kg to about 15 mg/kg, with preferred dosages normally in the range of about 1 mg/kg to about 2.5 mg/kg or 6 mg/kg to 8 mg/kg, such as about 7 mg/kg. In some embodiments, a disclosed compound is administered to a subject in an amount of about 3 mg/kg-10 mg/kg, 5 mg/kg-8 mg/kg, or 6 mg/kg-7 mg/kg. In some embodiments, a disclosed compound is administered to a subject in an amount of 3 mg/kg, 4 mg/kg, 5 mg/kg, 6 mg/kg, 7 mg/kg, 8 mg/kg, 9 mg/kg, or 10 mg/kg.

Table 1 shows doses of MDMA having no adverse effect level (NOAEL) from the literature, their calculated human equivalent dose (TIED), and maximum recommended starting dose (MRSD). Exemplary dosing is additionally provided for the disclosed compounds, as exemplified by 9:1 R:S MIDMA.

TABLE 1

No adverse effect level (NOAEL) doses of MDMA and enantiomers thereof

| Compound | No adverse effect level (NOAEL) | Human Equivalent Dose (HED) | Maximum Recommended Starting Dose (MRSD) |
|---|---|---|---|
| SR(±)MDMA | NOAEL: 100 mg/kg (p.o.) in rat with single housing$_1$<br>NOAEL: 15 mg/kg in dog (p.o.)$_1$<br>Neurotoxicology: in rat:<br>(♀) NOAEL: 25 mg/kg/week p.o$_1$<br>(♂) NOAEL: 20 mg/kg/week p.o$_1$.<br>in dog:<br>(♀, ♂) NOAEL: 4 mg/kg/week p.o | NOAEL (human): 34 mg/kg → 2080 mg*<br>Neurotoxicology: NOAEL (human): 6 mg/kg → 342.9 mg* | 80 mg-120 mg initial dose MDMA HCl<br>40 mg-60 mg supplemental dose MDMA HCl<br>Maximum proposed dose: 125 mg<br>Maximum tested single dose: 150 mg |
| R(−)MDMA | NOAEL: >200 mg/kg (p.o) in rat$_3$<br>Neurotoxicology: NOAEL: in rat: 50 mg/kg i.v$_2$ | NOAEL (human): >68 mg/kg → >4100 mg<br>Neurotoxicology: NOAEL (human): 7.4 mg/kg → 450 mg* | Expected MSRD: >300 mg:<br>62.5 mg tested in humans |
| S(+)MDMA | Expected: <100 mg/kg (p.o) in rat$_3$<br>Neurotoxicology: NOAEL: in rat: 20 mg/kg i. V$_{2,3}$ | NOAEL (human): → <34 mg/kg → <2080 mg*<br>Neurotoxicology: NOAEL (human): 6 mg/kg → 342.9 mg* | Expected MSRD: 150 mg<br>62.5 mg tested in humans |

TABLE 1-continued

No adverse effect level (NOAEL) doses of MDMA and enantiomers thereof

| Compound | No adverse effect level (NOAEL) | Human Equivalent Dose (HED) | Maximum Recommended Starting Dose (MRSD) |
|---|---|---|---|
| Exemplary Compound 9:1 R:S MDMA | Expected >100 mg/kg (p.o) in rat (p.o) Neurotoxicology: Expected NOAEL: in rat: >40 mg/kg (i.v) | Expected NOAEL (human): >64 mg/kg → >3800 mg* (p.o) Neurotoxicology: NOAEL (human): >7.2 mg/kg → >440 mg* (i.v) | Expected MSRD: >280 mg Safest validated MPSD dose (Phase I): 62 mg Proposed clinical dosing range: 141 mg-285 mg single dose 9:1 R:S MDMA |

*Assuming a 60 kg human.
1(MAPS, 2884-005, 2021),
2(Curry et al., Neuropharmacology, 2018; 128:196-206),
3(Fantegrossi et al., Psychopharmacology (Berl)., 2003; 166(3):202-11).

In embodiments, the disclosed pharmaceutical compositions comprise therapeutic amounts of R-MDMA, S-MIDMA, or non-racemic mixtures thereof, and may additionally include other active or inactive ingredients. In embodiments, where a pharmaceutical composition includes R-MDMA, S-MIDMA, or a non-racemic mixture thereof, it may be present in an amount so that a single dose is (whether or not such dose is in a unit dosage form), e.g., 5 mg or less, at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 105 mg, at least 110 mg, at least 115 mg, at least 120 mg, at least 125 mg, at least 130 mg, at least 135 mg, at least 140 mg, at least 145 mg, at least 150 mg, at least 155 mg, at least 160 mg, at least 165 mg, at least 170 mg, at least 175 mg, at least 180 mg, at least 185 mg, at least 190 mg, at least 195 mg, at least 200 mg, at least 205 mg, at least 210 mg, at least 215 mg, at least 220 mg, at least 225 mg, at least 230 mg, at least 235 mg, at least 240 mg, at least 245 mg, at least 250 mg, at least 255 mg, at least 260 mg, at least 265 mg, at least 270 mg, at least 275 mg, at least 280 mg, at least 285 mg, at least 290 mg, at least 295 mg, at least 300 mg, at least 305 mg, at least 310 mg, at least 315 mg, at least 320 mg, or at least 325 mg, as well as amounts within these ranges.

In some embodiments, a dose of R-MDMA, S-MDMA, or a non-racemic mixture thereof, such as comprising R-MDMA in enantiomeric excess will be between 25 mg and 325 mg, 25 mg and 175 mg, more preferably between 50 mg and 150 mg, and most preferably between 62 mg to 62.5 mg and 125 mg, inclusive. In some embodiments, a dose of R-MDMA, S-MDMA, or a non-racemic mixture thereof, such as comprising R-MDMA in enantiomeric excess for administration to a subject is in an amount of about 50 mg to 300 mg, 75 mg to 300 mg, 100 mg to 300 mg, or 140 mg to 285 mg. In some embodiments, a dose of R-MDMA, S-MDMA, or a non-racemic mixture thereof, such as comprising R-MDMA in enantiomeric excess for administration to a subject is in an amount of about 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, or 75 mg.

In some embodiments, a dose of R-MDMA, S-MDMA, or a non-racemic mixture thereof, such as comprising R-MDMA in enantiomeric excess, is about 141 mg. In some embodiments, a dose of about less than 200 mg is referred to as a low dose regimen. In some embodiments, a dose of R-MDMA, S-MDMA, or a non-racemic mixture thereof, such as comprising R-MDMA in enantiomeric excess, is about 235 mg. In some embodiments, a dose of about 200 mg to 250 mg is referred to as a medium dose regimen, In some embodiments, a dose of R-MDMA, S-MDMA, or a non-racemic mixture thereof, such as comprising R-MDMA in enantiomeric excess, is 285 mg. In some embodiments, a dose of at least 275 mg is referred to as a high dose. In some embodiments, a provided dose is administered to a subject in separated doses. In some embodiments, an MDMA-assisted psychotherapy regime of two doses of R-MDMA, S-MDMA, or a non-racemic mixture thereof is used, with an initial dose of 125 mg and a "booster" dose of 62.5 mg taken, for example, two hours later. In some embodiments, a provided dose of a disclosed compound is orally administered to a subject in need thereof.

In the case of treating PTSD, the method may comprise administering a high dosage of R-MDMA, S-MDMA, or non-racemic mixtures thereof, wherein a high dosage is defined as being greater than about 2 mg/kg. In some embodiments, a disclosed compound is administered to a subject, such as a subject having PTSD, in an amount of about 3 mg/kg-10 mg/kg, 5 mg/kg-8 mg/kg, or 6 mg/kg-7 mg/kg. In some embodiments, a disclosed compound is administered to a subject, such as a subject having PTSD, in an amount of 3 mg/kg, 4 mg/kg, 5 mg/kg, 6 mg/kg, 7 mg/kg, 8 mg/kg, 9 mg/kg, or 10 mg/kg. The administration may happen a limited number of times, as determined necessary by a clinical psychiatrist. For example, the method may comprise less than 5 administrations, such as a one time administration. Administering the R-MDMA, S-MDMA, or non-racemic mixtures thereof may be done orally, sublingually, or intravenously/intramuscularly.

By way of example, some embodiments of the invention include a composition and method for treating PTSD and mood disorders, such as major depressive disorder (MDD). The method may comprise administering a therapeutically effective dose of R-MDMA, S-MDMA, or non-racemic mixtures thereof to a patient in need, wherein the therapeutically effective dosage may be dependent on the disorder being treated.

When treating mood disorders, such as MDD, the method may comprise administering a medium to low dose of R-MDMA, S-MDMA, or non-racemic mixtures thereof, wherein a medium to low dose is defined as being about 0.5 mg/kg to about 2 mg/kg. The administration may happen based on a higher/chronic administration timetable, as determined necessary by a clinical psychiatrist. For example, the method may comprise regularly administering the R-MDMA, S-MDMA, or non-racemic mixtures thereof at a high frequency, such as about once a week.

In some embodiments, a therapeutically effective dose of an MDMA enantiomer or non-racemic mixtures thereof, such as comprising R-MDMA in enantiomeric excess, is administered to a subject once every week, once every two weeks, once every three weeks, once every four weeks, once every five weeks, or once every six weeks. In some embodiments, one, two, three, four, five, six, seven, eight, nine, ten, eleven, or twelve therapeutically effective dose(s) of an MDMA enantiomer or non-racemic mixtures thereof, such as comprising R-MDMA in enantiomeric excess, is/are administered over the course of a treatment period, e.g., one dose every four weeks over an eight week treatment period for a total of two doses, one dose every three weeks over a nine week treatment period for a total of three doses, one dose every two weeks over a ten week period for a total of five doses. In some embodiments, a therapeutically effective dose of an MDMA enantiomer or non-racemic mixtures thereof, such as comprising R-MDMA in enantiomeric excess, is administered to a subject once a month, once every two months, once every three months, or once every four months. In some embodiments, a provided non-racemic mixture of MDMA is orally administered. In some embodiments, a provided non-racemic mixture comprises R-MDMA HCl and S-MDMA HCl in a ratio of 9:1. In some embodiments, R-MDMA HCl and S-MDMA HCl in a ratio of 9:1 is orally administered to a subject in need thereof.

While treating MDD and PTSD are described above, other disorders also may be treated using the administration of R-MDMA, S-MDMA, or non-racemic mixtures thereof, such as a mental health disorder and/or a substance abuse disorder. For example, in some embodiments wherein a method of managing emotional regulation in a patient are disclosed, the patient may be administered a pharmaceutical formulation at a low (or a "micro" dose, defined herein as an amount less than about 0.5 mg/kg), and in certain preferred embodiments, a controlled release, sustained release, extended release, delayed release, or modified release formulation will be administered. In some embodiments, a patient in need of managing emotional regulation will be a patient having at least one of a stress disorder, acute stress disorder, brief psychotic disorder with marked stressor(s), delirium, mild cognitive impairment (MCI), dementia, psychosis, psychotic major depression, autism, and psychological distress related to life-threatening illness or death. In some such embodiments, the patient will be in long-term or institutional care, such as a group home, nursing home, residential care facility, long-stay hospital, and the like.

The therapeutically effective dosages may also vary outside of the amounts described herein, depending on the individual patient. Generally, the pharmaceutical compositions of the invention may be administered and dosed in accordance with good medical practice, taking into account the method and scheduling of administration, prior and concomitant medications and medical supplements, the clinical condition of the individual patient and the severity of the underlying disease, the patient's age, sex, body weight, and other such factors relevant to medical practitioners, and knowledge of the particular compound(s) used. Starting and maintenance dosage levels thus may differ from patient to patient, for individual patients across time, and for different pharmaceutical compositions, but shall be able to be determined with ordinary skill.

In some embodiments, a provided non-racemic mixture for administration to a subject comprises 90% or less of R-MDMA and 10% or more of S-MDMA. In some embodiments, a provided non-racemic mixture for administration to a subject comprises R-MDMA in an enantiomeric excess of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%. In some embodiments, a provided non-racemic mixture for administration to a subject comprises R-MDMA in an enantiomeric excess of 10%-95%, 20%-95%, 30%-95%, 40%-95%, 50%-95%, 55%-95%, 60%-90%, 65%-90%, or 75%-85%, wherein each range is inclusive. In some embodiments, a provided non-racemic mixture for administration to a subject comprises R-MDMA in an enantiomeric excess of 10%, 15%, 20%, 25%, 30%, 35%, 40%, 45%, 50%, 55%, 60%, 65%, 70%, 75%, 80%, 85%, 90%, or 95%. In some embodiments, a provided non-racemic mixture for administration to a subject comprises R-MDMA in an enantiomeric excess of 75%, 76%, 77%, 78%, 79%, 80%, 81%, 82%, 83%, 84%, or 85%. In some embodiments, a provided non-racemic mixture for administration to a subject comprises R-MDMA in an enantiomeric excess of 79% to 81%, 79.1% to 80.9%, 79.2% to 80.8%, 79.3% to 80.7%, 79.4% to 80.6%, 79.5% to 80.5%, 79.6% to 80.4%, 79.7% 80.3% 79.8% to 80.2%, or 79.9% to 80.1%. In some embodiments, a provided non-racemic mixture for administration to a subject comprises R-MDMA in an enantiomeric excess of 79.5%, 79.6%, 79.7%, 79.8%, 79.9%, 80%, 80.1%, 80.2%, 80.3%, 80.4%, or 80.5%. In some embodiments, a provided non-racemic mixture for administration to a subject comprises R-MDMA and S-MDMA in a ratio of about 6:1 to 12:1, 7:1 to 11:1, or 8:1 to 10:1, wherein each range is inclusive. In some embodiments, a provided non-racemic mixture for administration to a subject comprises 6:1, 7:1, 8:1, 9:1, 10:1, 11:1, or 12:1 R:S MDMA. In some embodiments, a provided non-racemic mixture for administration to a subject comprises 9:1 R:S MDMA.

c. Pharmacokinetics and Pharmacodynamics

In some embodiments, the disclosed MDMA enantiomers and non-racemic mixtures thereof, such as comprising R-MDMA in enantiomeric excess, display improved pharmacokinetics. Improved pharmacokinetics include, e.g., a reduced duration of action and faster clearance. In some embodiments, a non-racemic mixture comprising R-MDMA in enantiomeric excess displays reduced duration of action relative to racemic MDMA and/or R-MDMA. In some embodiments, a non-racemic mixture comprising R-MDMA in enantiomeric excess displays faster clearance relative to racemic MDMA and/or R-MDMA. In embodiments, clearance is increased by at least 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, or at least 200% relative to racemic MDMA and/or R-MDMA. In some embodiments, clearance is determined in vitro, for example by a liver microsomes study. See, e.g., Knights et al., Curr Protoc Pharmacol., 2016; 74:7.8.1-7.8.24; Obach, Curr Opin Drug Discov Devel., 2001; 4(1):36-44; Gollamundi et al., Neurotoxicol, 1989; 10(3):455-66. In some embodiments, clearance is determined in vivo, for example, by a pharmacokinetic study. See, e.g., R de la Torre et al., Br J Clin Pharmacol., 2000; 49(2): 104-109.

In some embodiments, a single dose of a non-racemic mixture comprising R-MDMA in enantiomeric excess displays reduced duration of action and faster clearance relative to a two-dose regimen of racemic MDMA, wherein the single dose of the non-racemic mixture exceeds the total dose of the two-dose regimen of racemic MDMA. In some embodiments, the single dose of the non-racemic mixture comprising R-MDMA in enantiomeric excess exceeds the total dose of the two-dose regimen of racemic MDMA by at least 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, or at least 200%. In some embodiments, a two-dose regimen of MDMA comprises an initial dose of 125 mg and a subsequent ("booster") dose of 62.5 mg. In some embodiments, the initial dose and the subsequent dose are separated by about 0.5 hr, 1 hr, 1.5 hr, 2 hrs, 2.5 hrs, 3 hrs, 3.5 hrs, or 4 hrs.

In comparison to S-MDMA, the R-enantiomer has been found to display an increased AUC and a longer half-life (Fallon et al., Clin Chem., 1999; 45(7):1058-69; Fitzgerald et al., Chirality, 1990; 2(4):241-8). Regarding racemic MDMA, doses ranging from 100-125 mg reached peak plasma concentration in humans after 2-3 hours. In patients with PTSD administered this dosing regime, onset of action occurred 45-75 minutes after the initial dose and peak drug effects were reported at 2-5 hours (Mithoefer et al., J Psychopharmacol, 2013; 27(1): 28-39). For those receiving one dose, the effects lasted 4-5 hours, which was extended with the booster dose to 5-6 hours. In a prior study, subjective effects were reported after approximately 45 mins, peaking around 1.5-2 hours, and decreasing to baseline values 5-6 hours later (Harris et al., Psychopharmacology, 2002; 162, 396-405). The elimination half-life of MDMA is between 7-9 hours, with similar results for doses ranging from 50-125 mg (Mas et al., J Pharmacol Exp. Ther., 1999; 290(1):136-45). In brain imaging studies, peak subjective effects have been reported at 100 mins and have lasted approximately 4.5 hours after 100 mg MDMA in healthy volunteers (Carhart-Harris & Nutt, Journal of Psychoactive Drugs, 2013; 45(4): 322-328).

i. Metabolism

In some embodiments, a provided MDMA enantiomer or non-racemic enantiomeric mixture comprising R-MDMA in enantiomeric excess has reduced affinity for a cytochrome P450 isoform. In some embodiments, a non-racemic enantiomeric mixture of R-MDMA and S-MDMA comprising R-MDMA in an enantiomeric excess of 10%-95%, 20%-95%, 30%-95%, 40%-95%, 50%-95%, 55%-95%, 60%-90%, 65%-90%, or 75%-85%, has reduced affinity for a cytochrome P450 isoform. In some embodiments, a non-racemic enantiomeric mixture of R-MDMA and S-MDMA comprising R-MDMA in an enantiomeric excess of 10%, 15%, 20%, 25%, 30%, 35%, 40%, 45%, 50%, 55%, 60%, 65%, 70%, 75%, 80%, 85%, 90%, or 95% has reduced affinity for a cytochrome P450 isoform. In some embodiments, a non-racemic enantiomeric mixture comprising R-MDMA in an amount of about 6:1, 7:1, 8:1, 9:1, 10:1, 11:1, or 12:1 has reduced affinity for a cytochrome P450 isoform. In some embodiments, the cytochrome P450 isoform is selected from the group consisting of CYP2C8, CYP2C9, CYP2C19, and CYP2D6. In some embodiments, reduced affinity is determined relative to a comparator. In some embodiments, the comparator is S-MDMA. In some embodiments, the comparator is racemic MDMA. Methods for measuring metabolism in vitro are known in the art, including, e.g., liver microsomal stability assays and in vitro metabolism with human cytochrome P450 enzymes. See, e.g., U.S. application Ser. No. 11/890,255 (Pub. No. US20080045588A1).

In some embodiments, administration of a provided MDMA enantiomer or non-racemic enantiomeric mixture comprising R-MDMA in enantiomeric excess to a subject results in decreased metabolism by at least one polymorphically-expressed cytochrome P450 isoform in the subject, as compared to racemic MDMA. In some embodiments, administration of a provided MDMA enantiomer or non-racemic enantiomeric mixture comprising R-MDMA in enantiomeric excess to a subject suffering from and/or diagnosed with PTSD results in decreased metabolism by at least one polymorphically-expressed cytochrome P450 isoform in the subject, as compared to racemic MDMA. In some embodiments, administration of a non-racemic enantiomeric mixture comprising R-MDMA in an amount of about 6:1, 7:1, 8:1, 9:1, 10:1, 11:1, or 12:1 to a subject suffering from and/or diagnosed with a mental health disorder results in decreased metabolism by at least one polymorphically-expressed cytochrome P450 isoform in the subject, as compared to racemic MDMA. In some embodiments, the cytochrome P450 isoform is selected from the group consisting of CYP2C8, CYP2C9, CYP2C19, and CYP2D6. In some embodiments, the mental health disorder is PTSD.

In some embodiments, administration of a provided MDMA enantiomer or non-racemic enantiomeric mixture comprising R-MDMA in enantiomeric excess to a subject results in decreased average plasma levels of at least one metabolite of MDMA per dosage unit thereof, as compared to racemic MDMA. In some embodiments, administration of a provided MDMA enantiomer or non-racemic enantiomeric mixture comprising R-MDMA in enantiomeric excess to a subject suffering from and/or diagnosed with a mental health disorder results in decreased average plasma levels of at least one metabolite of MDMA per dosage unit thereof, as compared to racemic MDMA. In some embodiments, administration of a non-racemic enantiomeric mixture comprising R-MDMA in an amount of about 6:1, 7:1, 8:1, 9:1, 10:1, 11:1, or 12:1 to a subject suffering from and/or diagnosed with a mental health disorder results in decreased average plasma levels of at least one metabolite of MDMA per dosage unit thereof, as compared to racemic MDMA. In some embodiments, the metabolite is MDA. In some embodiments, the metabolite is HHMA. In some embodiments, the metabolite is HMMA. In some embodiments, the mental health disorder is PTSD.

Enantiospecific analyses have determined that the disposition of MDMA, such as the absorption, distribution, metabolism, and excretion, in humans is stereoselective. Regarding metabolism, the different pharmacokinetic properties of the MDMA enantiomers may be caused by enantioselective metabolism by CYP2C19 and CYP2D6. The S-enantiomer has a higher affinity for CYP2D6, a major CYP450 isoenzyme in the metabolism of MDMA, and CYP2C19 preferentially metabolizes S-MDMA (Pizarro et al., J Anal Toxicol., 2002; 26(3):157-65; Maurer, Ther Drug Monit., 1996; 18(4):465-70; Meyer et al., Drug Metab Dispos., 2008; 36(11):2345-54; Tucker et al., Biochem Pharmacol., 1994; 47(7):1151-6).

MDMA and its metabolites can pose safety risks associated with toxicity, such as neurotoxicity. Side effects range in severity and include but are not limited to elevation in heart rate and blood pressure, hyperthermia, and hepatic toxicity (Kalant, CMAJ, 2001; 165(7), 917-928). Major metabolites of MDMA include 3,4-methylenedioxyamphetamine (MDA), 4-hydroxy-3-methoxy-methamphetamine (HMMA) and 4-hydroxy-3-methoxy-amphetamine (HMA). In some embodiments, a toxic metabolite of MDMA is MDA. MDMA is mainly metabolized in the liver, where several different enzymes play a role in its metabolism, including CYP2D6 (Tucker et al., Biochemical Pharmacol, 1994; 47(7): 1151-1156; de la Torre et al., Frontiers In Genetics, 2012; 3:235).

High interpatient variability is also implicated with MDMA use, as such enzymes may be saturated at relatively low levels of the drug. Non-linearity in MDMA pharmacokinetics has been identified, and a small increase in dose of the drug has been shown to translate into a disproportionately high increase in plasma concentration (de la Torre et al., British Journal of Clinical Pharmacology, 2000; 49(2), 104-109). Additionally, some MDMA metabolites, such as MDA, retain pharmacological activity and extend the duration of action, which can increase the likelihood of toxicity.

The catechol moieties of MDMA and certain metabolites thereof, such as MDA, are postulated to be inherently reactive. Downstream effects of such reactivity include generation of reactive oxygen species, reactive nitrogen species, and other toxic byproducts (Carvalho et al., Curr Pharm Biotechnol. 2010; 11(5):476-95). In one example, catechol metabolites induced significant toxicity in rat cardiomyocytes. The toxic effects were characterized by a loss of normal cell morphology, which was preceded by a loss of GSH homeostasis due to conjugation of GSH with N-Me-α-MeDA and α-MeDA, sustained increase of intracellular Ca2+ levels, ATP depletion, and decreases in the antioxidant enzyme activities (Carvalho et al., Chem Res Toxicol. 2004; 17(5):623-32). The results obtained in these studies provide evidence that metabolism of MDMA is required for the expression of MDMA-induced cardiotoxicity in vitro. Accordingly, the prevention or reduction of MDMA metabolism may decrease interpatient variability, decrease drug-drug interactions, decrease the necessary $C_{max}$, and increase $T_{1/2}$. Analysis of MDMA metabolites is additionally described in, e.g., Helmlin et al., J Anal Toxicol., 1996; 20(6):432-40.

ii. Toxicity

In embodiments, administration of a provided MDMA enantiomer or non-racemic enantiomeric mixture comprising R-MDMA in enantiomeric excess to a subject does not increase the subject's body temperature or does not increase the subject's body temperature by more than 0.1° C., 0.2° C., or 0.3° C. In embodiments, administration of a non-racemic enantiomeric mixture of R-MDMA and S-MDMA comprising R-MDMA in an enantiomeric excess of 10%-95%, 20%-95%, 30%-95%, 40%-95%, 50%-95%, 55%-95%, 60%-90%, 65%-90%, or 75%-85%, to a subject does not increase the subject's body temperature or does not increase the subject's body temperature by more than 0.1° C., 0.2° C., or 0.3° C. In some embodiments, administration of a non-racemic enantiomeric mixture of R-MDMA and S-MDMA comprising R-MDMA in an enantiomeric excess of 10%, 15%, 20%, 25%, 30%, 35%, 40%, 45%, 50%, 55%, 60%, 65%, 70%, 75%, 80%, 85%, 90%, or 95% to a subject does not increase the subject's body temperature or does not increase the subject's body temperature by more than 0.1° C., 0.2° C., or 0.3° C. In some embodiments, administration of a non-racemic enantiomeric mixture comprising R-MDMA in an amount of about 6:1, 7:1, 8:1, 9:1, 10:1, 11:1, or 12:1 to a subject does not increase the subject's body temperature or does not increase the subject's body temperature by more than 0.1° C., 0.2° C., or 0.3° C.

In some embodiments, administration of a provided MDMA enantiomer or non-racemic enantiomeric mixture comprising R-MDMA in enantiomeric excess to a subject does not result in hyperthermia. In some embodiments, administration of a non-racemic enantiomeric mixture of R-MDMA and S-MDMA comprising R-MDMA in an enantiomeric excess of 10%-95%, 20%-95%, 30%-95%, 40%-95%, 50%-95%, 55%-95%, 60%-90%, 65%-90%, or 75%-85%, to a subject does not result in hyperthermia. In some embodiments, administration of a non-racemic enantiomeric mixture of R-MDMA and S-MDMA comprising R-MDMA in an enantiomeric excess of 10%, 15%, 20%, 25%, 30%, 35%, 40%, 45%, 50%, 55% 60%, 65%, 70%, 75%, 80%, 85%, 90%, or 95% to a subject does not result in hyperthermia. In some embodiments, administration of a non-racemic enantiomeric mixture comprising R-MDMA in an amount of about 6:1, 7:1, 8:1, 9:1, 10:1, 11:1, or 12:1 does not result in hyperthermia. In some embodiments, the subject suffers from or is diagnosed with a mental health disorder. In some examples, hyperthermia is defined as a temperature of greater than 38.0° C.

A key pharmacological difference between R(−)-MDMA and racemic (±)-MDMA is that R(−)-MDMA has much lower potency as a dopamine releaser, and dopamine signaling has been implicated in hyperthermia (Curry et al., Neuropharmacology, 2018; 128, 196-206). Human hyperthermia associated with ingestion of MDMA is described in Liechti, Temperature (Austin), 2014; 1(3): 192-200. In rhesus monkeys, racemic MDMA has been shown to significantly impact core body temperature at a range of environmental temperatures (Von Huben 2007; Crean 2007). While a direct examination of core body temperature changes under the influence of the individual enantiomers of MDMA has not yet been performed in rhesus monkeys, strong evidence from Curry et. al. demonstrates that there are no significant temperature fluctuations in rodent models even under doses of R(−)-MDMA which are far above the allometrically-scaled clinical doses to be used in humans (Curry et al., Neuropharmacology, 2018; 128, 196-206).

Adverse events associated with administration of MDMA include muscle tightness, decreased appetite, nausea, hyperhidrosis, feeling cold, transient increases in systolic and diastolic blood pressure, and increases in body temperature, such as hyperthermia (Mitchell et al., Nat Med., 2021; 27(6):1025-1033). Additional side effects associated with ingestion of MDMA include tachycardia, oxidative stress, and neurotoxicity. See, e.g., Kalant, CMAJ, 2001; 165(7), 917-928; Carvalho et al., Curr Pharm Biotechnol. 2010; 11(5):476-95.

MDMA appears to produce damage to the serotonergic axon terminals in the striatum, hippocampus, and prefrontal cortex (Battaglia, G., et al., J Pharmacol Experimental Ther. 1987; 242.3: 911-916). As a result, lower expression levels of tryptophan hydroxylase (the rate limiting enzyme involved in serotonin synthesis) and 5-HT (serotonin itself) are found in rodents after a series of heavy doses of MDMA, as well as lower levels of DAT and SERT expression, which are dopamine and serotonin transporters respectively (Commins, D. L., et al., J Pharmacol Experimental Ther. 1987; 241.1: 338-345). Furthermore, some studies have shown MDMA-associated apoptosis (cell death) in cortical neurons (Capela et al., Neurotoxicol. 2007; 28.4: 868-875).

In rodent studies, R(−)-MDMA was determined to be less potent in inducing neurotoxicity, whereas S(+)-MDMA was shown to be involved in the astroglial and microglial activation induced by SR(±)-MDMA (Frau et al., J. Neurochem., 2013; 124(1):69-78). Repeated administration of R(−)-MDMA (50 mg/kg bw) did not show evidence of neurotoxicity in mice even when administered at a high repeated dose relative to SR(±)-MDMA (20 mg/kg bw) (Curry et al., Neuropharmacology, 2018; 128, 196-206). Additionally, racemic MDMA and S(+)-MDMA have been shown to increase dopamine levels, whereas this effect has not been observed with R(−)-MDMA (Curry et al., Neuropharmacology, 2018; 128, 196-206; Johnson et al., European Journal of Pharmacology, 1986; 132:269-276). Studies have shown that the neurotoxic effects of MDMA are primarily dopamine dependent (Granado et al., Neurotox Res., 2014; 25(1):100-9; Squire et al., Neurobiol Learn Mem., 2020; 176: 107322). Together, such effects may contribute to the lower potential of neurotoxicity of a provided non-racemic mixture of MDMA comprising R-MDMA in enantiomeric excess.

iii. Behavioral Effects

In some embodiments, administration of a provided MDMA enantiomer or non-racemic enantiomeric mixture comprising R-MDMA in enantiomeric excess to a subject results in reduced potential for abuse. In some embodiments, administration of a non-racemic enantiomeric mixture of R-MDMA and S-MDMA comprising R-MDMA in an enantiomeric excess of 10%-95%, 20%-95%, 30%-95%, 40%-95%, 50%-95%, 55%-95%, 60%-90%, 65%-90%, or 75%-85%, results in a reduced potential for abuse. In some embodiments, administration of a non-racemic enantiomeric mixture of R-MDMA and S-MDMA comprising R-MDMA in an enantiomeric excess of 10%, 15%, 20%, 25%, 30%, 35%, 40%, 45%, 50%, 55%, 60%, 65%, 70%, 75%, 80%, 85%, 90%, or 95% results in a reduced potential for abuse. In some embodiments, administration of a non-racemic enantiomeric mixture comprising R-MDMA and S-MDMA in a ratio of about 6:1, 7:1, 8:1, 9:1, 10:1, 11:1, or 12:1 to a subject results in reduced potential for abuse. In some embodiments, reduced potential for abuse is determined relative to a comparator. In some embodiments, the comparator is racemic MDMA. In some embodiments, the comparator is S-MDMA. In some embodiments, the subject suffers from or is diagnosed with a mental health disorder.

Abuse potential may be evaluated by methods known in the art, including, e.g., reinforcement studies. Research has demonstrated that MDMA can function as a positive reinforcer in monkeys and rats, and the abuse potential of MDMA in humans is known (Heifets et al., Sci Transl Med., 2019; 11 (522): eaaw6435; Zhou et al., Free Radic Res., 2003; 37(5):491-7). The reinforcing strength of racemic MDMA appears to be driven primarily by S(+)-MDMA (Wang & Woolverton, Psychopharmacology (Berl), 2007; 189(4):483-8). The potential reinforcing effects of a non-racemic form of MDMA, for example, a 9:1 ratio of the R:S enantiomers, is expected to be weaker than for racemic MDMA.

In some embodiments, administration of a provided MDMA enantiomer or non-racemic enantiomeric mixture comprising R-MDMA in enantiomeric excess to a subject results in reduced tolerance. In some embodiments, administration of a provided MDMA enantiomer or non-racemic enantiomeric mixture comprising R-MDMA in enantiomeric excess to a subject results in reduced tolerance. In some embodiments, administration of a non-racemic enantiomeric mixture of R-MDMA and S-MDMA, comprising R-MDMA in an enantiomeric excess of 10%-95%, 20%-95%, 30%-95%, 40%-95%, 50%-95%, 55%-95%, 60%-90%, 65%-90%, or 75%-85%, to a subject results in reduced tolerance. In some embodiments, administration of a non-racemic enantiomeric mixture of R-MDMA and S-MDMA, comprising R-MDMA in an enantiomeric excess of 10%, 15%, 20%, 25%, 30%, 35%, 40%, 45%, 50%, 55%, 60%, 65%, 70%, 75%, 80%, 85%, 90%, or 95% to a subject results in reduced tolerance. In some embodiments, administration of a non-racemic enantiomeric mixture comprising R-MDMA in an amount of about 6:1, 7:1, 8:1, 9:1, 10:1, 11:1, or 12:1 to a subject results in reduced tolerance. In some embodiments, reduced tolerance is determined relative to a comparator. In some embodiments, the comparator is racemic MDMA. In some embodiments, the comparator is S-MDMA. In some embodiments, the subject suffers from or is diagnosed with a mental health disorder.

Reduced subjective efficacy, following repeated usage of MDMA has been described, and many users subjectively report developing tolerance (Parrott, J Psychopharmacol., 2005; 19(1):71-83). The development of tolerance to MDMA may lead to dangerous dose escalation. In rodents, hyperthermia and 5-HT depletion have been implicated in the development of tolerance associated with high-dose binges. Tolerance and behavioral sensitization studies are described in, e.g., Baumann et al., Neuroscience, 2008; 152(3): 773-784; Kalivas et al., Neuropsychopharmacology, 1998; 18(6):469-79; Brennan & Schenk, Psychopharmacology (Berl), 2006; 184(2):239-46; McClung et al., Psychopharmacology (Berl), 2010; 210(1): 75-83.

It will be readily appreciated that dosages may vary depending upon the treatment protocol itself, the onset, progression, severity, frequency, duration, probability of, or susceptibility of the symptom to which treatment is directed, clinical endpoint desired, previous, simultaneous or subsequent treatments, general health, age, gender, and race of the subject, bioavailability, potential adverse systemic, regional, or local side effects, the presence of other disorders or diseases in the subject, and other factors that will be appreciated by the skilled artisan (e.g., medical or familial history). For example, the upper age range of subjects may be limited, e.g., to 65 years, and patients may be screened for cardiac abnormalities, and for medications that may affect the metabolism of R-MDMA (e.g., through CYP1A2, CYP2D6, CYP2C19, and CYP3A4).

In some embodiments, dose amount, frequency or duration may be increased or reduced, as indicated by the clinical outcome desired, status of the pathology or symptom, any adverse side effects of the treatment or therapy, or concomitant medications. For example, as MDMA at doses of 100-125 mg has been associated with increases in heart rate (of 26-30 bpm) and blood pressure (of diastolic 14.4-25 mmg) (Harris et al., Psychopharmacol., 2002; 162, 396-405, Mas et al., J Pharmacol Exp. Ther., 1999; 290(1):136-45, Mithoefer et al., J Psychopharmacol, 2011; 25(4):439-452) these may be carefully monitored following the regime disclosed elsewhere (Oehen et al., J Psychopharmacol, 2013; 27(1):40-52, Chabrol & Oehen, J Psychopharmacol, 2013; 27(9):865-866), and patients experiencing particular symptoms may not receive a booster dose. The skilled artisan with the teaching of this disclosure in hand will appreciate the factors that may influence the dosage, frequency, and timing required to provide an amount sufficient or effective for providing a therapeutic effect or benefit, and to avoid or minimize adverse effects.

"Therapeutically effective" means causing responses(s) in a mammal after treatment that are judged to be desirable and beneficial. Hence, depending on the mental health disorder to be treated, those responses shall differ, but would be readily understood by those of ordinary skill. Administration of pharmaceutical compositions in an "effective amount," a "therapeutically effective amount," a "therapeutically effective dose," or a "pharmacologically effective amount," refers to an amount of an active agent that is sufficient to provide the desired therapeutic effect, for example, relieving to some extent one or more of the symptoms of the disease or condition being treated. The result can be reduction and/or alleviation of the signs, symptoms, or causes of a disease or disorder, or any other desired alteration of a biological system. The term "therapeutically effective amount" includes, for example, a prophylactically effective amount.

An "effective amount" of the compounds disclosed herein is an amount effective to achieve a desired pharmacologic effect or meaningful therapeutic improvement. It is understood that "an effective amount" or "a therapeutically effective amount" can vary from subject to subject due to variation in metabolism of a compound, such as the compounds described herein, of age, weight, general condition of the subject, the condition being treated, the severity of the condition being treated, and the judgment of the prescribing physician. The effective amount will vary depending upon the subject and the disease condition being treated or health benefit sought, the weight and age of the subject, the severity of the disease condition or degree of health benefit sought, the manner of administration, and the like, all of which can readily be determined by one of skill. Additionally, pharmacogenomic (the effect of genotype on the pharmacokinetic, pharmacodynamic or efficacy profile of a therapeutic) information about a particular patient may affect dosage used.

As used herein, "therapeutic effect" or "therapeutic efficacy" means the responses(s) in a mammal, and preferably a human, after treatment that is judged to be desirable and beneficial. Hence, depending on the disorder to be treated, or improvement in physiological or psychological functioning sought, and depending on the particular constituent(s) in the compositions of the invention under consideration, those responses shall differ, but would be readily understood by those of skill. For example, in some embodiments, "therapeutic effect" may refer to an effect caused by the pharmaceutical composition of the invention, or its use in a method of the invention, such as the treatment of a CNS disorder.

"Therapeutically effective dose" refers to the dose necessary to elicit a desired result within a patient undergoing treatment. A therapeutically effective dose therefore may, in some embodiments, refer to a dose of the pharmaceutical composition or therapeutic combination necessary to deliver measurable patient-specific biologic effects in the treatment or prevention of a condition or disorder. A "therapeutically effective dose" may be used interchangeably with a "therapeutically effective amount" or an "effective amount."

It will be understood that, in some embodiments, the dose actually administered will be determined by a physician, in light of the relevant circumstances, including the disorder to be treated, the chosen route of administration, the actual composition or formulation administered, the age, weight, and response of the individual patient, and the severity of the patient's symptoms, and therefore any dosage ranges disclosed herein are not intended to limit the scope of the invention. In some instances, dosage levels below the lower limit of a disclosed range may be more than adequate, while in other cases doses above a range may be employed without causing any harmful side effects, provided for instance that such larger doses also may be divided into several smaller doses for administration, either taken together or separately. Determination of appropriate dosing shall include not only the determination of single dosage amounts, but also the determination of the number and timing of doses, and the time(s) of day or time(s) preferable for their administration.

In some embodiments, especially where a formulation is prepared in single unit dosage form, suggested dosage amounts shall be known by reference to the format of the preparation itself. In other embodiments, suggested dosage amounts may be known by reference to the means of administration or by reference to the packaging and labeling, package inserts, marketing materials, training materials, or other information and knowledge available to those of skill or the public.

Another aspect of this disclosure provides pharmaceutical kits containing a pharmaceutical composition or formulation of the invention, suggested administration guidelines or prescribing information therefor, and a suitable container. Individual unit dosage forms can be included in multi-dose kits or containers. Pharmaceutical formulations also can be packaged in single or multiple unit dosage forms for uniformity of dosage and ease of administration.

Preferably, the provided MDMA enantiomers and non-racemic mixtures thereof, such as comprising R-MDMA in enantiomeric excess, will be without neurotoxic effect in an animal, and preferably a human, when administered thereto. "Without neurotoxic effect" will be understood to include those compositions and formulations, when administered according to the methods of the invention, and whether acutely or chronically, that are without measurable neurotoxic effect, or without substantial or significant neurotoxic effect, or without neurotoxic effect relative to a composition or formulation of racemic MDMA, or having reduced neurotoxic effect relative to a composition or formulation of racemic MDMA in an amount of at least a 5% reduction, at least a 10% reduction, at least a 15% reduction, at least a 25% reduction, at least a 50% reduction, at least a 75% reduction, at least a 90% reduction, or at least a 95% reduction, or at least a 99% reduction, or without neurotoxic effect or with a reduction of neurotoxic effect when measured using another standard such as one known to those of ordinary skill for the determination or quantification of neurotoxicity and used in the art, and including tests and procedures that are in silico (e.g., by computer analysis or simulation and including by using AI, machine learning, or deep learning models), in vitro (e.g., biochemical assays, tissue culture, etc.), and in vivo (e.g., behavioral assessment; functional observational batteries; tests of motor activity, schedule-controlled operant behavior, neurological function, neurophysiological function, nerve-conduction, evoked-potential; neurochemical, neuroendocrine, or neuropathological measures; EEG; imaging; etc.). See, e.g., Baumann et al., Psychopharmacology. 2007; 189:407-424; Costa & Golembiowska, Experimental Neurology 2022; 347: 113894; Kasteel & Westerink, Expert Opin Drug Metab Toxicol. 2021; 17(8):1007-1017; Pitts et al., Psychopharmacology, 2017; 235(2), 377-392; Rudin et al., Exp Neurol., 2021; 343: 113778; Steinkellner et al., Biol Chem. 2011; 392(0): 103-115; Taghizadeh et al., Free Radic. Biol. Med. 2016; 99: 11-19; White et al., Neurotoxicology, 2011; 32(6): 975-80.

In some embodiments, neurotoxicity or a reduction thereof is determined by measuring the generation of toxic MDMA metabolites, e.g., MDA, such as from evaluating levels in blood, brain, or cerebrospinal fluid (CSF) samples. In some embodiments, neurotoxicity or a reduction thereof is determined by evaluating oxidative stress and dopamine-based quinones. In some embodiments, neurotoxicity or a reduction thereof is determined by evaluating activity and gene expression of antioxidant enzymes and/or pathways. In some embodiments, neurotoxicity or a reduction thereof is determined by measuring reactive oxygen species (ROS) production. In some embodiments, neurotoxicity or a reduction thereof is determined by evaluating mitochondrial dysfunction. Mitochondrial dysfunction may be evaluated by measuring one or more of mitochondrial membrane potential (MMP), mitochondrial swelling, mitochondrial outer-membrane damage, the mitochondrial cytochrome c release, and ADP/ATP ratio. In some embodiments, neurotoxicity or a reduction thereof is determined by assessing the activation of glial cells. For example, reactive astrogliosis can be measured with GFAP staining, and microglia reactivity can be visualized by immunostaining CD11b. In some embodiments, a provided non-racemic mixture effects reduced neurotoxicity relative to MDMA at an equal dose or where the non-racemic mixture is present in a greater dose. In some embodiments, reduced neurotoxicity compared to MDMA is evident even when comparing a dose of a non-racemic mixture comprising R-MDMA in enantiomeric excess of at least 10%, at least 25%, at least 50%, at least 75%, at least 100%, at least 150%, or at least 200% greater than that of MDMA. In embodiments, neurotoxicity or a reduction thereof is determined in vitro. In embodiments, neurotoxicity or a reduction thereof is determined in vivo.

D. Methods of Use

In some aspects, provided herein are methods of using the disclosed compounds, such as MDMA enantiomers and non-racemic mixtures thereof, and compositions comprising the same. In some embodiments, disclosed compounds and compositions thereof are used to modulate neurotransmission. In some embodiments, disclosed compounds and compositions thereof are used to treat a mental health disorder. In some embodiments, disclosed compounds and compositions thereof are used to treat a substance use disorder. In some embodiments, disclosed compounds and compositions thereof are used to reduce social anxiety. In some embodiments, the disclosed non-racemic mixtures of MDMA, e.g., comprising R-MDMA in enantiomeric excess, and compositions thereof are administered to a subject in need thereof to treat a disease or disorder described herein.

In some embodiments, a disclosed compound comprises an enantiomeric mixture wherein R-MDMA is present in an enantiomeric excess of 10%-95%, 20%-95%, 30%-95%, 40%-95%, 50%-95%, 55%-95%, 60%-90%, 65%-90%, or 75%-85%. In some embodiments, a provided enantiomeric mixture comprises R-MDMA in an enantiomeric excess of 10%, 15%, 20%, 25%, 30%, 35%, 40%, 45%, 50%, 55%, 60%, 65%, 70%, 75%, 80%, 85%, 90%, or 95%. In some embodiments, a non-racemic enantiomeric mixture comprises R:S MDMA in a ratio of about 6:1, 7:1, 8:1, 9:1, 10:1, 11:1, or 12:1.

a. Methods of Modulating Neurotransmission

In some embodiments, the disclosed compounds modulate neurotransmission. In some embodiments, modulating neurotransmission comprises regulating levels of monoamines in, for example, the CNS and peripheral tissues. In some embodiments, modulating neurotransmission comprises increasing levels of monoamines in, for example, the CNS and peripheral tissues of a subject to whom a therapeutic compound has been administered. In some embodiments, modulating neurotransmission comprises decreasing levels of monoamines in, for example, the CNS and peripheral tissues of a subject to whom a therapeutic compound has been administered. In some embodiments, modulating neurotransmission by administering a disclosed compound to a subject treats a disease or disorder in the subject.

In some embodiments, a provided non-racemic enantiomeric mixture comprising R-MDMA in enantiomeric excess has reduced affinity for NET relative to racemic MDMA. In some embodiments, a provided non-racemic enantiomeric mixture comprising R-MDMA in enantiomeric excess has reduced potency for releasing norepinephrine relative to racemic MDMA. In some embodiments, a provided non-racemic enantiomeric mixture comprising R-MDMA in enantiomeric excess has reduced affinity for DAT relative to racemic MDMA. In some embodiments, a provided non-racemic enantiomeric mixture comprising R-MDMA in enantiomeric excess has reduced potency for releasing dopamine relative to racemic MDMA. In some embodiments, a provided non-racemic enantiomeric mixture comprising R-MDMA in enantiomeric excess has comparable affinity for SERT relative to racemic MDMA. In some embodiments, a provided non-racemic enantiomeric mixture comprising R-MDMA in enantiomeric excess has comparable affinity for $5\text{-HT}_{2A}$ relative to racemic MDMA.

In some embodiments, modulating neurotransmission comprises modulating activity at the $\alpha 4\beta 2$ receptor nicotinic acetylcholine receptor. In some embodiments, a provided non-racemic enantiomeric mixture comprising R-MDMA in enantiomeric excess has comparable affinity for the $\alpha 4\beta 2$ receptor nicotinic acetylcholine receptor relative to racemic MDMA. In some embodiments, a provided non-racemic enantiomeric mixture comprising R-MDMA in enantiomeric excess has increased affinity for the $\alpha 4\beta 2$ receptor nicotinic acetylcholine receptor relative to R-MDMA. In some embodiments, a provided non-racemic enantiomeric mixture comprising R-MDMA in enantiomeric excess has comparable affinity for the $\alpha 4\beta 2$ receptor nicotinic acetylcholine receptor relative to racemic MDMA and reduced affinity for DAT and NET. In some embodiments, a provided non-racemic enantiomeric mixture comprising R-MDMA in enantiomeric excess has comparable activity at the $\alpha 4\beta 2$ receptor nicotinic acetylcholine receptor, such as agonism, relative to racemic MDMA.

The $\alpha 4\beta 2$ nicotinic acetylcholine receptor is implicated in learning, analgesia, reinforcement, development and aging in the brain (Cordero-Erausquin et al., Trends Pharmacol Sci., 2000 June; 21(6):211-7). In comparison to racemic MDMA an exemplary non-racemic mixture, such as comprising R-MDMA in enantiomeric excess, shows comparable affinity and/or activity at $\alpha 4\beta 2$ nicotinic acetylcholine receptor without further modulating dopaminergic and/or noradrenergic neurotransmission, such as by having relatively reduced affinity for DAT and NET. Methods for determining affinity for and activity at $\alpha 4\beta 2$ nicotinic acetylcholine receptor is available to one of skill in the art, including, e.g., the methods described in Llabres et al., European Journal of Medicinal Chemistry, 2014; 81:35e46. For methods of assessing this and other targets, see also Roth's National Institute of Mental Health Psychoactive Drug Screening Program Assay Protocol Book Version III, 2018.

In some embodiments, an enantiomeric mixture of R-MDMA and S-MDMA comprising R-MDMA in an enantiomeric excess of 10%-95%, 20%-95%, 30%-95%, 40%-95%, 50%-95%, 55%-95%, 60%-90%, 65%-90%, or 75%-85% of R-MDMA is used to modulate neurotransmission. In some embodiments, a non-racemic enantiomeric mixture of R-MDMA and S-MDMA comprises R-MDMA in an enantiomeric excess of 10%, 15%, 20%, 25%, 30%, 35%, 40%, 45%, 50%, 55%, 60%, 65%, 70%, 75%, 80%, 85%, 90%, or 95% is used to modulate neurotransmission. In some embodiments, a non-racemic mixture comprising R:S MDMA in a ratio of about 6:1, 7:1, 8:1, 9:1, 10:1, 11:1, or 12:1 is used to modulate neurotransmission. In some embodiments, a non-racemic mixture comprising R:S MDMA in a ratio of 9:1 has comparable serotonergic activity relative to MDMA, but has reduced affinity for DAT and NET implicated in dopaminergic and noradrenergic neurotransmission.

Detecting a change in monoamine levels in a subject, such as an increase or a decrease, can be achieved according to methods known to one of skill, for example, brain microdialysis (Chefer et al., Curr Protoc Neurosci. 2009; Chapter: Unit 7.1; Darvesh et al., Expert Opin Drug Discov. 2011; 6(2): 109-127) and brain imaging, for example, positron emission tomography (PET) and single photon emission computed tomography (SPECT) (see e.g., Wong & Gjedde, Encyclopedia of Neuroscience, 2009; 939-952 and Takano, Front Psychiatry., 2018; 9:228).

b. Methods of Treatment

In some aspects, provided herein are methods of treating a subject in need thereof by administering a disclosed compound, such as R-MDMA, S-MDMA, or non-racemic mixtures thereof, e.g., comprising R-MDMA in enantiomeric excess. In some embodiments, modulation of neurotransmission by a disclosed compound treats a disease or disorder in a subject. "Treating" or "treatment" of a disorder includes: (i) inhibiting the disorder, i.e., arresting or reducing the development or progression of the disorder or its clinical symptoms; or (ii) relieving the disorder, i.e., causing regression of the disorder or its clinical symptoms. Inhibiting the disorder, for example, would include prophylaxis. Hence, one of skill in the art will understand that a therapeutic amount necessary to effect treatment for purposes of this invention will, for example, be an amount that provides for objective indicia of improvement in patients having clinically-diagnosable symptoms. The effect may be prophylactic in terms of completely or partially preventing a disorder or symptom thereof and/or may be therapeutic in terms of a partial or complete cure for a disorder, an adverse effect attributable to the disorder, and/or a comorbidity simultaneously present with the disorder. A "comorbidity" present may include such other psychiatric disorders (depending on the primary diagnosis) such as antisocial personality disorder, borderline personality disorder, depression, anxiety, pain, such as chronic pain, schizophrenia, ADHD, bipolar disorder, OCD, binge eating disorder, and PTSD.

Moreover, "treatment" as used herein covers any treatment of a disorder in a mammal, and preferably in a human, and includes: (a) preventing a disorder from occurring in a subject who may be predisposed to the disorder but has not yet been diagnosed with it; (b) inhibiting a disorder, i.e., arresting its development; (c) relieving a disorder, i.e., causing regression thereof; (d) protection from or relief of a symptom or pathology caused by or related to a disorder; (e) reduction, decrease, inhibition, amelioration, or prevention of onset, severity, duration, progression, frequency or probability of one or more symptoms or pathologies associated with a disorder; and (f) prevention or inhibition of a worsening or progression of symptoms or pathologies associated with a disorder or comorbid with a disorder. Other such measurements, benefits, and surrogate or clinical endpoints, alone or in combination, would be understood to one of ordinary skill based on the teachings herein and the general knowledge in the art.

The terms "subject," "patient," and "individual" are used interchangeably herein, and refer to any mammal although preferably a human. As used herein, the terms "subject," "patient," and "individual" includes one who has a mental health disorder, a substance use disorder, or a condition related to the same for which similar treatment may be efficacious. When a "subject," "patient," or "individual" is participating in a course of therapy as described below, the term "participant" also may be used. These terms also shall refer to patients in need of treatment for such a disorder, persons predisposed to such a disorder, and subjects whether or not diagnosed with such a disorder. Moreover, these terms shall likewise refer to persons who have received treatment or therapy, are currently receiving therapy or treatment, or who may receive therapy or treatment for a mental health disorder or substance use disorder in the future. In some embodiments, the disclosed methods also can be used to improve mental health and improve psychological functioning in non-disease states, i.e., in an individual without a diagnosed mental disorder, substance use disorder, or specific symptoms thereof. The disclosed methods of treatment also can be modified to treat multiple patients at once, including couples, families, or groups. Hence, these terms will be understood to also mean two or more individuals.

i. Mental Health Disorders

In some embodiments, a provided MDMA enantiomer, such as R-MDMA, S-MDMA, or a non-racemic mixture thereof is used to treat a mental health disorder. In some embodiments, a non-racemic mixture of R-MDMA and S-MDMA, e.g., which comprises R-MDMA in enantiomeric excess, is used to treat a mental health disorder. In some embodiments, an enantiomeric mixture comprising R-MDMA in an enantiomeric excess of 10%-95%, 20%-95%, 30%-95%, 40%-95%, 50%-95%, 55%-95%, 60%-90%, 65%-90%, or 75%-85% is used to treat a mental health disorder. In some embodiments, an enantiomeric mixture comprising R-MDMA in an enantiomeric excess of 10%, 15%, 20%, 25%, 30%, 35%, 40%, 45%, 50%, 55%, 60%, 65%, 70%, 75%, 80%, 85%, 90%, or 95% is used to treat a mental health disorder. In some embodiments, a non-racemic enantiomeric mixture comprising about 6:1, 7:1, 8:1, 9:1, 10:1, 11:1, or 12:1 R:S MDMA is used to treat a mental health disorder. In some embodiments, a composition comprising any of the disclosed MDMA enantiomers or mixtures thereof in a therapeutically effective amount is used to treat a mental health disorder.

"Mental health disorder" or "psychiatric disorder" refers to a disease condition in a mammal, and preferably in a human, that generally involves negative changes in emotion, mood, thinking, and/or behavior. For example, mental health disorders include those characterized by the DSM-5, the Merck Manual, e.g., anxiety and depressive disorders, or other such diagnostic resources known to those of skill. Examples of mental health disorders include anxiety and stressor related disorders, dissociative disorders, eating disorders, mood disorders, e.g., depressive disorders, obsessive-compulsive and related disorders, personality disorders, schizophrenia and related disorders, sexuality, gender dysphoria, and paraphilias, somatic symptom and related disorders, suicidal behavior and self-injury, and substance-related disorders, which includes substance-induced and substance use disorders. (See Merck Manual of Diagnosis and Therapy, 20th Ed., 2018).

The compound(s) of the invention, such as R-MDMA, S-MDMA, or non-racemic mixtures thereof, and compositions comprising the same are useful in methods for treating a variety of mental health disorders. Included among such disorders are depression, major depressive disorder (MDD), treatment-resistant depression (TRD), atypical depression, postpartum depression, catatonic depression, a depressive disorder due to a medical condition, premenstrual dysphoric disorder, seasonal affective disorder, dysthymia, anxiety and phobia disorders, generalized anxiety disorder, agoraphobia, panic disorder, separation anxiety disorder, social anxiety disorder, post-traumatic stress disorder, adjustment disorders, feeding and eating disorders, including binge eating, bulimia, and anorexia nervosa, other binge behaviors, body dysmorphic syndromes, alcoholism, tobacco abuse, drug abuse or dependence disorders, disruptive behavior disorders, impulse control disorders, gaming disorders, gambling disorders, memory loss, dementia of aging, attention deficit hyperactivity disorder, personality disorders, including antisocial, avoidant, borderline, histrionic, narcissistic, obsessive compulsive, paranoid, schizoid and schizotypal personality disorders, attachment disorders, autism, social anxiety in autistic subject, and dissociative disorders.

A variety of methods for screening or assessing a subject for a mental health disorder may be used in accordance with the methods described herein, such as to identify a subject in need of a disclosed compound, such as R-MDMA, S-MDMA, and non-racemic mixtures thereof, such as comprising R-MDMA in enantiomeric excess, and/or to determine a reduction in symptom severity. In some embodiments, a diagnosis of a mental health disorder is facilitated with use of the Diagnostic and Statistical Manual of Mental Disorders, such as the DSM-5. In some embodiments, diagnosis of a mental health disorder is facilitated with use of self-reported or observer-report surveys or questionnaires. Non-limiting examples of such questionnaires include the Clinician-Administered PTSD Scale for DSM-5 (CAPS-5), Montgomery-Asberg Depression Rating Scale (MADRS), Patient Health Questionnaire 9 (PHQ-9), the Generalized Anxiety Disorder 7 (GAD-7), PTSD Checklist for DSM-5 (PCL-5), The Alcohol Use Disorders Identification Test (AUDIT), Binge Eating Scale (BES), Obsessive-Compulsive Inventory (OCI), the Personality Disorders Questionnaire (PDQ-IV), Dissociative Experiences Scale (DES), Drug Use Questionnaire (DAST-20), The Mood Disorder Questionnaire (MDQ), and other similar questionnaires. In some embodiments, alternative questionnaires, such as the Clinical Global Impression-Improvement scale (CGI-I), may be used to assess improvement of a subject's mental health state, such as by comparing baseline responses to responses after a treatment intervention. In some embodiments, any of the diagnostic manuals and assessments described, and other similar tools, may be used to confirm a reduction in symptoms, a reduction in symptom severity, or elimination of symptoms and/or a previous diagnosis.

In some embodiments, the provided MDMA enantiomers and non-racemic mixtures thereof, such as comprising R-MDMA in enantiomeric excess, are used to treat trauma and stressor-related disorders. "Trauma- and stressor-related disorders" include acute stress disorder, adjustment disorders, and post-traumatic stress disorder (Merck Manual, 20th Ed.), as well as reactive attachment disorder, disinhibited social engagement disorder, and others (Am. Psych. Assoc., Diagnostic and Statistical Manual of Mental Disorders (DSM-5) (2013)), including such stressor related disorders as brief psychotic disorder with marked stressor(s), and other disorders associated with psychological trauma. In certain embodiments, the mental health disorder of the invention is specifically PTSD, e.g., moderate to severe PTSD. In some embodiments, a mixture of R-MDMA HCl and S-MDMA HCl in a ratio of 8:1, 9:1, 10:1, 11:1, or 12:1 is used to treat PTSD. In some embodiments, a mixture of R-MDMA HCl and S-MDMA HCl in a ratio of about 8:1, 9:1, or 10:1 is used to treat moderate to severe PTSD in conjunction with psychotherapy. In some embodiments, psychotherapy is conducted in an outpatient setting. In some embodiments, administration of a provided MDMA enantiomer or non-racemic mixture thereof, such as comprising R-MDMA in enantiomeric excess, is preceded by one or more preparatory sessions. In some embodiments, administration of a provided MDMA enantiomer or non-racemic mixture thereof, such as comprising R-MDMA in enantiomeric excess, is followed by one or more integration sessions. In some examples, integration sessions focus on translating gained insights into meaningful and lasting change. See, e.g., Pilecki et al., Harm Reduct J. 2021; 18: 40; Bogenschutz & Forcehimes, J Humanist Psychol. 2017; 57:389-414. The severity of PTSD can be determined according to assessments available to one of skill in the art, e.g., the Clinician-Administered PTSD Scale for DSM-5 (CAPS-5). Additional implications and symptoms of PTSD, and comorbidities associated with the same, which may benefit from the provided therapeutic compounds, are described in, e.g., Davis et al., J Clin Psychiatry, 2022; 83(3):21m14116; Steenkamp et al., JAMA, 2020; 323(7): 656-657.

While the neurophysiology underlying mental health disorders may be distinct, an aspect in common of many is the presence of a deleterious, repetitive, and often "rigid" thought process that negatively impacts an individual's ability to function. For someone with PTSD, for instance, symptoms involve re-experiencing trauma and the feelings associated with it; for depression it can take the form of a recurrent internal editor that attaches negative connotations to normal life events; and for addiction it is the preoccupation with acquiring and using the substance of choice. Thus, in many embodiments, the method of treating a mental health disorder involves the treatment of a disorder related to rigid modes of thinking. In different embodiments, the disorder related to rigid modes of thinking can be anxiety, depression, addiction, an eating disorder, obsessive compulsive disorder, or PTSD.

In some embodiments, the pharmaceutical compositions and formulations of the invention are used to manage emotional regulation, for example in a patient with a stress disorder, acute stress disorder, brief psychotic disorder with marked stressor(s), delirium, mild cognitive impairment (MCI), dementia, psychosis, and psychotic major depression, as those terms are generally understood, for example by reference to the DSM-5. "Psychological distress" related to life-threatening illness or death includes depression, anxiety, and existential distress, e.g., end-of-life anxiety. See, e.g., Wolfson et al., Sci Rep. 2020; 10 20442. In some embodiments, the pharmaceutical compositions and formulations of the invention are used with patients in long-term, hospice, or institutional care.

In some embodiments, the pharmaceutical compositions and formulations of the invention are used to reduce the symptoms of a mental health disorder. The symptoms of the mental health disorder to be treated shall be able to be determined by one of skill in the art, by reference to the general understanding of the art regarding that disorder, e.g., criteria according to the Diagnostic and Statistical Manual of Mental Disorders, such as the DSM-5, and/or International Classification of Diseases, such as the ICD-10.

Symptoms of PTSD, for example, include transient waking dissociative states in which events are relived as if happening ("flashbacks"), nightmares, distressing and intense memories, other intrusive negative memories, distress or physical reactions after being exposed to triggers, blaming self or others for the trauma, decreased interest in things that were once enjoyable and other feelings of emotional numbness, negative feelings about self and the world, inability to remember the trauma clearly, difficulty feeling positive, feelings of isolation, negative affect, difficulty feeling positive, other negative alterations in cognition and mood, avoidance, aggression or irritability, hypervigilance and hyper-awareness, difficulty concentrating, difficulty sleeping, heightened startle response, engaging in self-destructive, or risky behavior, difficulty sleeping or staying asleep, and suicidal ideation. Accordingly, methods of the invention that reduce the symptoms of PTSD would be understood to reduce any such symptoms. In some embodiments, disclosed compounds reduce the severity of PTSD, as determined by diagnostic criteria available to one of skill in the art, such as, in non-limiting examples, the Clinician Administered PTSD Scale (CAPS-IV and CAPS-V) and the PTSD Symptom Scale-Interview for DSM-5 (PSS-I-5).

In some embodiments, the disclosed MDMA enantiomers or enantiomerically enriched mixtures thereof are used to alleviate social anxiety or enhance social cognition. In some embodiments, such effects lead to a reduction in social awkwardness. Social awkwardness can be assessed with use of tools available to one of skill in the art, including, e.g., the Liebowitz Social Anxiety Scale (LSAS), the Social Anxiety Questionnaire for Adults (SAQ-A30), the Social Anxiety Scale for Adolescents (SAS-A), and the Social Interaction Anxiety Scale (SIAS). See, e.g., Ranta et al., Child Psychiatry Hum Dev., 2012; 43(4):574-91.

In some embodiments, the disclosed MDMA enantiomers or enantiomerically enriched mixtures thereof are used to treat social anxiety in autistic adults. Adults with moderate to extremely severe social anxiety who receive the disclosed MDMA enantiomers or enantiomerically enriched mixtures thereof will experience a significant improvement in Liebowitz Social Anxiety Scale (LSAS) scores from baseline to primary endpoint. Following the completion of treatment, the reduction in social anxiety will either remain consistent or continue to improve, as has previously been demonstrated (Danforth et al., Psychopharmacol (Berl)., 2018; 235(11): 3137-3148). A systematic review of MDMA as a medicament in autistic social impairment found it to be efficacious as a pharmacological treatment (Chaliha et al., Curr Neuropharmacol., 2021; 19(7):1101-1154), and the disclosed MDMA enantiomers or enantiomerically enriched mixtures thereof are expected to have equal or greater efficacy as compared to MDMA for social anxiety, and in some embodiments, fewer adverse events. In some embodiments, the disclosed MDMA enantiomers or enantiomerically enriched mixtures thereof are useful to reduce the signs and symptoms of ADHD, such as hyperactivity, restlessness, and impulsiveness.

ii. Substance Use Disorders

In some aspects, provided herein are methods of using the disclosed compounds, such as R-MDMA and S-MDMA, non-racemic enantiomeric mixtures thereof, and compositions thereof to treat substance use disorders. In some embodiments, disclosed compounds, or compositions comprising the same, are administered to a subject having a substance use disorder to treat or reduce the severity of said substance use disorder. In some embodiments, a provided enantiomeric mixture, wherein R-MDMA is present in an enantiomeric excess of 10%-95%, 20%-95%, 30%-95%, 40%-95%, 50%-95%, 55%-95%, 60%-90%, 65%-90%, or 75%-85% of R-MDMA is used to treat a substance use disorder. In some embodiments, an enantiomeric mixture, wherein R-MDMA is present in an enantiomeric excess of 10%, 15%, 20%, 25%, 30%, 35%, 40%, 45%, 50%, 55%, 60%, 65%, 70%, 75%, 80%, 85%, 90%, or 95% is used to treat a substance use disorder. In some embodiments, about 6:1, 7:1, 8:1, 9:1, 10:1, 11:1, or 12:1 R:S MDMA is administered to a subject in need thereof to treat a substance use disorder.

Broadly, but without being bound by theory, substance use disorders are mediated by the dopamine system (Diana, Front Psychiatry, 2011; 2:64). Additionally, the noradrenergic system has been found to contribute to addiction, including reward and drug seeking behavior (Foster & Weinshenker, Neural Mechanisms of Addiction, 2019; 221-236). In some embodiments, therapeutic compounds or pharmaceutical compositions thereof are used to treat substance use disorders. In some examples, substance use disorders are characterized by excessive use of nicotine, alcohol, and narcotics including prescription drugs and drugs of abuse. Such use may lead to one or more of social, academic, and occupational impairment. Commonly abused substances include, e.g., alcohol, tobacco (nicotine), cannabis, sedatives, hypnotics, anxiolytics, inhalants, opiates, opioids, and stimulants (Jahan & Burgess, "Substance Use Disorder," Treasure Island (FL): StatPearls Publishing; 2022).

1. Alcohol Use Disorder

In some embodiments, the provided enantiomeric mixtures of MDMA, wherein R-MDMA is in enantiomeric excess, are used to treat or reduce the severity of alcohol use disorder (AUD). AUD refers to the disorder as defined in the Diagnostic and Statistical Manual of Mental Disorders, for example, the DSM-5. The severity of AUD, mild, moderate, or severe, is based on the number of criteria met. In some embodiments, the provided enantiomeric mixtures of MDMA, wherein R is in enantiomeric excess, is used to treat alcohol abuse, alcohol dependence, or alcohol use in a subject who has not yet had a formal clinical diagnosis. See, e.g., "Alcohol Dependence Syndrome," see Edwards, Brit. J. Addiction, 81:171-183.

In some embodiments, administration of the provided enantiomeric mixtures of MDMA, wherein R-MDMA is in enantiomeric excess, results in a reduction of subject's alcohol use. Reducing alcohol use, or reduction of alcohol use, refers to reducing the amount or frequency of alcohol use, for example as assessed by urinalysis e.g., by measuring metabolites of alcohol in urine, such as Ethyl Glucuronide (EtG) or as assessed by using self reported alcohol use with standardized tools like the Timeline Follow Back self report. See, e.g., Robinson et al., Psychol Addict Behav., 2014; 28(1):154-62; Sobell et al., Drug Alcohol Depend., 1996; 42(1):49-5.

2. Opioid Use Disorder

In some embodiments, the provided enantiomeric mixtures of MDMA, wherein R-MDMA is in enantiomeric excess, are used to treat opioid use disorder, which will include opiate use disorder. Receptors of the opioid system, mu, kappa, delta, and opioid receptor like-1 (ORL1) are G-protein coupled receptors that activate inhibitory G-proteins (Al-Hasani & Bruchas, Anesthesiology, 2011; 115(6): 1363-1381). Opioids activate the mesolimbic reward system, which promotes signaling in the ventral tegmental area and results in dopamine release (Kosted & George, Sci Pract Perspect., 2002; 1(1):13-20). Representative examples of opioids include codeine, heroin, hydrocodone, hydromorphone, methadone, meperidine, morphine, and oxycodone. It will be appreciated that "opiates" may be included among "opioids" for purposes of the inventions herein.

Opioid use disorder (OUD) is characterized by an overwhelming desire to use opioids, the development of tolerance to opioids, and withdrawal syndrome once opioids are discontinued. Criteria for opioid use disorder are available to one of skill. In one example, the DSM-5 describes criteria, for example: Opioids are often taken in larger amounts or over a longer period of time than intended; Tolerance, as defined by either of the following: (a) a need for markedly increased amounts of opioids to achieve intoxication or desired effect or (b) markedly diminished effect with continued use of the same amount of an opioid; Withdrawal, as manifested by either of the following: (a) the characteristic opioid withdrawal syndrome or (b) the same (or a closely related) substance is taken to relieve or avoid withdrawal symptoms. In some embodiments, therapeutic compounds alleviate or reduce the signs or symptoms of opioid use disorder. In some embodiments, a therapeutic compound may be used as an adjunct to clinical opioid therapy.

Treatments for OUD include opioid receptor agonists, for example, methadone and buprenorphine, and opioid receptor antagonists, for example, naltrexone (Kampman et al., J. Addict. Med., 2015; 9(5):358-367). However, such treatments are associated with limited success in preventing relapse and, in some cases, carry abuse liability themselves. The dopamine system has been implicated in opioid reward (Fields & Margolis, Trends Neurosci., 2015; 38(4):217-225; Steidl et al., Neurosci. Biobehav. Rev., 2017; 83:72-82). D3 antagonists may be useful to treat opioid addiction and to potentiate the effects of prescribed opiates (Galaj et al., Neurosci. Biobehav. Rev., 2020; 114: 38-52). The effects of the provided enantiomeric mixtures on opioid-seeking behavior may be evaluated according to methods available to one of skill, including self-administration models, e.g., the IV self-administration reinstatement rodent model described by Fattore et al., Methods Mol Biol. 2021; 2201: 231-245.

3. Nicotine Dependence and Tobacco Use Disorder

In some embodiments, the provided enantiomeric mixtures of MDMA, wherein R-MDMA is in enantiomeric excess, are used to treat nicotine dependence. In some embodiments, administration of the provided enantiomeric mixtures of MDMA, wherein R-MDMA is in enantiomeric excess, is used to treat tobacco use disorder. Nicotine addiction is mediated by activation of neuronal nicotinic acetylcholine receptors in the dopamine pathway, and nicotine exposure results in release of dopamine and an increase in extracellular dopamine levels (Laviolette & van der Kooy, Nat. Rev. Neurosci., 2004; 5(1):55-65; Nisell et al., Synapse, 1994; 16(1):36-44; Pierce & Kumaseran, Neurosci. Biobehav. Rev., 2006; 30(2):215-38). Tobacco is a common vehicle for nicotine and so nicotine dependence may be referred to as tobacco use disorder.

Criteria for nicotine dependence or tobacco use disorder are available to one of skill. See, e.g., Baker et al., Addiction, 2012; 107(2):263-275. In one example, the DSM-5 describes tobacco use disorder and criteria for the same, for example: Unsuccessful efforts to quit or reduce intake of tobacco; Inordinate amount of time acquiring or using tobacco products; Cravings for tobacco. In embodiments, therapeutic compounds alleviate or reduce the signs or symptoms of nicotine dependence or tobacco use disorder. A compound's effects on nicotine seeking behavior may be evaluated according to methods available to one of skill, including self-administration, place conditioning, and intracranial self-stimulation paradigms in rodents (O'Dell & Khroyan, Pharmacol Biochem Behavior, 2009; 91(4): 481-488).

4. Sedative, Hypnotic, and Anxiolytic Use Disorder

In some embodiments, the provided enantiomeric mixtures of MDMA, wherein R-MDMA is in enantiomeric excess, are used to treat sedative, hypnotic, and anxiolytic use disorder. Sedatives, hypnotics, and anxiolytics can cause CNS depression, which may be fatal. Exemplary CNS depressants include benzodiazepines, such as alprazolam, clonazepam, lorazepam, diazepam, chlordiazepoxide, and barbiturates, such as phenobarbital, pentobarbital, butabarbital. Other classes of drugs have properties that share a similar mechanism of action with benzodiazepine and barbiturates, including alcohol. These agents mediate gamma-aminobutyric acid (GABA) effects, producing inhibitory effects within the central nervous system.

Criteria for sedative, hypnotic, and anxiolytic use disorder are available to one of skill. In one example, the DSM-5 describes sedative, hypnotic, and anxiolytic use disorder and criteria for the same, for example: Sedatives, hypnotics, or anxiolytics are often taken in larger amounts or over a longer period than was intended; There is a persistent desire or unsuccessful efforts to cut down or control sedative, hypnotic, or anxiolytic use; A great deal of time is spent in activities necessary to obtain the sedative, hypnotic, or anxiolytic; use the sedative, hypnotic, or anxiolytic; or recover from its effects. In some embodiments, therapeutic compounds alleviate or reduce the signs or symptoms of sedative, hypnotic, and anxiolytic use disorder.

5. Stimulant Use Disorder

In some embodiments, the provided enantiomeric mixtures of MDMA, wherein R-MDMA is in enantiomeric excess, are used to treat stimulant use disorder. Stimulants increase synaptic levels of the monoamines dopamine, serotonin, and norepinephrine. Both the dopaminergic and the noradrenergic systems play critical roles in the effects of stimulants, including reward (Sofuoglu & Sewell, Addict Biol., 2009; 14(2): 119-129; Wise, Brain Res., 1978; 152 (2):215-47). Non-limiting examples of stimulants include amphetamines, methamphetamine, and cocaine. Nicotine/tobacco may also be considered a stimulant. In some embodiments, the provided enantiomeric mixtures of MDMA, wherein R-MDMA is in enantiomeric excess, are used to treat cocaine use disorder. In some embodiments, the provided enantiomeric mixtures of MDMA, wherein R-MDMA is in enantiomeric excess, are used to treat methamphetamine use disorder.

Criteria for stimulant use disorder are available to one of skill. For example, exemplary DSM-5 criteria include: The stimulant is often taken in larger amounts or over a longer period than was intended; There is a persistent desire or unsuccessful efforts to cut down or control stimulant use; A great deal of time is spent in activities necessary to obtain the stimulant, use the stimulant, or recover from its effects. In some embodiments, therapeutic compounds alleviate or reduce the signs or symptoms of stimulant use disorder.

Treatment options for stimulant use disorder include contingency management, CBT, acupuncture, antidepressants, dopamine agonists, antipsychotics, anticonvulsants, disulfiram, opioid agonists, N-Acetylcysteine, and psychostimulants (Ronsley et al., PLoS One, 2020; 15 (6): e0234809). Psychostimulants, for example, bupropion and dexamphetamine, appear to be promising treatment options. In contrast, dopamine modulators, including agonists and antagonists appear to lack efficacy in stimulant use disorders, such as cocaine use disorder (Cochrane Database Syst Rev. 2015 May; 2015(5): CD003352; Id. Rev. 2016 March; 2016(3): CD006306). The effects of a compound on stimulant addiction may be assessed using methods available to one of skill, including self-administration models, e.g., the hold down procedures described by Zimmer & Roberts, Psychiatric Disorders, 2011; 279-290.

In general, all of the compositions, formulations and methods of the invention will be appreciated to work for all individuals, although individual variation is to be expected, and will be understood. Where there is variation between individuals, modification to the compositions and methods will be understood based on the teachings herein in combination with the general knowledge of the art. In some instances, certain personalized approaches (i.e., "personalized" or "precision" medicine) may be utilized, based on individual characteristics, including drug metabolism (e.g., CYP1A2, CYP2D6, CYP2C19, and CYP3A4) or individual genetic variation.

"Genetic variation" refers to a change in a gene sequence relative to a reference sequence (e.g., a commonly-found and/or wild-type sequence). Genetic variation may be recombination events or mutations such as substitution/deletion/insertion events like point and splice site mutations. In an embodiment, the genetic variation is a genetic variation in metabotropic glutamate receptor type 5 (mGluR5), which has been implicated in mood and anxiety symptoms in humans. In an embodiment, the genetic variation is one or more single nucleotide polymorphisms (SNPs) in the FKBP5 gene that are associated with elevated levels of FKBP5 1 protein relative to persons lacking such SNPs. The FKBP5 gene has been implicated in responses to stress and trauma, and such SNPs are correlated with susceptibility to certain depression, PTSD, and anxiety disorders (Yehuda & Hoge, JAMA Psychiatry, 2016; 73(5):433-434, Bierer et al., Am J Psych, 2020; 177(8): 744-753).

c. Methods of Administration

In some embodiments, the compounds described herein, such as MDMA enantiomers and non-racemic mixtures thereof, are useful in treating a patient diagnosed with at least one mental health condition. In some embodiments, a patient diagnosed with at least one mental health condition is prescribed a therapeutically effective amount of the compounds described herein. In some embodiments, the disclosed compounds are prescribed to a patient diagnosed with at least one mental health condition in a pharmaceutical composition comprising an effective amount of the compounds described herein, as well as a pharmaceutically acceptable carrier, diluent, or excipient.

In some embodiments, a patient diagnosed with at least one mental health condition obtains the compounds described herein without a prescription. In some embodiments, a patient diagnosed with at least one mental health condition is administered an effective amount of the compounds described herein by a clinician. In some embodiments, a patient diagnosed with at least one mental health condition self-administers the compounds described herein. In some embodiments, a patient diagnosed with at least one mental health condition is supervised by a health professional while self-administering the compounds described herein while, in other embodiments, the patient is not supervised by a health professional while self-administering the compounds described herein. In some embodiments, a patient diagnosed with at least one mental health condition is administered, either by the patient or a third-party, an effective amount of the compounds described herein as part of a psychotherapy regimen. In some embodiments, a patient diagnosed with at least one mental health condition is administered, either by the patient or a third-party, an effective amount of the compounds described herein not part of a psychotherapy regimen.

In some embodiments, the compounds described herein are efficacious in reducing at least one symptom of a mental health condition within a patient diagnosed with the same. As would be apparent to one of skill, symptoms for each mental health condition will be different, however, through medical monitoring (such as monitoring of objective measurements, as described herein), patient reporting (such as, but not limited to through journaling), completion of questionnaires, etc., one will be able to objectively determine if a symptom has reduced in its frequency and/or magnitude.

In some embodiments, R-MDMA, S-MDMA, or an enantiomeric mixture thereof is administered in conjunction with psychotherapy. In some embodiments, an enantiomeric mixture of R-MDMA and S-MDMA comprises R-MDMA in an enantiomeric excess of 10%-95%, 20%-95%, 30%-95%, 40%-95%, 50%-95%, 55%-95%, 60%-90%, 65%-90%, or 75%-85% of R-MDMA is administered in conjunction with psychotherapy. In some embodiments, a provided enantiomeric mixture of R-MDMA and S-MDMA comprises R-MDMA in an enantiomeric excess of 10%, 15%, 20%, 25%, 30%, 35%, 40%, 45%, 50%, 55%, 60%, 65%, 70%, 75%, 80%, 85%, 90%, or 95% is administered in conjunction with psychotherapy. In some embodiments, about 6:1, 7:1, 8:1, 9:1, 10:1, 11:1, or 12:1 R:S MDMA is administered in conjunction with psychotherapy.

Psychotherapy conducted with a compound of the invention is typically conducted in widely spaced sessions, typically with two administrations of an entactogen per session (a first dose, and a "booster" dose). These sessions can be as frequent as weekly but are more often approximately monthly or less frequent. In most cases, a small number of sessions, on the order of one to three, is needed for the patient to experience significant clinical progress, as indicated, for example, by a reduction in the symptoms of the mental health disorder being treated. In some embodiments, psychotherapy comprises multiple sessions, during some of which a compound of the invention is administered ("MDMA-assisted psychotherapy") and in others, the patient participates in another psychosocial or behavioral therapy.

The term "psychosocial or behavioral therapy" refers to, but is not limited to, such therapies other than the MDMA-assisted psychotherapy of the invention, e.g., 12-step facilitation therapy (e.g., NIAAA, Project MATCH Monograph Series. Volume 1, NIH Publication No. 94-3722, (1995)

reprinted 1999), cognitive behavioral therapy (e.g., as described in Arch. Gen. Psychiatry 1999; 56:493-502), interpersonal therapy (e.g., as described in Psychol Addict Behav, 2009; 23(1): 168-174), contingency management based therapy (e.g., as described in Psychol Addict Behav 2009; 23(1): 168-174; in J. Consul. Clin. Psychol. 2005; 73(2): 354-59; or in Case Reports in Psychiatry, Vol. 2012, Article ID 731638), community reinforcement approach based therapy (e.g., as described in Drug Alcohol Depend 2004; 74:1-13), motivational interviewing based therapy (e.g., as described in J. Consul. Clin. Psychol. 2001; 69(5): 858-62), motivational enhancement based therapy (e.g., as described in Drug Alcohol Depend 2007, 91:97-101) or meditation based therapy, such as transcendental meditation based therapy (e.g., as described in Addiction 2004; 99(7): 862-874 or J. Consul. Clin. Psychol. 2000; 68(3): 515-52).

The term "standardized psychological treatment" or "standardized psychological support" refers to standard counseling sessions where the patient meets with a therapist, for example once a week, in particular counseling focused on reducing the severity or the symptoms of the medical health disorder to be treated.

As used herein, "therapist" refers to a person who treats a patient using the compositions and methods of the invention, whether that person is a psychiatrist, clinical psychologist, clinical therapist, registered therapist, psychotherapist, or other trained counselor, facilitator, or guide. Generally, a therapist will be certified in the use of the treatment manual for the MDMA-assisted psychotherapy administered, and will have completed the appropriate training in delivering that form of MDMA-assisted psychotherapy. This will enable a therapist to respond in a safe and supportive manner during the non-drug and drug administration sessions. Recent studies with drug-assisted psychotherapy have shown that most psychiatric emergencies, e.g., acute anxiety associated with the emergence of challenging emotional material during the therapeutic session, can be dealt with through "talking down" the anxious patient, with no necessary requirement for psychiatric medication. However, within the definition of "therapist" include psychiatrists licensed to manage psychiatric emergencies by administering "rescue medications" such as short-acting benzodiazepines (e.g., oral lorazepam) if clinically indicated.

d. Coadministration of MDMA and Other Oxytocin-Releasing Agents

One of the theories behind the potential efficacy of MDMA for therapeutic use is its ability to increase or promote the release of oxytocin in the brain. Oxytocin (OT) has been implicated as a potential factor in numerous psychiatric disorders. Accordingly, in some embodiments are contemplated the administration of MDMA (where "MDMA" includes any MDMA-comprising composition of the invention, e.g., an enantiomerically-enriched mixture of MDMA stereoisomers or a substantially pure or pure composition of a single enantiomer such as R-MDMA) together with an additional active compound, such agent being selected from drugs that stimulate the release of OT.

Compositions including an additional oxytocin-releasing agent will further enhance trust, social information processing, empathy, and general social cognitive function during behavioral therapy or counseling sessions, e.g. during sessions of MDMA-assisted psychotherapy, thereby increasing the efficacy of such sessions, or otherwise will increase therapeutic efficacy or aspects thereof when administered in the methods of the present invention, including without therapy.

Accordingly, in certain embodiments, the disclosure contemplates the use of oxytocin releasing agents in combination with the disclosed compounds, such as R-MDMA, S-MDMA, and non-racemic mixtures thereof, and pharmaceutical compositions comprising the same. In specific embodiments, the disclosure relates to methods for treating a psychological disorder including administering a compound that stimulates OT release (herein, an "oxytocin-releasing agent," an "oxytocin-releasing compound," or an "ORA") to a subject in conjunction with MDMA-assisted therapy. The release of OT will enhance the efficacy of the MDMA-assisted therapy by, for example, enhancing social cognitive functioning of the patient.

In certain embodiments, the oxytocin-releasing compound is administered within a psychotherapeutic window. The psychotherapeutic window can be within one month of a psychotherapy session, or within one week of a psychotherapy session, or within one day of a psychotherapy session. The compound can be administered during the therapy session, and in certain embodiments, is administered before the session begins. The oxytocin-releasing drug may be administered by a clinician. Alternatively, the drug may be self-administered by the patient. The oxytocin-releasing drug is preferably administered within five hours of a psychotherapy session. In one embodiment the drug is administered within five minutes of a psychotherapy session. However, in an alternative embodiment the drug is administered up to one hour prior to a psychotherapy session.

In embodiments, the ORA and the MDMA, such as R-MDMA, S-MDMA, or a non-racemic mixture thereof, are administered together, as a single composition, or prepared as a single pharmaceutical formulation. In other embodiments, the ORA and the MDMA will be administered together or closely together in time (e.g., within 1 minute, within 5 minutes, within 15 minutes, within an hour, during the same drug-assisted therapy session, or on the same day), but will be administered as separate pharmaceutical compositions, formulations, or drug products. Separate compositions, for example, will allow an MDMA composition to be tailored to multiple different ORAs, depending on patient profile and therapeutic goals, and will allow for dosing to be adjusted for each compound individually.

In some embodiments, an enantiomeric mixture of R-MDMA and S-MDMA comprises R-MDMA in an enantiomeric excess of 10%-95%, 20%-95%, 30%-95%, 40%-95%, 50%-95%, 55%-95%, 60%-90%, 65%-90%, or 75%-85% of R-MDMA is coadministered with an oxytocin-releasing agent. In some embodiments, an enantiomeric mixture of R-MDMA and S-MDMA comprises R-MDMA in an enantiomeric excess of 10%, 15%, 20%, 25%, 30%, 35%, 40%, 45%, 50%, 55%, 60%, 65%, 70%, 75%, 80%, 85%, 90%, or 95% is coadministered with an oxytocin-releasing agent. In some embodiments, 6:1, 7:1, 8:1, 9:1, 10:1, 11:1, or 12:1 R:S MDMA is coadministered with an oxytocin-releasing agent.

In certain embodiments, the ORA administered promotes the onset of positive emotional mood without measurable systemic effects on the oxytocin system. In other embodiments, the ORA causes measurable systemic effects on the oxytocin system, as could be quantified by one of ordinary skill in the art, through the practice of ordinary skill.

Preferably, the ORA does not cause increases in heart rate, blood pressure, motor activity, or significant increases thereto.

In some embodiments, the ORA is a melanocortin (MC) receptor agonist, a melanocyte stimulating hormone, a-melanocortin, a-melanotropin, melanotan II (MT-11), bremelanotide, or an analog or derivative thereof. Other non-limiting examples of ORAs include serotonin receptor agonists such as 5-HT1A, 5-HT2A, or 5-HT2C agonists, and including 6-(2-Aminopropyl)-2,3-dihydrobenzofuran (6-APDB), 6-(2-aminopropyl)benzofuran (6-APB), (4-fluoro-N-(2-{4-[(2S)-2-(hydroxymethyl)-2,3-dihydro-1,4-benzodioxin-5-yl]piperazin-1-yl}ethyl)benzamide (flesinoxan), 5-(3-[((2S)-1,4-benzodioxan-2-ylmethyl)amino]propoxy)-1,3-benzo-dioxole, (osemozotan), buspirone, gepirone, befiradol, eptapirone, 8-OH-DPAT, tandospirone, serotonin, ergine, ergotamine, lysergic acid, lysergic acid diethylamide (LSD), psilocybin, 4-hydroxy-dimethyltryptamine, N,N-dimethyltryptamine (DMT), 5-methoxy-dimethyltryptamine (5-MeO-DMT), mescaline, an entactogen, 4-bromo-2,5-dimethoxyphenethylamine, 3,4-methylenedioxyamphetamine (MDA), methylenedioxyethylamphetamine (MDEA), 3-methoxy-4,5-methylenedioxy-amphetamine (MMDA), racemic 3,4-methylenedioxymethamphetamine, tenamfetamine, lorcaserin, and analogs, derivatives, prodrugs, and salts thereof.

The ORA will be administered in a therapeutically effective amount, which is that amount that provides improved therapeutic benefit relative to that achieved by an MDMA-comprising composition taken alone. For example, a therapeutically effective amount can be an amount sufficient to reduce the number of therapy visits needed to treat a particular condition, to alleviate the symptoms of a psychiatric condition or mental health disorder, or to cause an improvement or enhancement of one or more of a patient's self-reported outcome measures, such as satisfaction, happiness, self-worth, self-approval, positive interactions with others, or the like.

Dosage levels from about 0.001 mg/kg to about 140 mg/kg of body weight per day are useful for the purpose of the invention or about 0.05 mg to about 7 g per patient per day. Alternatively, dosage levels from about 0.01 mg to 50 mg of the compound per kilogram of body weight per day, or alternatively about 0.5 mg to about 2.5 g per patient per day. It will be appreciated, however, that the specific dose level for any particular patient will depend upon a variety of factors (as with the dose of MDMA administered) including the age, body weight, general health, sex, diet, time of administration, route of administration, rate of excretion, drug combination and the severity of the particular disease undergoing therapy.

The ORA is typically formulated with a pharmaceutically acceptable diluent, excipient, or carrier, as would be understood by practice of ordinary skill, and by reference to any of the formulation examples or disclosure above for MDMA, enantiomers thereof, and enantiomeric mixtures thereof, such as mixtures having R-MDMA in enantiomeric excess.

e. Coadministration of MDMA and Supplements

In some embodiments, a provided MDMA enantiomer or non-racemic mixture thereof, such as comprising R-MDMA in enantiomeric excess, and one or more supplements are coadministered to a subject. As will be understood in the context of coadministration, the supplement may be administered at any one or more of prior to, along with, or following administration of a a provided MDMA enantiomer or non-racemic mixture thereof, such as comprising R-MDMA in enantiomeric excess. In some embodiments, the coadministration regimen exerts neuroprotective effects. In some embodiments, the coadministration regimen prevents or reduces neurotoxicity.

In some embodiments, the supplement is selected from the group consisting of alpha lipoic acid (ALA), magnesium, vitamin C, ascorbate, grape seed extract, grapefruit juice, acetyl-L-carnitine (ALCAR), green tea extract, 5-HTP, melatonin, and CoQ10. In some embodiments, an enantiomeric mixture of R-MDMA and S-MDMA comprising R-MDMA in an enantiomeric excess of 10%-95%, 20%-95%, 30%-95%, 40%-95%, 50%-95%, 55%-95%, 60%-90%, 65%-90%, or 75%-85% is coadministered with a supplement. In some embodiments, an enantiomeric mixture of R-MDMA and S-MDMA comprising R-MDMA in an enantiomeric excess of 10%, 15%, 20%, 25%, 30%, 35%, 40%, 45%, 50%, 55% 60%, 65%, 70%, 75%, 80%, 85%, 90%, or 95% is coadministered with a supplement. In some embodiments, a non-racemic enantiomeric mixture of R:S MDMA in a ratio of about 6:1, 7:1, 8:1, 9:1, 10:1, 11:1, or 12:1 is coadministered with a supplement.

E. Definitions

The terminology used herein is for describing embodiments and is not intended to be limiting. As such, the definitions below will be appreciated to provide examples of definitions that may be considered to assist in understanding and practicing the invention, but the full scope of any term (and especially the ultimate definition of any term used in the claims) will be found only in light of the entirety of the application and in view of any plain meaning known in the art. When introducing elements of the present invention or the preferred embodiments thereof, the articles "a," "an," "the," and "said" are intended to mean that there are one or more of the elements. The terms "comprising," "including," and "having" are intended to be inclusive and not exclusive (i.e., there may be other elements in addition to the recited elements). Thus, the terms "including," "may include," and "include," each mean and are used interchangeably with the phrase "including but not limited to." The term "or" is used herein to mean, and is used interchangeably with, the term "and/or," unless context clearly indicates otherwise.

Unless otherwise stated, all measurements, values, ratings, positions, magnitudes, sizes, locations, orientations, configurations, and other specifications that are set forth (either expressly or impliedly) in this specification, including in the figures and in the claims that follow, are approximate, and not exact. They are intended to have a reasonable range that is consistent with the functions to which they relate and with what is customary in the art to which they pertain. Where a range of values is provided, it will be understood that the upper and lower limit, and each intervening value between the upper and lower limit of the range, is encompassed within the embodiments. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms herein have the meaning as commonly understood by one of ordinary skill in the art to which this invention belongs. In the event there is a plurality of definitions for a term herein, those in this section prevail unless stated otherwise. Further definitions that may assist the reader to understand the disclosed embodiments are as follows, and such definitions may be used to interpret the defined terms, when those terms are used herein. However, the examples given in the definitions are generally non-exhaustive and must not be construed as limiting the invention. It also will be understood that a substituent should comply with chemical bonding rules and steric compatibility constraints in relation to the particular molecule to which it is attached.

F. Examples

Example 9: Selection of an Enantiomeric Mixture of 3,4-MDMA

Purpose: To provide an enantiomeric mixture of 3,4-MDMA having a comparable level of serotonergic activation to racemic MDMA, while significantly decreasing activation of the dopaminergic and norepinephrine systems. Activation of dopaminergic and norepinephrine systems by racemic MDMA have been implicated in neurotoxicity and reinforcement behavior, which may potentiate the potential for abuse.

Methods: Selection of the provided ratio of R-MDMA and S-MDMA salts, 9:1, was performed using a proprietary computational system for the modeling of psychoactive drug pharmacology. A multi-parameter computational network was trained on a labeled corpus of pharmacological data of small molecule candidates. Model parameters such as drug potency, affinity, bioavailability, and pharmacokinetic profile were used to generate candidates which were then screened against a labeled dataset and curated for highest probability hits.

Yamanishi and ToxCast benchmark datasets were used for ligand-binding prediction along with a smaller dataset of psychoactive serotonergic small molecules. A recurrent neural network model similar to DeepAffinity (Karimi et al., Bioinformatics, 2019; 35(18):3329-3338) was used, with SMILES for drug structure representation. Outputs included drug-target binding affinities, which were generated for each candidate. For predicted drug effects, a hand-assembled database was used, with labeled data from MAPS, Erowid, and other sources.

The optimal ratio was determined by evaluating the model on the dual enantiomers of MDMA based on the pre-assigned scoring criteria, namely potency, selective agonism at serotonin, dopamine, and norepinephrine terminals, the $5HT_{2A}$ receptor, oxytocin secretion via $5HT_A$, and known pharmacokinetic profile. Based on the pharmacodynamic and pharmacokinetic kinetic profile of each enantiomer, a dose response curve was established for each of the aforementioned classes of receptors. The final selected ratio maximized scores for all major sorting criteria, namely reduced neurotoxicity, improved potency, improved clearance, and reduced abuse potential. The mixture of enantiomer salts selected optimizes these parameters, maximally placing the drug in an 'optimal therapeutic window.'

Results & Significance: Ratios of R:S MDMA from 6:4 to 95:5 were assessed. From this range, a 9:1 R:S MDMA non-racemic enantiomeric mixture unexpectedly demonstrated increased potency relative to the R-isomer alone, while retaining certain therapeutic effects specific to a lowered fraction of the S-isomer. Ratios above 9:1 did not retain affinity for $5\text{-HT}_{2A/1A}$ at levels comparable to racemic MDMA, lost all affinity at the $\alpha 4\beta 2$ nicotinic acetylcholine receptor, and required dose escalation to well outside of known MDMA-safe limits. Surprisingly, ratios below 9:1 exceeded neurotoxicity and hyperthermia associated with a 3.5 mg/kg dose of racemic MDMA.

Figure 6:
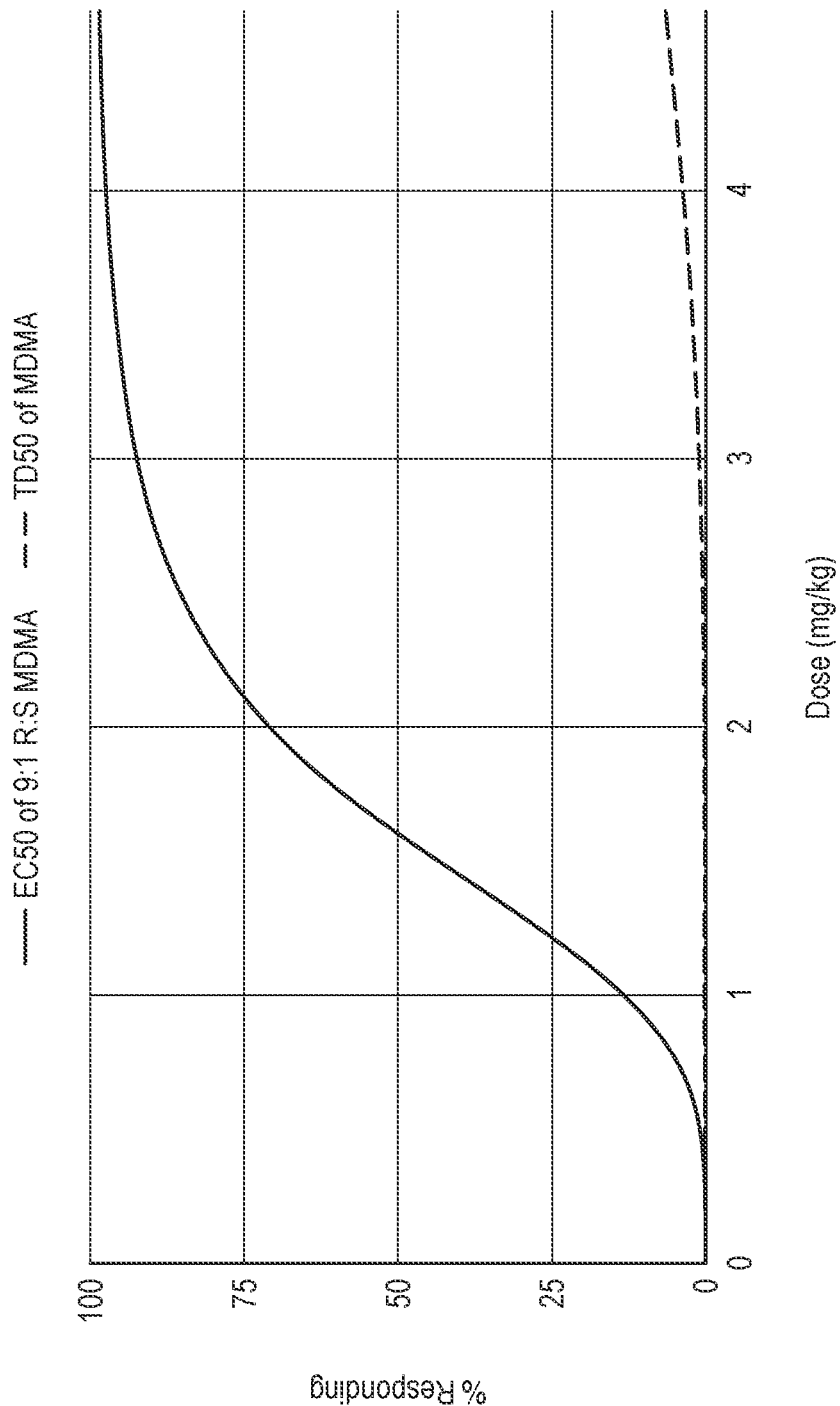
FIG. 6 shows a computed therapeutic index comparison of racemic MDMA ($TD_{50}$) and exemplary non-racemic mixture 9:1 R:S MDMA ($EC_{50}$).

Therapeutic Index: FIG. 6 shows a computed dose-response relationship for 9:1 R:S MDMA ($EC_{50}$) compared to the $TD_{50}$ of MDMA. Therapeutic Index is calculated by dividing $TD_{50}$ by $EC_{50}$, the dose required to produce a therapeutic effect in 50% of the population. Accordingly, the results show enhanced therapeutic index of 9:1 R:S MDMA relative to racemic MDMA.

Binding Profile: Binding of 9:1 R:S MDMA to SERT, NET, DAT, and $5\text{-HT}_{2A}$ was computed and compared to racemic MDMA. The calculated receptor affinities (km) of 9:1 R:S MDMA were >10,000 nM for DAT, 8300 nM for NET, and 2300 nM for SERT. Accordingly, the affinity profile for 9:1 R:S MDMA is SERT>>DAT>NET, which is comparable to that of R-MDMA (Verrico et al., Psychopharmacology (Berl), 2007; 189(4):489-503), indicating similar pharmacodynamics to the enantiomer.

Figure 7:
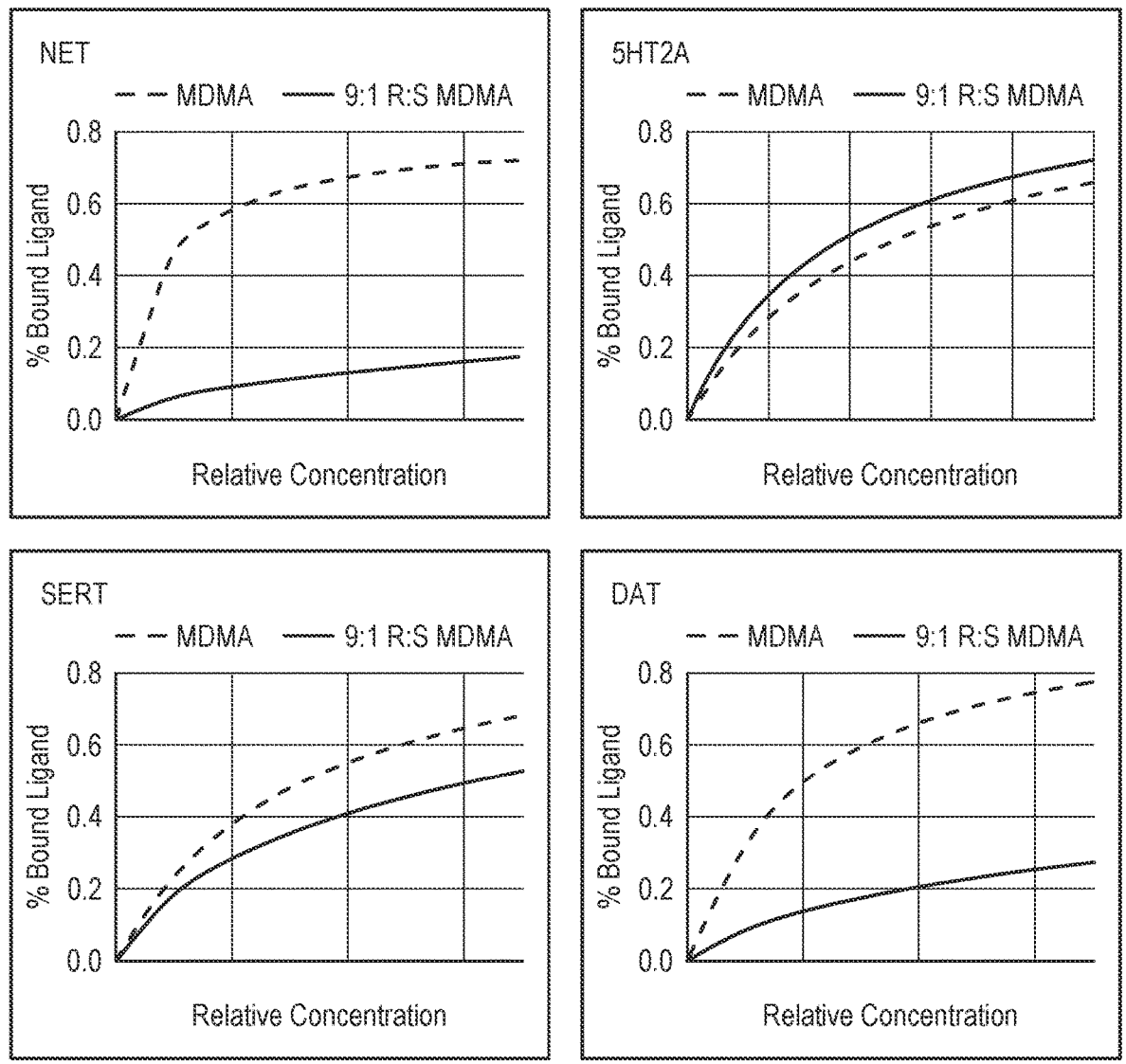
FIG. 7 shows computed comparative ligand binding of racemic MDMA and exemplary non-racemic mixture 9:1 R:S MDMA to norepinephrine transporter (NET), serotonin receptor 5-$HT_{2A}$, serotonin transporter (SERT), and dopamine transporter (DAT).

FIG. 7 shows computed ligand binding curves of racemic MDMA and exemplary non-racemic mixture 9:1 R:S MDMA. As shown, 9:1 R:S MDMA displays comparable ligand binding to racemic MDMA for $5\text{-HT}_{2A}$ and SERT. Serotonergic activity of MDMA is associated with therapeutic and prosocial effects, and the activity of 9:1 R:S MDMA at these sites obviates the need for dose escalation to produce comparable effects to MDMA. However, 9:1 R:S MDMA binding to NET and DAT was dramatically reduced relative to racemic MDMA. Accordingly, 9:1 R:S MDMA was shown to retain the serotonergic effects of MDMA and substantially reduce interactions with key mediators of toxicity.

9:1 R:S MDMA is expected to present a low risk of neurotoxicity or hyperthermia, which are primarily associated with dopamine release (via the DAT and the D1 receptors), as well as norepinephrine release via the transporter NET. Notably, the serotonergic system does not appear to be substantially involved in the neurotoxic and hyperthermia effects of MDMA. The R-enantiomer of MDMA, while being the less potent enantiomer, has proportionally fewer effects at D1, DAT, and NET and is significantly less effective at monoamine transport of dopamine and norepinephrine than serotonin, even when adjusting for dose, as compared to the S-enantiomer. Therefore, by reducing the fraction of the S-enantiomer from a racemic to a 9:1 R:S ratio, it is expected that the neurotoxic properties of MDMA will be significantly reduced or eliminated entirely.

Figure 8:
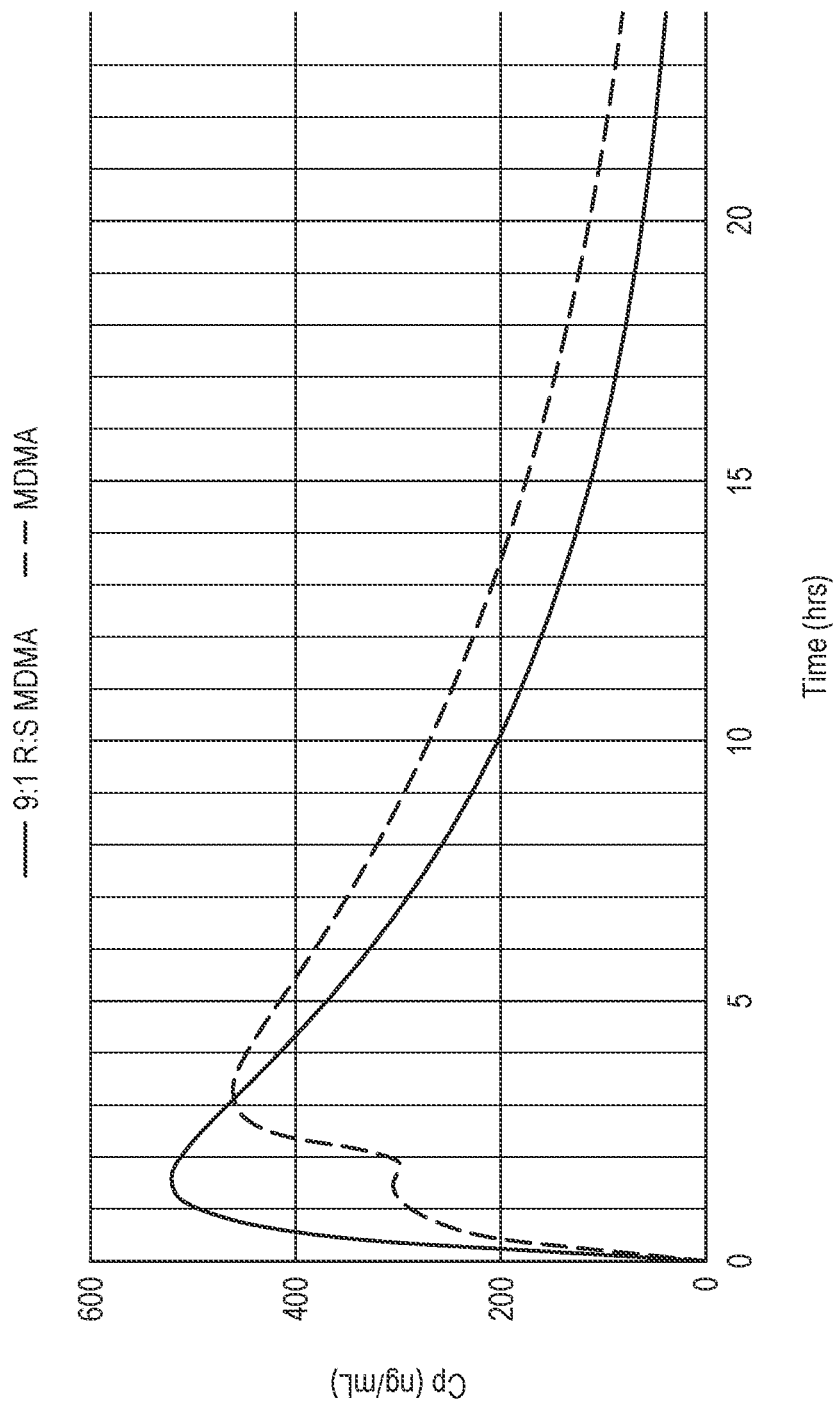
FIG. 8 shows computed mean plasma concentration (ng/ml) of racemic MDMA and exemplary non-racemic mixture 9:1 R:S MDMA over time (hrs).

Predicted Pharmacokinetics: FIG. 8 shows computed comparative plasma concentration-time profiles of an initial dose and a booster dose of racemic MDMA and a single dose of exemplary non-racemic mixture 9:1 R:S MDMA. 9:1 R:S MDMA shows a faster blood plasma clearance time as compared to a two dose racemate while having a longer half-life than a single dose of the racemate. In addition, due to the increased potency of the 9:1 mixture as opposed to the R-isomer alone, dose escalation widely outside of tested plasma concentration thresholds is not required.

Based on the results of the MAPS Phase II, and Phase III PTSD clinical trials, a regimen consisting of a 125 mg initial starting dose of MDMA, followed by a 62.5 mg 'booster' dose taken after two hours, has been shown to produce the highest therapeutic efficacy of the dosing regimens tested.

Notably, the booster dose of MDMA extends the therapeutic window of the drug and appears to lead to a larger effect size, compared to a single 125 mg dose alone. However, due to this second dose, clearance of the drug is substantially slower than could be achieved with a single dose, and it is partially responsible for the need to keep participants at the trial site overnight. A molecule with an equally broad therapeutic window with a faster clearance time would carry several benefits including a similar effect size, within a shorter time window.

Figure 9:
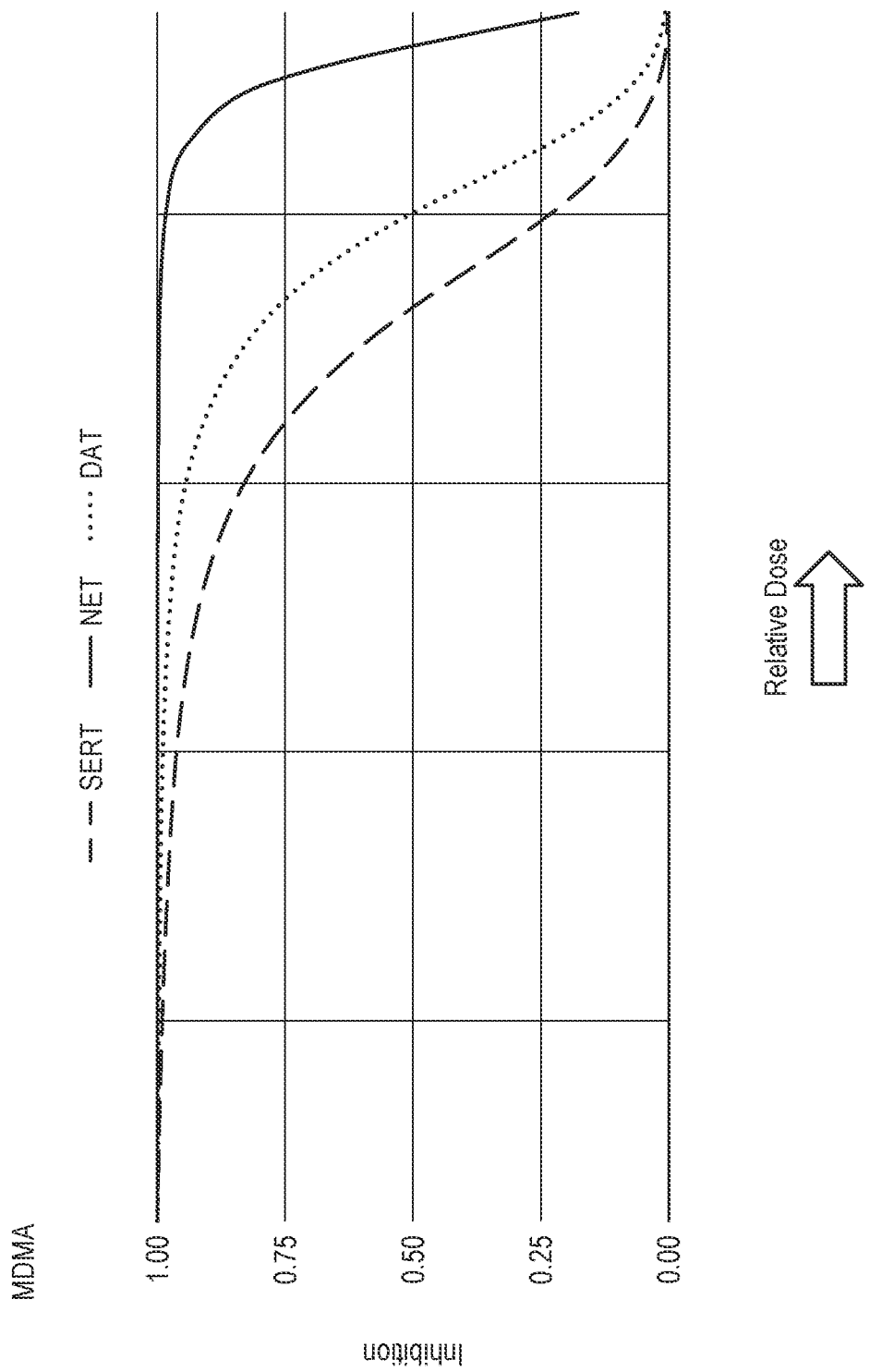
FIG. 9 shows calculated $IC_{50}$ curves of MDMA relative to the SERT, DAT, and NET, as normalized to the SERT.
Figure 10:
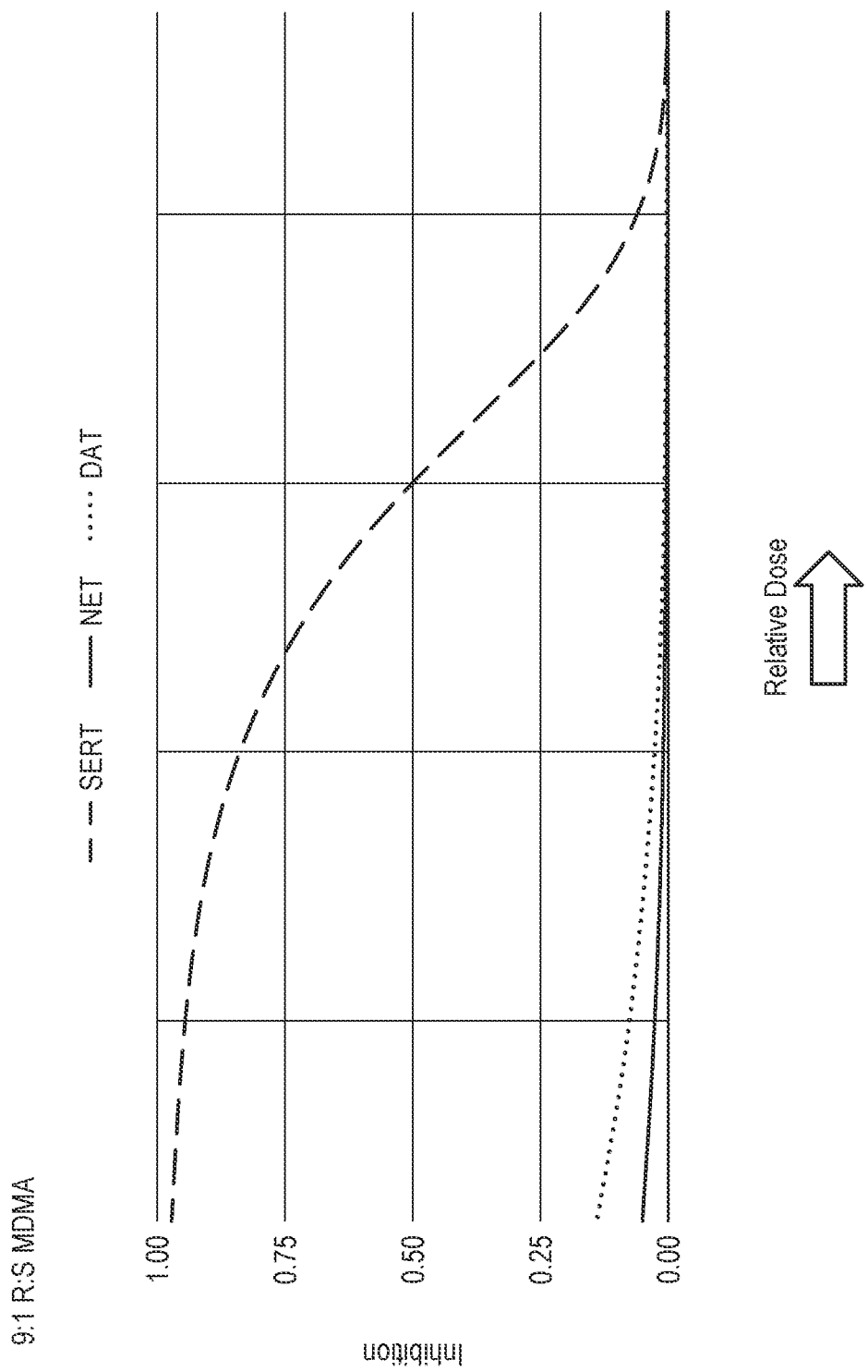
FIG. 10 shows calculated $IC_{50}$ curves of exemplary non-racemic mixture 9:1 R:S MDMA relative to the SERT, DAT, and NET, as normalized to the SERT.

Monoamine Transporters: FIG. 9 and FIG. 10 show binding of racemic MDMA and exemplary non-racemic mixture 9:1 R:S MDMA to SERT, DAT, and NET. Reducing the amount of S-MDMA and increasing the level of R-MDMA present in racemic levels substantially alters the binding profile of the drug.

Serotonin Transporter (SERT): FIG. 10 shows comparative binding at SERT, wherein racemic MDMA has the greatest potency, followed by non-racemic mixture 9:1 R:S MDMA, with R-MDMA displaying the least potency. The median expected SERT $K_m$ of racemic MDMA was calculated as 1490 nM±290, ~2000 nM for 9:1 R:S MDMA, and 22690 nM for R-MDMA. The relative difference in potency in optimal dosing between the enantiomers of MDMA as shown in animal behavior batteries is reflected in the relative difference in potency with respect to serotonin release and reuptake, via the SERT.

Figure 11:
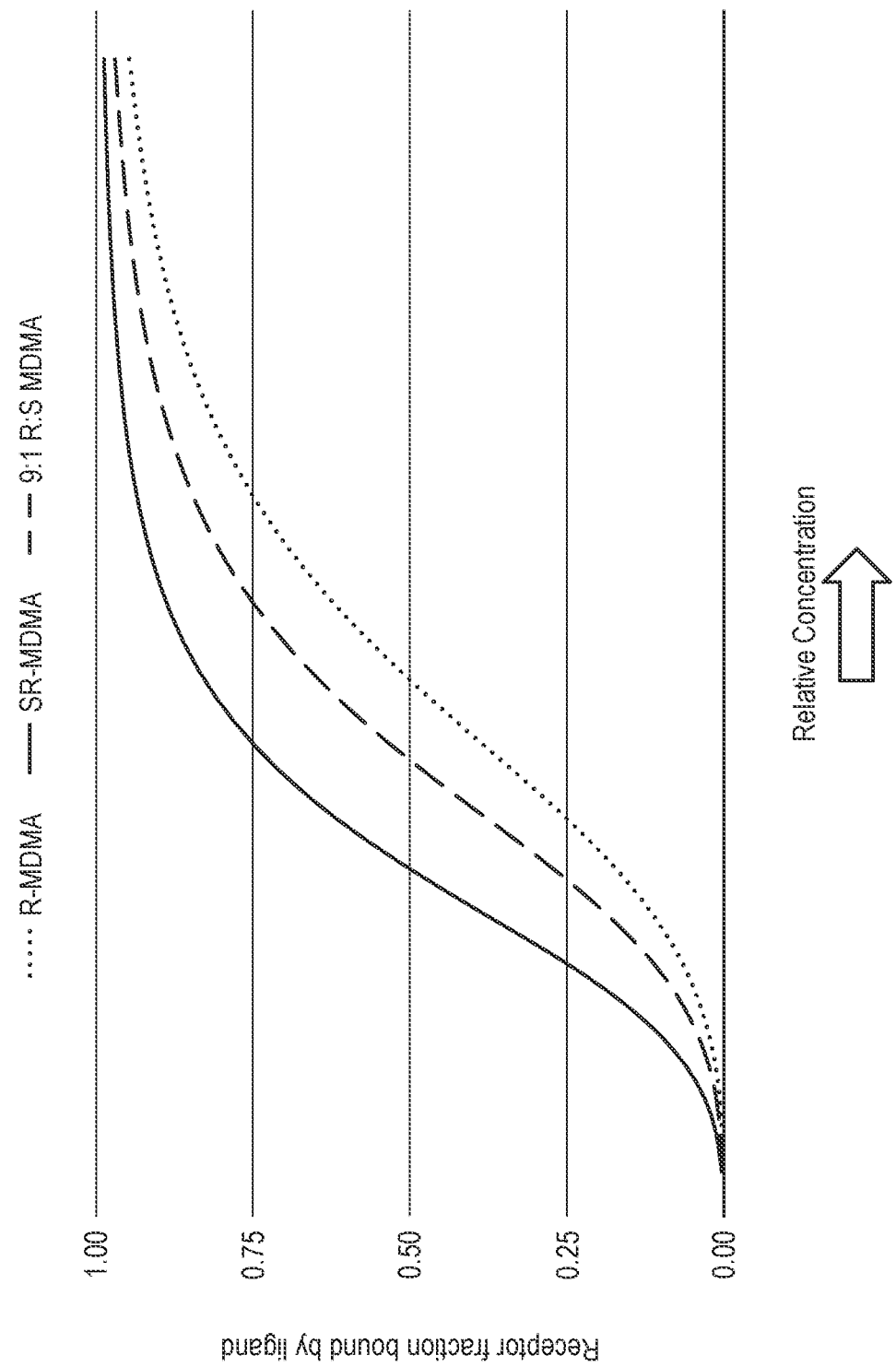
FIG. 11 shows relative potency of racemic MDMA, R-MDMA, and exemplary non-racemic mixture 9:1 R:S MDMA at SERT.
Figure 12:
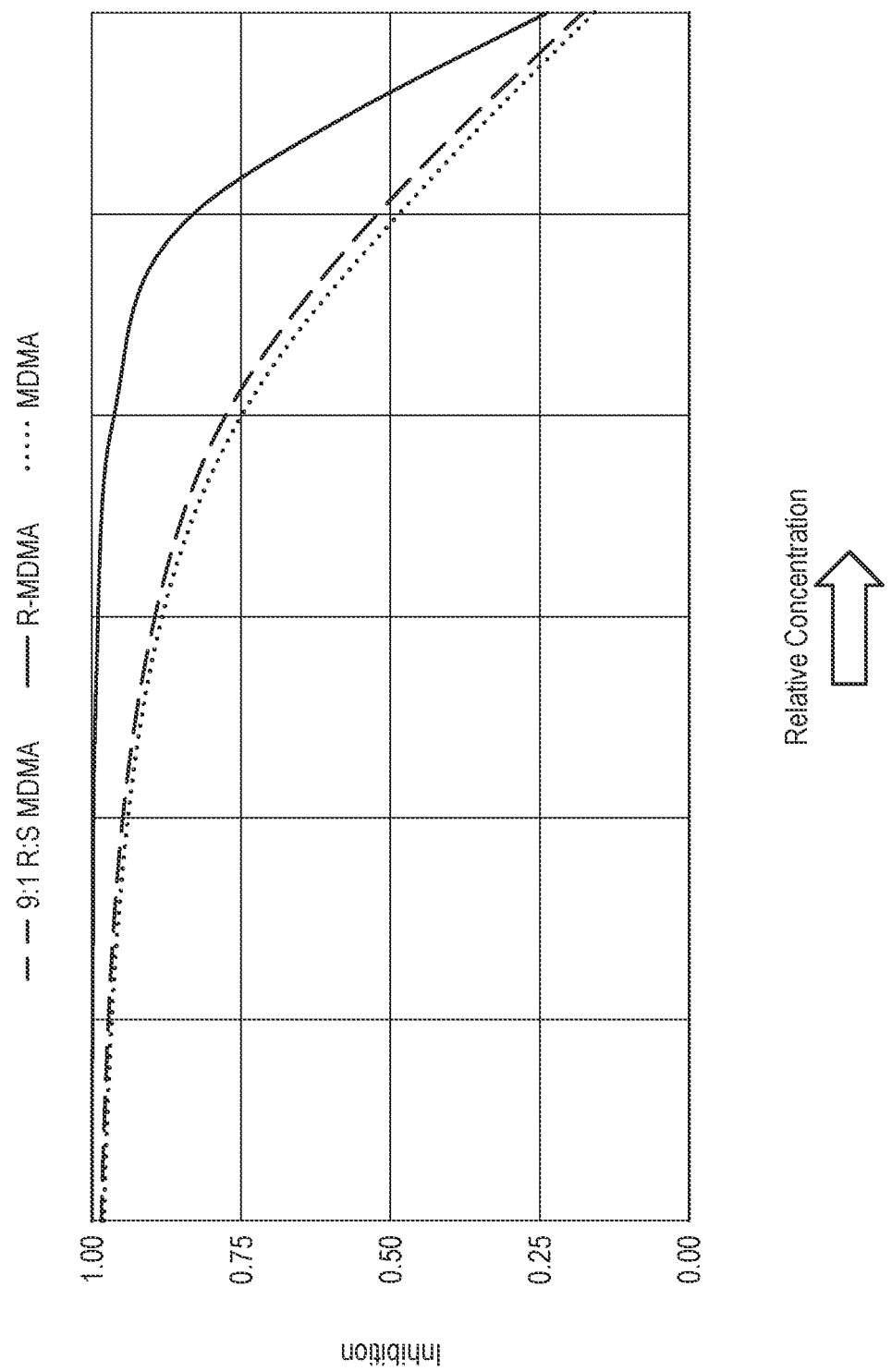
FIG. 12 shows calculated dose response of exemplary non-racemic mixture 9:1 R:S MDMA, MDMA, and R-MDMA at the alpha-4 beta-2 ($\alpha 4\beta 2$) nicotinic receptor subtype.

Reinforcement and Reward Learning: FIG. 11 shows dose-response activity between racemic MDMA and 9:1 R:S MDMA at the α4β2 nicotinic acetylcholine receptor (nAChR). Activity at the α4β2 nAChR of 9:1 R:S MDMA was surprisingly comparable to racemic MDMA. In comparison to racemic MDMA and the exemplary non-racemic enantiomeric mixture, R-MDMA had reduced activity at α4β2 nAChR.

Racemic MDMA has several favorable properties for the therapeutic context. Specifically, its competitive agonism at the α4β2 nAChR has been associated with MDMA's learning properties (Cordero-Erausquin et al., Trends Pharmacol Sci., 2000; 21(6):211-7), whereas R-MDMA does not have this effect (Llabres et. al, Eur J Med Chem., 2014; 81:35-46). 9:1 R:S MDMA surprisingly approximates the effects of racemic MDMA with regards to α4β2 nAChR-dependent memory and reinforcement.

Example 10: Synthesis of 9:1 R:S MDMA

Purpose: To synthesize an enantiomeric mixture of R-MDMA and S-MDMA in a ratio of 9:1.

Methods—Chiral Resolution of Sulfinamides: Scheme 4 shows synthesis started from commercially available 3,4-di-benzyloxybenzaldehyde, which was transformed into the methyl ketone (3) by condensation with nitroethane followed by reduction with Fe/HCl. The corresponding imine, formed by treatment of ketone (3) with (R)-(þ)-tert-butylsulfinamide and Ti(OEt)₄ was reduced in situ with NaBH₄ at room temperature to afford the two diastereomeric sulfinamides in excellent yield but with moderate (3:1) diastereomeric ratio. The diastereoselectivity rose to 14:1 by lowering the temperature to 20° C. in the reduction step. The major isomer was easily purified by crystallization from hexane affording diastereomerically pure (R,RS)-4a as a white solid.

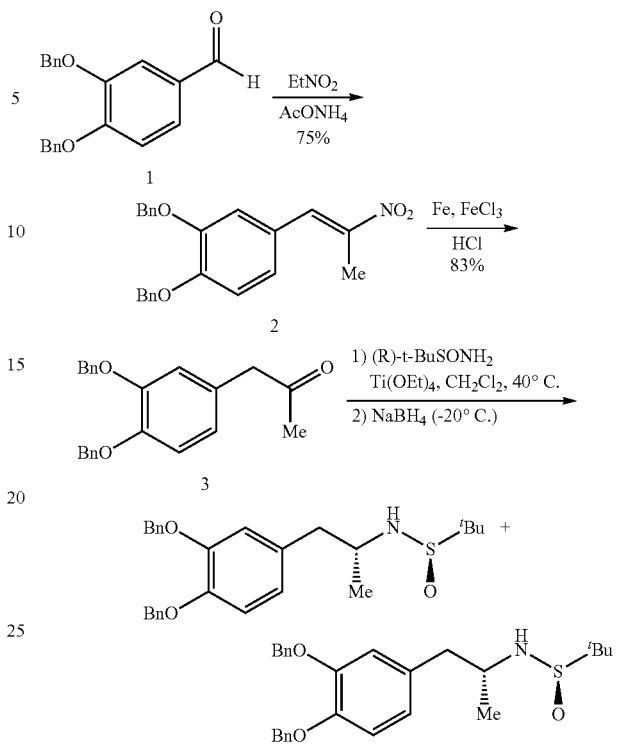

Scheme 4 shows chiral resolution of sulfinamides.

Enantioselective Synthesis of R-MDMA and S-MDMA: Methylation of sulfonamide (R,RS)-4a was carried out with NaH and MeI in DMF at room temperature to give (R,RS)-5a in 90% yield. However, cleavage of the benzyloxy groups by catalytic hydrogenation (Pd/C) even at high hydrogen pressures (50 bar) and/or temperatures (50° C.) was not achieved. It was hypothesized that sulphur byproducts derived from sulfinimides hampered the reaction poisoning of the catalyst.

Alternatively, derivatization of (R,RS)-4a as ethyl carbamate was unsuccessful since this sulfonamide is a very weak nucleophile. Thus, we envisaged the hydrolysis of (R,RS)-4a to the primary amine. Reductive cleavage of NeS bond was easily performed with 4 M MeOH/HCl in dioxane affording amine (R)-6a in 94% yield. Formation of the carbamate of the primary amine (R)-7a was carried out with ClCO₂Et, Et₃N in DMF. This compound was highly crystalline and allowed to confirm its high optical purity (99% ee by chiral HPLC). Cleavage of the dibenzyloxy group in (R)-7a could be performed by hydrogenolysis and the resulting diphenol was cyclized with bromochloromethane and cesium carbonate as described by Pizarro et al. Finally, reduction with lithium aluminium hydride in THE yielded the desired compound (R)-10a (MDMA) in 85% yield, which was isolated as a sulfate. The enantiomeric purity of the final product was checked by chiral HPLC of the corresponding N-Boc derivative, being 99% ee as expected. Since both enantiomers of tert-butylsulfinamide are commercially available, the same sequence as shown in Scheme 5, starting from (S)-(−)-tert-butylsulfinamide, afforded the (S)-MDMA enantiomer also in 99% ee.

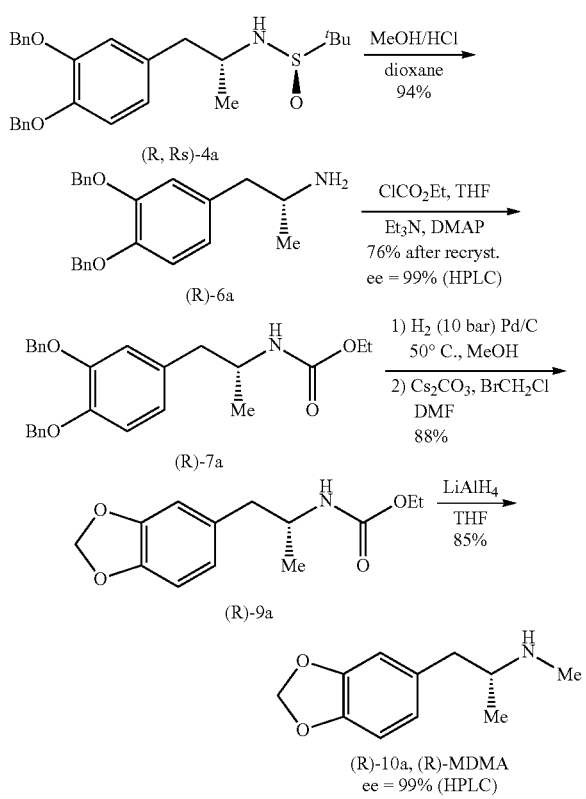

Scheme 5 shows an exemplary synthesis of R-MDMA from the R-enantiomer of a sulfinamide precursor.

Reconstitution In a 9:1 Ratio:Sulfate salts of R- and S-MDMA were recrystallized at a ratio of 9:1 and passed through a chiral column to ensure the correct enantiomeric ratio.

Example 11: Subjective Report of R-MDMA HCL

Purpose: To determine the physiological and subjective effects of the hydrochloride salt of R-MDMA (oral administration, 250 (±) 10 mg), supplemented with acetyl-L-carnitine (ALCAR), alpha lipoic acid (ALA), ascorbate to reduce or prevent neurotoxicity.

Methods—Synthesis and Chiral Separation: (from SR-MDMA): 2.2 g of racemic MDMA was obtained and dissolved in methanol at a stock concentration of 10 mg/mL. A ChiralPak Ad-H column (150×4.6 mm, 5 μm particle size) was flushed with mobile phase solution on an Agilent 1260 machine with a variable UV-Vis detector and 10 uL of the final concentrated solution (1:100) was injected on a 35 min run cycle. Due to the preliminary nature of the testing, no further characterization was done. The laevo-rich form was the first eluted. It was collected and roto-evaporated into solid form and then dried over magnesium pellets. The product, when dried and washed thoroughly, was sent out for anonymized 1H-NMR testing to determine identity.

Results—Physiological Effects: Vitals were taken hourly, and were taken four times between hours two and three. Heart rate rose for a short period to 115-125 from 85 resting. Blood pressure increased for a short period, however it was later determined that the monitor was of low precision and the result is therefore inconclusive. No noticeable hyperthermia or hypothermia was recorded. No incidence of jaw clenching was recorded.

Results—Subjective Effects of Subject A: "I slept well the previous night and came into the experience in a good mood. The initial dose was taken orally with 500 mg ALCAR and 300 mg ALA with the assumption that these two potentially neuroprotective agents would not significantly interfere with the subjective effects of R-MDMA. Blood pressure, heart rate, and temperature were taken and shown to be in normal range, though blood pressure was noticeably slightly elevated. For the first 30-40 minutes, I felt only slight lightheadedness. Noticeable effects off-baseline started somewhere around 40 minutes in, at which point the colors in the kitchen began to become slightly brighter and left slight ray traces when the visual frame moved. The empathogenic come-up was fast. Around the one hour mark, I was suddenly whacked in the head with an overwhelming, all-encompassing sense of compassion and love. Waves of euphoria rolled over the body, as if being cradled by the warm center of physical reality itself, the most perfect and sublime space. In many ways, it felt like coming back home, something that my life was leading me to, a kind of ultimate conclusion. My mind kept repeating to me: 'Oh my god, this is it, this is it!' Noticeably, unlike racemic MDMA, the R-MDMA experience was almost entirely absent of any high energy 'amphetamine'-like stimulant effects. This is probably not a substance that will make you dance. Instead, the waves of euphoria and troughs of gratitude were much more subdued and 'meditative.' It felt more like a spiritual type of grace. At the peak of the experience, somewhere around two hours after ingestion, my mind began to pan to various people in my life and focus in on the intense gratitude I felt for their existence and my knowing them and my desire for them to have a good and meaningful life. I talked consistently throughout the session, while also spending blocks of time exploring the entactogenic space. Every inch of my body was tingling with the waves of love and cradling that was coming from every direction. Notably the peak of R-MDMA was quite long and lasted several hours. When my eye mask was off, I looked around the room and noticed everything was more perfect and beautiful. Come-down started at approximately hour 4 and the whole experience lasted for approximately 7 hours, though glimmers of this total beauty and perfection lasted much much longer, well into the night. Definitely a (+++)."

Example 12: Subjective Report of a Non-Racemic Enantiomeric Mixture of R-MDMA and S-MDMA in a Ratio of 9:1

Purpose: To determine the subjective effects of oral 9:1 R:S MDMA.

Methods: In contrast to the previous report on R-MDMA, no supplements taken prior to oral administration of 230-240 mg 9:1 R:S MDMA. MDMA enantiomers were recombined in a 9:1 ratio through crystallization and washing.

Results & Significance: "Maybe it was the large size of the crystals which were ingested, but it took a long time to take effect, at least an hour and 10 minutes. The effect was very MDMA-like, maybe a tad less stimulating on the whole. Visuals were more noticeable after the first hour and a half. Heart rate seemed to be pretty steady the few times that we took vitals, somewhere in the 95 range. Not a lot of hot-and-cold feelings the whole time. Body euphoria was intense for the first three hours, then the comedown was pretty rapid. No jaw clenching either, but I usually don't get that anyway with the racemic form. Overall, a (+++). Relative to R enantiomer alone, the effects of the 9:1 R:S enantiomeric mixture, which were comparable to the entactogenic experience of R-MDMA alone, dissipated more rapidly."

Example 13: A Randomized and Double-Blind, Placebo-Controlled Dose Ranging and Safety Phase I Study Assessing 9:1 R:S-MDMA in a Healthy Participant Population for the Treatment of PTSD in Conjunction with Assisted Psychotherapy Purpose: The primary objective of this study is to determine the safety profile, optimal dose of 9:1 R:S-MDMA and to assess the therapeutic effect of 9:1 R:S-MDMA as a measure of change to Self Compassion Scale (SCS) assessment scores.

Methods: A randomized, dose escalation, double-blind, placebo-controlled, single site clinical healthy participant trial is completed to assess initial safety in humans and select the optimal dose of 9:1 R:S-MDMA, such as a mixture of R-MDMA HCl and S-MDMA HCl in a ratio of 9:1. Healthy participants recruited for the study will undergo one 8-hour experimental session followed by a day follow-up call and a call once a week for assessing the status of the participant for three weeks following a single dose of 9:1 R:S-MDMA.

The SCS assessment is a self-reported measure of self-compassion that will take approximately 10 to 15 minutes to complete. The SCS will be administered during the Experimental Session prior to administration, at the end of the Experimental Session, and at the study termination visit. The C-SSRS Assessment is a clinician-administered measure of suicidality that can be performed in person and as telemedicine. The lifetime version will be administered during the Screening Period and the Since Last Visit version will be performed for all other assessments:

Primary safety endpoints will include the proportion of subjects who experience at least one treatment-emergent adverse events (TEAEs) will be summarized by treatment arms. A two-sided 95% confidence interval will be estimated by the Clopper-Pearson exact method. The Mantel-Haenszel Chi-square test will be used to derive the comparison of the event rates among the treatment arms.

The above analysis for the treatment-emergent serious adverse events (TESAEs) will be reported in a similar manner. Secondary Endpoints will be evaluated by the changes of the vital sign parameters summarized by mean (median) and standard deviations. The comparison among treatment arms will be conducted by the analysis of variance (ANOVA) method for numeric values.

The dose response feedback will be summarized with descriptive statistics (counts and proportions) by treatment arms. Pharmacokinetic (PK) parameters will be summarized and mean, median, SD, and range will be presented by treatment arms. PK parameters will be transformed with the natural log transformation if needed. Comparisons among treatment arms will be performed by the ANOVA method or by the mixed model if applicable.

Results & Significance: The potential side effects seen in the literature with racemic MDMA are expected to be absent or reduced in response to administration of 9:1 R:S-MDMA. The potential risk of a study participant being severely agitated, anxious or depressed is low. The enantiomeric mixture is expected to produce a slight increase in body temperature, if any, no risk of osmoregulatory changes. Following completion of the Phase I study, the safety profile of R-MDMA HCl and S-MDMA in a 9:1 ratio will be assessed and dose selection will be performed. If no serious adverse incidents are observed, the optimal dose will be selected for the Phase II trial.

Example 14: A Phase 2 Randomized, Double-Blind, Placebo-Controlled, Multi-Site Study Evaluating the Efficacy and Safety of 9:1 R:S-MDMA in Conjunction with Assisted Psychotherapy for Treatment of Moderate to Severe PTSD Purpose: A randomized, double-blind, placebo-controlled, multi-site clinical trial is conducted to assess the efficacy and safety of 9:1 R:S-MDMA in PTSD patients.

Methods: Participants recruited for the study will undergo three 8-hour experimental sessions spaced three weeks apart with a single dose of R-MDMA HCl and S-MDMA in a 9:1 ratio. Study participants will be given either one dose of 9:1 R:S-MDMA or placebo combined with psychotherapy every three weeks in an outpatient setting. A total of three doses are selected in this study due to the positive response observed in the MAPS trial employing a total of three doses.

Subjects participate in a screening period, a preparatory period, a treatment period, and a follow-up period prior to termination.

Screening period: phone screen, site visit for informed consent, eligibility assessment and enrollment of eligible participants Preparatory period: medication tapering, baseline assessments Treatment period: three experimental sessions over an approximate 9-week period (sessions every ~3 weeks) with two associated Integrative sessions performed between each experiment session Follow-up period and study termination: in person follow-up nine weeks after last experimental session IR+QoL visit, study termination visit Exemplary details for each period are described below in Tables 2-5.

TABLE 2

Exemplary screening period
Screening Period (from consent to enrollment~4 weeks)

| Study Visit | Visit Duration/Timing | Brief description of events |
|---|---|---|
| Screening | Multiple visits over 7-28 days after phone screening | At initial visit, obtain informed consent and assess all screening measures (Lifetime C-SSRS), medical history and pre-study medications. Contact outside providers and order medical records, physical exam, labs (including pregnancy and drug tests), ECG with a1-minute rhythm strip. |

TABLE 2-continued

Exemplary screening period
Screening Period (from consent to enrollment~4 weeks)

| Study Visit | Visit Duration/Timing | Brief description of events |
|---|---|---|
| Independent Rater Screening | 1 hour/ 2 to 9 days after initial eligibility established during screening | Once all results and records are obtained, review along with notes from all screening visits and measures. Screening may take place over 7 to 28 days at multiple visits. After initial eligibility is reviewed, an IR will conduct the since last visit C-SSRS and MINI via telemedicine. Results will be confirmed by clinical observation during the preparatory period but the MINI assessment will not be repeated. |
| Enrollment | 1.5 hours/ Perform at last screening visit | Review all screening measures, medical history, discussion with outside providers and sponsors, and any clarification phone calls with participants. Visit is 1.5 hours to review eligibility and medical tapering plan. If enrolled, begin taper, (5 half-lives plus 7 days for stabilization). Adverse Event (AE) collection begins. |

TABLE 3

Exemplary preparatory period
Preparatory Period (~6 weeks)

| Study Visit | Visit Duration/Timing | Brief description of events |
|---|---|---|
| Preparatory session 1 | 1.5 hours/ 0-12 days after enrollment | Target visit timing on tapering needs. If needed, schedule calls between visits if indicated for tapering, safety, or further questions about medical history. Tapering period may vary from patient to patient |
| Preparatory session 2 | 1.5 hours/ 2 to 21 days after enrollment | Ongoing assessment. If tapering is complete or not needed, check eligibility and schedule upcoming visits. If tapering is ongoing, schedule a post taper call for ongoing assessment. |
| End Tapering | 1 hour/ 0 to 7 days after taper and stabilization ends | Confirm medication taper and stabilization is complete and the participant is eligible for baseline CAPS-5 and SDS assessment. Schedule IR assessments and final preparatory visit |
| Baseline CAPS-5 | 1.5 hours/ Post preparatory session 2 and medication tapering and before preparatory session 3 | CAPS-5 and SDS completed by an IR via telemedicine after tapering is complete. CAPS-5 and SDS scores are sent to the study site for assessment immediately after completion. Due to possibilities of negative side effects of withdrawal from psychiatric medications, the baseline CAPS-5 and SDS should be scheduled as close to the end of tapering as clinically appropriate so that participants who do not meet eligibility criteria can resume their previously prescribed medications as quickly as required for symptom management and participants who do meet criteria can be enrolled and treated as quickly as possible. |
| Preparatory session 3 | 3 hours (90 minute measures, 90 minute therapy)/ 3 to 6 days after baseline CAPS-5 | Complete baseline QoL (TBD) for quality of life self-report measures Schedule experimental session 1 and if enrollment is not confirmed, do not randomize and document as a screen failure. |

TABLE 4

Exemplary treatment period
Treatment Period (from randomization to integrative session 3.2 (9 weeks))

| Study Visit | Visit Duration/Timing | Brief description of events |
|---|---|---|
| Randomization | 0.5 hours/ 24 to 48 hours before experimental session 1 | Complete after enrollment and scheduling Exp. Session 1. Record demographics for use in randomization. The participant does not need to be present for this |
| Experiment Session 1 | 8 hours/ Within 2 weeks of final preparatory visit | 8 hour session. Exemplary non-racemic mixture of 9:1 R:S MDMA or placebo dose administered An overnight stay is only recommended by the physician/therapist |
| Integrative Session 1.1 | 1.5 hours/ Morning after experimental session 1 | 90-minute integrative session followed by phone check-ins that includes since last visit C-SSRS assessment on days 2, 4, 6, 8, and 10 post experiment session |
| Integrative Session 1.2 | 1.5 hours/ 7 days after experimental session 1; at least 2 days after integrative session 1.1 | 90-minute integrative session complete Perform IR assessment during phone check-in following second integrative session to complete CAPS-5 and SDS assessments |
| Experiment Session 2 | 8 hours/ 21 to 35 days after experimental session 1 | 8 hour session. Exemplary non-racemic mixture of 9:1 R:S MDMA or placebo dose administered An overnight stay only if recommended by the physician/therapist |
| Integrative Session 2.1 | 1.5 hours/ Morning after experimental session 2 | 90-minute integrative session including QOL (TBD) assessment followed by phone check-ins that includes since last visit C-SSRS assessment on days 2, 4, 6, 8, and 10 post experiment session |
| Integrative Session 2.2 | 1.5 hours/ 7 days after experimental session 2; at least 2 days after integrative session 2.1 | 90-minute integrative session complete Perform IR assessment during phone check-in following second integrative session to complete CAPS-5 and SDS assessments |
| Experiment Session 3 | 8 hours/ 21 to 35 days after experimental session 2 | 8 hour session. Exemplary non-racemic mixture of 9:1 R:S MDMA or placebo dose administered An overnight stay only if recommended by the physician/therapist |
| Integrative Session 3.1 | 1.5 hours/ Morning after experimental session 3 | 90-minute integrative session followed by phone check-ins that includes since last visit C-SSRS assessment on days 2, 4, 6, 8, and 10 post experiment session |
| Integrative Session 3.2 | 1.5 hours/ 7 days after experimental session 3; at least 2 days after integrative session 3.1 | 90-minute integrative session complete Perform IR assessment during phone check-in following second integrative session to complete CAPS-5, SDS, and QoL TBD assessments |

TABLE 5

Exemplary termination period
Follow-up/Study Termination Period (from integrative session 3.2 until study termination (3 weeks))

| Study Visit | Visit Duration/Timing | Brief description of events |
|---|---|---|
| Follow-up/ Termination | 2 hours/ 1 to 9 days after integrative session 3.2 | Complete CAPS-5, SDS, since last visit C-SSRS and QoL assessments, perform safety measures, and create an exit plan for the participant. Let participant who completed the protocol know how they will be performed of unblinding |

The primary endpoint is to demonstrate that 9:1 R:S-MIDMA induces a larger reduction in Clinician Administered PTSD Scale for DSM-5 (CAPS-5) score from baseline after 3 sessions of treatment than placebo. The primary endpoint is the change of CAPS-5 score from the baseline to the end of the final treatment session. For reference, a higher CAPS-5 score means more severe PTSD.

The CAPS-5 scale is selected as the primary measure for evaluating 9:1 R:S MDMA because the CAPS scale is the gold standard in PTSD assessment. The CAPS-5 is a 30-item structured interview that can be used to: (1) Make current (past month) diagnosis of PTSD; (2) Make lifetime diagnosis of PTSD; and (3) Assess PTSD symptoms over time.

CAPS-5 scale has been employed in other human PTSD trials including the MAPS-sponsored MDMA PTSD trial. MAPS originally used as a primary endpoint the CAPS-4 scale and upgraded to the CAPS-5 scale upon its release.

The following secondary safety endpoints were selected as secondary safety measures because they compare the efficacy/safety of 9:1 R:S MDMA and placebo therapies.

Proportion of subjects who have achieved clinically significant improvement (Yes/No) defined as a decrease of ≥10 points on the CAPS-5, loss of diagnosis (specific diagnostic measure on the CAPS-5), and remission (loss of diagnosis and a total CAPS-5 score≤11) at each of treatment session.

Sheehan disability scale (SDS): The SDS scale is a five-item, self-rated questionnaire designed to measure the extent to which a patient's disability due to an illness or health problem interferes with work/school, social life/leisure activities, and family life/home responsibilities. The SDS also assesses impairment in patients with panic disorder.

An evaluation of the patients' quality of life (QOL). QOL may be measured by ProQOL, which includes subscales compassion satisfaction, burnout and secondary traumatic stress The number and percent of participants reporting the presence of suicidal ideation and endorsing any positive ideation as measured with the C-SSRS at each visit and separated by treatment group are determined. C-SSRS ideation scores range from 0 (no ideation) to 5. A C-SSRS ideation score of 4 or 5 is termed 'serious ideation' and a C-SSRS ideation score >0 is termed 'any positive ideation.'

Results & Significance: 9:1 R:S MDMA is anticipated to demonstrate strong safety and efficacy as part of a clinical program. The compound is used to treat PTSD. Evidence of a positive effect facilitates pursuit of investigational clinical studies for additional indications.

Example 15: Comparative Metabolism and Clearance of Racemic MDMA, MDMA Enantiomers and Non-Racemic Mixtures Thereof Purpose: To determine the metabolism of non-racemic mixtures of MDMA in comparison to single enantiomers and racemic MDMA Methods: Metabolism and clearance are determined according to the methods described in Meyer et al., Drug Metab Dispos. 2008; 36(11):2345-54. Briefly, test samples are incubated using heterologously expressed human P450s, and the metabolites are quantified by gas chromatography-mass spectrometry after derivatization with S-heptafluorobutyrylprolyl chloride. Enzyme kinetic data is used to determine net clearance and the contributions of CYP450 isoforms.

Results & Significance: Overall clearance of exemplary non-racemic mixture 9:1 R:S MDMA is expected to be greater than R-MDMA. In comparison to racemic MDMA, metabolism of the non-racemic mixture by CYP2D6 and CYP2C19 is expected to be reduced. The results are anticipated to be reflective of in vivo effects, indicating, e.g., reduced duration of action relative to R-MDMA and a reduced potential for drug-drug interactions at CYP2D6 and CYP2C19.

The foregoing description, for purposes of explanation, uses specific nomenclature to provide a thorough understanding of the invention. However, it will be apparent to one of skill that specific details are not required in order to practice the invention. Thus, the foregoing description is presented for purposes of illustration and description, and is not intended to be exhaustive or to limit the invention to the precise forms disclosed; many modifications and variations are possible in view of these teachings. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed. Accordingly, the scope of the invention shall be defined solely by the following claims and their equivalents.

The invention claimed is:

1. A non-racemic mixture comprising R(−)-3,4-methylenedioxymethamphetamine (R-MDMA) or a pharmaceutically acceptable salt thereof, and S(+)-3,4-methylenedioxymethamphetamine (S-MDMA) or a pharmaceutically acceptable salt thereof, in a molar ratio of R-MDMA to S-MDMA of 9:1.

2. The non-racemic mixture of claim 1, wherein the salts are any of fumarate, malonate, maleate, malate, phosphate, tartrate, galactarate, succinate, tosylate, hydrochloride, or hydrobromide salts.

3. The non-racemic mixture of claim 1, wherein the salt of R-MDMA is a hydrochloride salt, and the salt of S-MDMA is a hydrochloride salt.

4. A pharmaceutical composition comprising a non-racemic mixture of R(−)-3,4-methylenedioxymethamphetamine (R-MDMA) or a pharmaceutically acceptable salt thereof, and S(+)-3,4-methylenedioxymethamphetamine (S-MDMA), or a pharmaceutically acceptable salt thereof, in a molar ratio of R-MDMA to S-MDMA of 9:1.

5. The pharmaceutical composition of claim 4, wherein the pharmaceutically acceptable salts are any of fumarate, malonate, maleate, malate, phosphate, tartrate, galactarate, succinate, tosylate, hydrochloride, or hydrobromide salts.

6. The pharmaceutical composition of claim 4, wherein the pharmaceutically acceptable salt of R-MDMA is a hydrochloride salt, and the pharmaceutically acceptable salt of S-MDMA is a hydrochloride salt.

7. The pharmaceutical composition of claim 4 in unit dosage form.

8. The unit dosage form of claim 7, comprising the non-racemic mixture in an amount of between 50 mg and 300 mg, 100 mg and 300 mg, 150 mg and 300 mg, 200 mg and 300 mg, 200 mg and 250 mg, 62 mg and 285 mg, 62 mg and 235 mg, 141 mg and 285 mg, or 141 mg and 235 mg.

9. A method of modulating neurotransmission in a subject, comprising administering to the subject a therapeutically effective amount of a pharmaceutical composition comprising a non-racemic mixture of R(−)-3,4-methylenedioxymethamphetamine (R-MDMA) or a pharmaceutically acceptable salt thereof, and S(+)-3,4-methylenedioxymethamphetamine (S-MDMA), or a pharmaceutically acceptable salt thereof, in a molar ratio of R-MDMA to S-MDMA of 9:1.

10. The method of claim 9, comprising administering the non-racemic mixture in an amount of between 50 mg and 300 mg, 100 mg and 300 mg, 150 mg and 300 mg, 200 mg and 300 mg, 200 mg and 250 mg, 62 mg and 285 mg, 62 mg and 235 mg, 141 mg and 285 mg, or 141 mg and 235 mg.

11. The method of claim 9, wherein the neurotransmission is one or more of serotonergic neurotransmission, dopaminergic neurotransmission, and noradrenergic neurotransmission.

12. The method of claim 9, wherein modulating neurotransmission comprises reduced norepinephrine release and/or dopamine release compared to racemic MDMA.

13. The method of claim 12, wherein reduced norepinephrine release and/or dopamine release reduces abuse potential and/or reduces neurotoxicity relative to racemic MDMA.

14. A method of treating a mental health disorder in a subject, comprising administering to the subject a therapeutically effective amount of a pharmaceutical composition comprising a non-racemic mixture of R(−)-3,4-methylenedioxymethamphetamine (R-MDMA) or a pharmaceutically acceptable salt thereof, and S(+)-3,4-methylenedioxymethamphetamine (S-MDMA), or a pharmaceutically acceptable salt thereof, in a molar ratio of R-MDMA to S-MDMA of 9:1.

15. The method of claim 14, comprising administering the non-racemic mixture in an amount of between 50 mg and 300 mg, 100 mg and 300 mg, 150 mg and 300 mg, 200 mg and 300 mg, 200 mg and 250 mg, 62 mg and 285 mg, 62 mg and 235 mg, 141 mg and 285 mg, or 141 mg and 235 mg.

16. The method of claim 14, wherein the mental health disorder is selected from the group consisting of: depression, major depressive disorder (MDD), treatment-resistant depression (TRD), atypical depression, postpartum depression, catatonic depression, a depressive disorder due to a medical condition, premenstrual dysphoric disorder, seasonal affective disorder, dysthymia, anxiety and phobia disorders, generalized anxiety disorder (GAD), agoraphobia, panic disorder, separation anxiety disorder, social anxiety disorder, post-traumatic stress disorder (PTSD), adjustment disorders, feeding and eating disorders, including binge eating, bulimia, and anorexia nervosa, other binge behaviors, body dysmorphic syndromes, drug abuse or dependence disorders, disruptive behavior disorders, impulse control disorders, gaming disorders, gambling disorders, memory loss, dementia of aging, attention deficit hyperactivity disorder (ADHD), personality disorders, including antisocial, avoidant, borderline, histrionic, narcissistic, obsessive compulsive, paranoid, schizoid and schizotypal personality disorders, attachment disorders, autism, social anxiety in autistic subjects, and dissociative disorders.

17. The method of claim 16, wherein the mental health disorder is PTSD.

18. The method of claim 16, wherein the mental health disorder is GAD.

19. The method of claim 16, wherein the mental health disorder is autism or social anxiety in autistic subjects.

20. The method of claim 14, wherein the pharmaceutical composition is administered in combination with psychotherapy.

21. The pharmaceutical composition of claim 4, wherein the composition is suitable for oral, mucosal, rectal, subcutaneous, intravenous, intramuscular, intranasal, inhaled, or transdermal administration.

22. The pharmaceutical composition of claim 4, suitable for oral administration.

23. The unit dosage form of claim 7, suitable for oral administration.

24. The unit dosage form of claim 23, formulated as a tablet or a capsule.

25. The unit dosage form of claim 7, wherein the unit dosage form is an immediate release, controlled release, sustained release, extended release, delayed release, or modified release formulation.

26. The unit dosage form of claim 7, comprising the non-racemic mixture in an amount of between 141 mg and 235 mg.

27. The method of claim 9, wherein the non-racemic mixture is orally administered.

28. The method of claim 10, comprising administering the non-racemic mixture in an amount of between 141 mg and 235 mg.

29. The method of claim 14, wherein the non-racemic mixture is orally administered.

30. The method of claim 15, comprising administering the non-racemic mixture in an amount of between 141 mg and 235 mg.

* * * * *